United States Patent
Messerly et al.

(10) Patent No.: US 10,842,522 B2
(45) Date of Patent: Nov. 24, 2020

(54) ULTRASONIC SURGICAL INSTRUMENTS HAVING OFFSET BLADES

(71) Applicant: Ethicon Endo-Surgery, LLC, Guaynabo, PR (US)

(72) Inventors: Jeffrey D. Messerly, Cincinnati, OH (US); Cory G Kimball, Hamilton, OH (US); William E. Clem, Bozeman, MT (US); Gregory W. Johnson, Milford, OH (US); Frederick Estera, Cincinnati, OH (US); William B. Weisenburgh, II, Maineville, OH (US); Foster B. Stulen, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 409 days.

(21) Appl. No.: 15/211,402

(22) Filed: Jul. 15, 2016

(65) Prior Publication Data
US 2018/0014848 A1 Jan. 18, 2018

(51) Int. Cl.
*A61B 17/32* (2006.01)
*A61N 7/00* (2006.01)
(Continued)

(52) U.S. Cl.
CPC ........... *A61B 17/320092* (2013.01); *A61B 17/320068* (2013.01); *A61N 7/00* (2013.01); *A61B 2017/00738* (2013.01); *A61B 2017/320072* (2013.01); *A61B 2017/320074* (2017.08); *A61B 2017/320088* (2013.01); *A61B 2017/320094* (2017.08); *A61B 2017/320095* (2017.08); *A61B 2018/00589* (2013.01)

(58) Field of Classification Search
CPC ............. A61N 7/00; A61B 17/320092; A61B 17/320068; A61B 2017/320094; A61B 2017/320074; A61B 2017/00438; A61B 2017/00738; A61B 2017/320088; A61B 2017/320072; A61B 2018/00589; A61B 17/285; A61B 17/295; A61B 17/3211
See application file for complete search history.

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CA | 2535467 A1 | 4/1993 |

(Continued)

OTHER PUBLICATIONS

Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.

(Continued)

*Primary Examiner* — Todd J Scherbel
*Assistant Examiner* — Mikail A Mannan

(57) ABSTRACT

Ultrasonic surgical instruments having angularly and/or linearly off-set blades are described. The angularly and/or linearly off-set blades may facilitate increased surgical site access, visibility, and manipulability.

19 Claims, 44 Drawing Sheets

(51) Int. Cl.
*A61B 17/00* (2006.01)
*A61B 18/00* (2006.01)

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,707 A | 8/1991 | Taheri |
| 5,047,043 A * | 9/1991 | Kubota ............ A61B 17/22012 606/169 |

(56) References Cited

U.S. PATENT DOCUMENTS

| | | |
|---|---|---|
| 5,061,269 A | 10/1991 | Muller |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,209,719 A | 5/1993 | Baruch et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,403,334 A | 4/1995 | Evans et al. |
| 5,408,268 A | 4/1995 | Shipp |
| 5,409,453 A * | 4/1995 | Lundquist .......... A61B 10/0233 604/22 |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,443,463 A | 8/1995 | Stern et al. |
| 5,445,638 A | 8/1995 | Rydell et al. |
| 5,445,639 A | 8/1995 | Kuslich et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |

(56) References Cited

U.S. PATENT DOCUMENTS

| | | |
|---|---|---|
| 5,562,609 A | 10/1996 | Brumbach |
| 5,562,610 A | 10/1996 | Brumbach |
| 5,562,659 A | 10/1996 | Morris |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,155 A | 7/1998 | Beaupre et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,959 A | 8/1998 | Castro et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,007,552 A | 12/1999 | Fogarty et al. |
| 6,013,052 A | 1/2000 | Durman et al. |
| 6,024,741 A | 2/2000 | Williamson, IV et al. |

(56) References Cited

U.S. PATENT DOCUMENTS

| | | |
|---|---|---|
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,142 B1 | 10/2002 | Faller et al. |
| 6,464,689 B1 | 10/2002 | Qin et al. |
| 6,464,702 B2 | 10/2002 | Schulze et al. |

(56) References Cited

U.S. PATENT DOCUMENTS

| | | |
|---|---|---|
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B2 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B1 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |

(56) References Cited

U.S. PATENT DOCUMENTS

| | | |
|---|---|---|
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |

(56) References Cited

U.S. PATENT DOCUMENTS

| | | |
|---|---|---|
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |

(56) References Cited

U.S. PATENT DOCUMENTS

| | | |
|---|---|---|
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,871,392 B2 | 1/2011 | Sartor |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,323 B2 | 1/2012 | Buysse et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,415 B2 | 7/2012 | Francischelli |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |

(56) References Cited

U.S. PATENT DOCUMENTS

| | | |
|---|---|---|
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,880 B2 | 1/2013 | Messerly et al. |
| 8,348,967 B2 | 1/2013 | Stulen |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,640,788 B2 | 2/2014 | Dachs, II et al. |
| 8,647,350 B2 | 2/2014 | Mohan et al. |
| 8,650,728 B2 | 2/2014 | Wan et al. |
| 8,652,120 B2 | 2/2014 | Giordano et al. |

(56) References Cited

U.S. PATENT DOCUMENTS

| | | |
|---|---|---|
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,689 B2 | 8/2015 | Robertson et al. |
| 9,107,690 B2 | 8/2015 | Bales, Jr. et al. |
| 9,113,900 B2 | 8/2015 | Buysse et al. |

(56) References Cited

U.S. PATENT DOCUMENTS

| | | |
|---|---|---|
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,179,912 B2 | 11/2015 | Yates et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,486,236 B2 | 11/2016 | Price et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |

(56) References Cited

U.S. PATENT DOCUMENTS

| | | |
|---|---|---|
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0006269 A1 | 1/2004 | Novak et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |

(56) References Cited

U.S. PATENT DOCUMENTS

| | | |
|---|---|---|
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0158307 A1 | 6/2010 | Kubota et al. |
| 2010/0168741 A1 | 7/2010 | Sanai et al. |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0298743 A1 | 11/2010 | Nield et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0087220 A1 | 4/2011 | Felder et al. |
| 2011/0125151 A1 | 5/2011 | Strauss et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |

(56) References Cited

U.S. PATENT DOCUMENTS

| | | |
|---|---|---|
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0059289 A1 | 3/2012 | Nield et al. |
| 2012/0071863 A1 | 3/2012 | Lee et al. |
| 2012/0078139 A1 | 3/2012 | Aldridge et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116265 A1 | 5/2012 | Houser et al. |
| 2012/0143211 A1 | 6/2012 | Kishi |
| 2012/0143233 A1 | 6/2012 | Sinelnikov |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0211395 A1 | 8/2013 | Schwartz |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005704 A1* | 1/2014 | Vakharia ........ A61B 17/320092 606/169 |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0114327 A1 | 4/2014 | Boudreaux et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0276970 A1 | 9/2014 | Messerly et al. |
| 2014/0323926 A1 | 10/2014 | Akagane |
| 2014/0330271 A1 | 11/2014 | Dietz et al. |
| 2014/0371735 A1 | 12/2014 | Long |
| 2015/0005796 A1 | 1/2015 | Isola et al. |
| 2015/0011889 A1 | 1/2015 | Lee |
| 2015/0080876 A1 | 3/2015 | Worrell et al. |
| 2015/0088178 A1 | 3/2015 | Stulen et al. |
| 2015/0112335 A1 | 4/2015 | Boudreaux et al. |
| 2015/0148830 A1 | 5/2015 | Stulen et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182276 A1 | 7/2015 | Wiener et al. |
| 2015/0182277 A1 | 7/2015 | Wiener et al. |
| 2015/0230853 A1 | 8/2015 | Johnson et al. |
| 2015/0230861 A1 | 8/2015 | Woloszko et al. |
| 2015/0257780 A1 | 9/2015 | Houser |
| 2015/0265262 A1* | 9/2015 | Dewaele ............ A61B 17/2909 606/1 |
| 2015/0265305 A1* | 9/2015 | Stulen ............ A61B 17/320068 606/169 |
| 2015/0272659 A1 | 10/2015 | Boudreaux et al. |
| 2015/0272660 A1 | 10/2015 | Boudreaux et al. |
| 2015/0289854 A1 | 10/2015 | Cho et al. |
| 2015/0340586 A1 | 11/2015 | Wiener et al. |
| 2016/0030076 A1 | 2/2016 | Faller et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058465 A1* | 3/2016 | Akagane ........ A61B 17/32009 606/169 |
| 2016/0058492 A1 | 3/2016 | Yates et al. |
| 2016/0074108 A1 | 3/2016 | Woodruff et al. |
| 2016/0114355 A1 | 4/2016 | Sakai et al. |
| 2016/0121143 A1 | 5/2016 | Mumaw et al. |
| 2016/0128762 A1 | 5/2016 | Harris et al. |
| 2016/0128769 A1 | 5/2016 | Rontal et al. |
| 2016/0144204 A1 | 5/2016 | Akagane |
| 2016/0157927 A1 | 6/2016 | Corbett et al. |
| 2016/0174969 A1 | 6/2016 | Kerr et al. |
| 2016/0175024 A1 | 6/2016 | Yates et al. |
| 2016/0175029 A1 | 6/2016 | Witt et al. |
| 2016/0175032 A1 | 6/2016 | Yang |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0228171 A1 | 8/2016 | Boudreaux |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0317217 A1 | 11/2016 | Batross et al. |
| 2016/0338726 A1 | 11/2016 | Stulen et al. |
| 2016/0346001 A1 | 12/2016 | Vakharia et al. |
| 2016/0367273 A1 | 12/2016 | Robertson et al. |
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2017/0000512 A1 | 1/2017 | Conlon et al. |
| 2017/0000541 A1 | 1/2017 | Yates et al. |
| 2017/0014152 A1 | 1/2017 | Noui et al. |
| 2017/0056056 A1 | 3/2017 | Wiener et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0090507 A1 | 3/2017 | Wiener et al. |
| 2017/0095267 A1 | 4/2017 | Messerly et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0143371 A1 | 5/2017 | Witt et al. |
| 2017/0143877 A1 | 5/2017 | Witt et al. |
| 2017/0164972 A1 | 6/2017 | Johnson et al. |
| 2017/0172700 A1 | 6/2017 | Denzinger et al. |
| 2017/0189095 A1 | 7/2017 | Danziger et al. |
| 2017/0189096 A1 | 7/2017 | Danziger et al. |
| 2017/0189101 A1 | 7/2017 | Yates et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |

(56) References Cited

U.S. PATENT DOCUMENTS

| | | |
|---|---|---|
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014846 A1 | 1/2018 | Rhee et al. |
| 2018/0042634 A1 | 2/2018 | Conlon et al. |
| 2018/0049767 A1 | 2/2018 | Gee et al. |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055533 A1 | 3/2018 | Conlon et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0199957 A1 | 7/2018 | Robertson et al. |
| 2018/0206881 A1 | 7/2018 | Price et al. |
| 2018/0221049 A1 | 8/2018 | Faller et al. |
| 2018/0263653 A1 | 9/2018 | Witt et al. |
| 2018/0289389 A1 | 10/2018 | Witt et al. |
| 2019/0008543 A1 | 1/2019 | Scoggins et al. |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101396300 A | 4/2009 |
| CN | 101467917 A | 7/2009 |
| CN | 101674782 A | 3/2010 |
| CN | 101883531 A | 11/2010 |
| CN | 102160045 A | 8/2011 |
| CN | 202027624 U | 11/2011 |
| CN | 102834069 A | 12/2012 |
| CN | 101313865 B | 1/2013 |
| DE | 3904558 A1 | 8/1990 |
| DE | 9210327 U1 | 11/1992 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0342448 A1 | 11/1989 |
| EP | 0443256 A1 | 8/1991 |
| EP | 0456470 A1 | 11/1991 |
| EP | 0238667 B1 | 2/1993 |
| EP | 0340803 B1 | 8/1993 |
| EP | 0598976 A2 | 6/1994 |
| EP | 0630612 A1 | 12/1994 |
| EP | 0424685 B1 | 5/1995 |
| EP | 0677275 A2 | 10/1995 |
| EP | 0482195 B1 | 1/1996 |
| EP | 0695535 A1 | 2/1996 |
| EP | 0705571 A1 | 4/1996 |
| EP | 0741996 B1 | 11/1996 |
| EP | 0612570 B1 | 6/1997 |
| EP | 0557806 B1 | 5/1998 |
| EP | 0640317 B1 | 9/1999 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 0722696 B1 | 12/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1293172 B1 | 4/2006 |
| EP | 0875209 B1 | 5/2006 |
| EP | 1433425 B1 | 6/2006 |
| EP | 1256323 B1 | 8/2006 |
| EP | 1698289 A2 | 9/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1815950 A1 | 8/2007 |
| EP | 1839599 A1 | 10/2007 |
| EP | 1844720 A1 | 10/2007 |
| EP | 1862133 A1 | 12/2007 |
| EP | 1875875 A1 | 1/2008 |
| EP | 1878399 A1 | 1/2008 |
| EP | 1915953 A1 | 4/2008 |
| EP | 1532933 B1 | 5/2008 |
| EP | 1199045 B1 | 6/2008 |
| EP | 1707143 B1 | 6/2008 |
| EP | 1943957 A2 | 7/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1477104 B1 | 1/2009 |
| EP | 2014218 A2 | 1/2009 |
| EP | 1849424 B1 | 4/2009 |
| EP | 2042112 A2 | 4/2009 |
| EP | 2042117 A1 | 4/2009 |
| EP | 2060238 A1 | 5/2009 |
| EP | 1832259 B1 | 6/2009 |
| EP | 2074959 A1 | 7/2009 |
| EP | 1810625 B1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 1769766 B1 | 2/2010 |
| EP | 2151204 A1 | 2/2010 |
| EP | 2153791 A1 | 2/2010 |
| EP | 2200145 A1 | 6/2010 |
| EP | 1214913 B1 | 7/2010 |
| EP | 2238938 A1 | 10/2010 |
| EP | 2243439 A1 | 10/2010 |
| EP | 2298154 A2 | 3/2011 |
| EP | 2305144 A1 | 4/2011 |
| EP | 1510178 B1 | 6/2011 |
| EP | 1946708 B1 | 6/2011 |
| EP | 2335630 A1 | 6/2011 |

(56) References Cited

FOREIGN PATENT DOCUMENTS

| | | |
|---|---|---|
| EP | 1502551 B1 | 7/2011 |
| EP | 1728475 B1 | 8/2011 |
| EP | 2353518 A1 | 8/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2529681 A1 | 12/2012 |
| EP | 1767164 B1 | 1/2013 |
| EP | 2316359 B1 | 3/2013 |
| EP | 2090238 B1 | 4/2013 |
| EP | 2578172 A2 | 4/2013 |
| EP | 1586275 B1 | 5/2013 |
| EP | 1616529 B1 | 9/2013 |
| EP | 1997438 B1 | 11/2013 |
| EP | 2508143 B1 | 2/2014 |
| EP | 2583633 B1 | 10/2014 |
| EP | 2113210 B1 | 3/2016 |
| EP | 2510891 B1 | 6/2016 |
| EP | 2227155 B1 | 7/2016 |
| EP | 2859858 B1 | 12/2016 |
| ES | 2115068 T3 | 6/1998 |
| FR | 2964554 A1 | 3/2012 |
| GB | 1482943 A | 8/1977 |
| GB | 2032221 A | 4/1980 |
| GB | 2317566 A | 4/1998 |
| GB | 2318298 A | 4/1998 |
| GB | 2379878 B | 11/2004 |
| GB | 2425480 A | 11/2006 |
| GB | 2472216 A | 2/2011 |
| GB | 2447767 B | 8/2011 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04150847 A | 5/1992 |
| JP | H04152942 A | 5/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H06217988 A | 8/1994 |
| JP | H06507081 A | 8/1994 |
| JP | H 07500514 A | 1/1995 |
| JP | H07508910 A | 10/1995 |
| JP | H07308323 A | 11/1995 |
| JP | H0824266 A | 1/1996 |
| JP | H08229050 A | 9/1996 |
| JP | H08275951 A | 10/1996 |
| JP | H08299351 A | 11/1996 |
| JP | H08336544 A | 12/1996 |
| JP | H08336545 A | 12/1996 |
| JP | H09503146 A | 3/1997 |
| JP | H09135553 A | 5/1997 |
| JP | H09140722 A | 6/1997 |
| JP | H105237 A | 1/1998 |
| JP | H10295700 A | 11/1998 |
| JP | H11501543 A | 2/1999 |
| JP | H11128238 A | 5/1999 |
| JP | H11192235 A | 7/1999 |
| JP | H11253451 A | 9/1999 |
| JP | H11318918 A | 11/1999 |
| JP | 2000041991 A | 2/2000 |
| JP | 2000070279 A | 3/2000 |
| JP | 2000210299 A | 8/2000 |
| JP | 2000271145 A | 10/2000 |
| JP | 2000287987 A | 10/2000 |
| JP | 2001029353 A | 2/2001 |
| JP | 2001502216 A | 2/2001 |
| JP | 2001309925 A | 11/2001 |
| JP | 2002177295 A | 6/2002 |
| JP | 2002186901 A | 7/2002 |
| JP | 2002204808 A | 7/2002 |
| JP | 2002238919 A | 8/2002 |
| JP | 2002263579 A | 9/2002 |
| JP | 2002301086 A | 10/2002 |
| JP | 2002306504 A | 10/2002 |
| JP | 2002330977 A | 11/2002 |
| JP | 2002542690 A | 12/2002 |
| JP | 2003000612 A | 1/2003 |
| JP | 2003010201 A | 1/2003 |
| JP | 2003510158 A | 3/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003530921 A | 10/2003 |
| JP | 2003310627 A | 11/2003 |
| JP | 2003339730 A | 12/2003 |
| JP | 2004129871 A | 4/2004 |
| JP | 2004147701 A | 5/2004 |
| JP | 2005027026 A | 1/2005 |
| JP | 2005040222 A | 2/2005 |
| JP | 2005066316 A | 3/2005 |
| JP | 2005074088 A | 3/2005 |
| JP | 2005507679 A | 3/2005 |
| JP | 2005094552 A | 4/2005 |
| JP | 2005253674 A | 9/2005 |
| JP | 2005534451 A | 11/2005 |
| JP | 2006006410 A | 1/2006 |
| JP | 2006512149 A | 4/2006 |
| JP | 2006116194 A | 5/2006 |
| JP | 2006158525 A | 6/2006 |
| JP | 2006217716 A | 8/2006 |
| JP | 2006218296 A | 8/2006 |
| JP | 2006288431 A | 10/2006 |
| JP | 2007050181 A | 3/2007 |
| JP | 2007-524459 A | 8/2007 |
| JP | 2007229454 A | 9/2007 |
| JP | 2007527747 A | 10/2007 |
| JP | 2007296369 A | 11/2007 |
| JP | 2008018226 A | 1/2008 |
| JP | 2008036390 A | 2/2008 |
| JP | 2008508065 A | 3/2008 |
| JP | 2008119250 A | 5/2008 |
| JP | 2008515562 A | 5/2008 |
| JP | 2008521503 A | 6/2008 |
| JP | D1339835 S | 8/2008 |
| JP | 2008212679 A | 9/2008 |
| JP | 2008536562 A | 9/2008 |
| JP | 2008284374 A | 11/2008 |
| JP | 2009511206 A | 3/2009 |
| JP | 2009082711 A | 4/2009 |
| JP | 2009517181 A | 4/2009 |
| JP | 4262923 B2 | 5/2009 |
| JP | 2009523567 A | 6/2009 |
| JP | 2009148557 A | 7/2009 |
| JP | 2009236177 A | 10/2009 |
| JP | 2009254819 A | 11/2009 |
| JP | 2009297352 A | 12/2009 |
| JP | 2010000336 A | 1/2010 |
| JP | 2010009686 A | 1/2010 |
| JP | 2010514923 A | 5/2010 |
| JP | 2010121865 A | 6/2010 |
| JP | 2010534522 A | 11/2010 |
| JP | 2010540186 A | 12/2010 |
| JP | 2011505198 A | 2/2011 |
| JP | 2011160586 A | 8/2011 |

(56) References Cited

FOREIGN PATENT DOCUMENTS

| | | |
|---|---|---|
| JP | 2012/075899 A | 4/2012 |
| JP | 2012235658 A | 11/2012 |
| JP | 5208761 B2 | 6/2013 |
| JP | 5714508 B2 | 5/2015 |
| JP | 2015515339 A | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2304934 C2 | 8/2007 |
| RU | 2405603 C1 | 12/2010 |
| SU | 850068 A1 | 7/1981 |
| WO | WO-8103272 A1 | 11/1981 |
| WO | WO-9222259 A2 | 12/1992 |
| WO | WO-9307817 A1 | 4/1993 |
| WO | WO-9308757 A1 | 5/1993 |
| WO | WO-9314708 A1 | 8/1993 |
| WO | WO-9316646 A1 | 9/1993 |
| WO | WO-9320877 A1 | 10/1993 |
| WO | WO-9322973 A1 | 11/1993 |
| WO | WO-9400059 A1 | 1/1994 |
| WO | WO-9421183 A1 | 9/1994 |
| WO | WO-9424949 A1 | 11/1994 |
| WO | WO-9509572 A1 | 4/1995 |
| WO | WO-9510978 A1 | 4/1995 |
| WO | WO-9534259 A1 | 12/1995 |
| WO | WO-9630885 A1 | 10/1996 |
| WO | WO-9635382 A1 | 11/1996 |
| WO | WO-9639086 A1 | 12/1996 |
| WO | WO-9710764 A1 | 3/1997 |
| WO | WO-9800069 A1 | 1/1998 |
| WO | WO-9816156 A1 | 4/1998 |
| WO | WO-9826739 A1 | 6/1998 |
| WO | WO-9835621 A1 | 8/1998 |
| WO | WO-9837815 A1 | 9/1998 |
| WO | WO-9840020 A1 | 9/1998 |
| WO | WO-9847436 A1 | 10/1998 |
| WO | WO-9857588 A1 | 12/1998 |
| WO | WO-9920213 A1 | 4/1999 |
| WO | WO-9923960 A1 | 5/1999 |
| WO | WO-9940857 A1 | 8/1999 |
| WO | WO-9940861 A1 | 8/1999 |
| WO | WO-9952489 A1 | 10/1999 |
| WO | WO-0024330 A1 | 5/2000 |
| WO | WO-0024331 A1 | 5/2000 |
| WO | WO-0025691 A1 | 5/2000 |
| WO | WO-0064358 A2 | 11/2000 |
| WO | WO-0074585 A2 | 12/2000 |
| WO | WO-0124713 A1 | 4/2001 |
| WO | WO-0128444 A1 | 4/2001 |
| WO | WO-0154590 A1 | 8/2001 |
| WO | WO-0167970 A1 | 9/2001 |
| WO | WO-0195810 A2 | 12/2001 |
| WO | WO-0224080 A2 | 3/2002 |
| WO | WO-0238057 A1 | 5/2002 |
| WO | WO-02062241 A1 | 8/2002 |
| WO | WO-02080797 A1 | 10/2002 |
| WO | WO-03001986 A2 | 1/2003 |
| WO | WO-03013374 A1 | 2/2003 |
| WO | WO-03020339 A2 | 3/2003 |
| WO | WO-03028541 A2 | 4/2003 |
| WO | WO-03030708 A2 | 4/2003 |
| WO | WO-03068046 A2 | 8/2003 |
| WO | WO-03082133 A1 | 10/2003 |
| WO | WO-2004011037 A2 | 2/2004 |
| WO | WO-2004012615 A1 | 2/2004 |
| WO | WO-2004026104 A2 | 4/2004 |
| WO | WO-2004032754 A2 | 4/2004 |
| WO | WO-2004032762 A1 | 4/2004 |
| WO | WO-2004032763 A2 | 4/2004 |
| WO | WO-2004037095 A2 | 5/2004 |
| WO | WO-2004060141 A2 | 7/2004 |
| WO | WO-2004078051 A2 | 9/2004 |
| WO | WO-2004098426 A1 | 11/2004 |
| WO | WO-2004112618 A2 | 12/2004 |
| WO | WO-2005052959 A2 | 6/2005 |
| WO | WO-2005117735 A1 | 12/2005 |
| WO | WO-2005122917 A1 | 12/2005 |
| WO | WO-2006012797 A1 | 2/2006 |
| WO | WO-2006021269 A1 | 3/2006 |
| WO | WO-2006036706 A1 | 4/2006 |
| WO | WO-2006042210 A2 | 4/2006 |
| WO | WO-2006055166 A2 | 5/2006 |
| WO | WO-2006058223 A2 | 6/2006 |
| WO | WO-2006063199 A2 | 6/2006 |
| WO | WO-2006083988 A1 | 8/2006 |
| WO | WO-2006101661 A2 | 9/2006 |
| WO | WO-2006119139 A2 | 11/2006 |
| WO | WO-2006119376 A2 | 11/2006 |
| WO | WO-2006129465 A1 | 12/2006 |
| WO | WO-2007008703 A2 | 1/2007 |
| WO | WO-2007008710 A2 | 1/2007 |
| WO | WO-2007038538 A1 | 4/2007 |
| WO | WO-2007040818 A1 | 4/2007 |
| WO | WO-2007047380 A2 | 4/2007 |
| WO | WO-2007047531 A2 | 4/2007 |
| WO | WO-2007056590 A1 | 5/2007 |
| WO | WO-2007087272 A2 | 8/2007 |
| WO | WO-2007089724 A2 | 8/2007 |
| WO | WO-2007143665 A2 | 12/2007 |
| WO | WO-2008016886 A2 | 2/2008 |
| WO | WO-2008020964 A2 | 2/2008 |
| WO | WO-2008042021 A1 | 4/2008 |
| WO | WO-2008045348 A2 | 4/2008 |
| WO | WO-2008049084 A2 | 4/2008 |
| WO | WO-2008051764 A2 | 5/2008 |
| WO | WO-2008089174 A2 | 7/2008 |
| WO | WO-2008099529 A1 | 8/2008 |
| WO | WO-2008101356 A1 | 8/2008 |
| WO | WO-2008118709 A1 | 10/2008 |
| WO | WO-2008130793 A1 | 10/2008 |
| WO | WO-2009010565 A1 | 1/2009 |
| WO | WO-2009018067 A2 | 2/2009 |
| WO | WO-2009018406 A2 | 2/2009 |
| WO | WO-2009022614 A1 | 2/2009 |
| WO | WO-2009027065 A1 | 3/2009 |
| WO | WO-2009036818 A1 | 3/2009 |
| WO | WO-2009039179 A1 | 3/2009 |
| WO | WO-2009046234 A2 | 4/2009 |
| WO | WO-2009059741 A1 | 5/2009 |
| WO | WO-2009073402 A2 | 6/2009 |
| WO | WO-2009082477 A2 | 7/2009 |
| WO | WO-2009088550 A2 | 7/2009 |
| WO | WO-2009120992 A2 | 10/2009 |
| WO | WO-2009141616 A1 | 11/2009 |
| WO | WO-2009149234 A1 | 12/2009 |
| WO | WO-2010017149 A2 | 2/2010 |
| WO | WO-2010017266 A1 | 2/2010 |
| WO | WO-2010068783 A1 | 6/2010 |
| WO | WO-2010104755 A1 | 9/2010 |
| WO | WO-2011008672 A2 | 1/2011 |
| WO | WO-2011/044338 A2 | 4/2011 |
| WO | WO-2011052939 A2 | 5/2011 |
| WO | WO-2011060031 A1 | 5/2011 |
| WO | WO-2011084768 A1 | 7/2011 |
| WO | WO-2011089717 A1 | 7/2011 |
| WO | WO-2011100321 A2 | 8/2011 |
| WO | WO-2011144911 A1 | 11/2011 |
| WO | WO-2012044597 A2 | 4/2012 |
| WO | WO-2012044606 A2 | 4/2012 |
| WO | WO-2012061722 A2 | 5/2012 |
| WO | WO-2012066983 A1 | 5/2012 |
| WO | WO-2012128362 A1 | 9/2012 |
| WO | WO-2012135705 A1 | 10/2012 |
| WO | WO-2012135721 A1 | 10/2012 |
| WO | WO-2012166510 A1 | 12/2012 |
| WO | WO-2013018934 A1 | 2/2013 |
| WO | WO-2013034629 A1 | 3/2013 |
| WO | WO-2013048963 A2 | 4/2013 |
| WO | WO-2013062978 A2 | 5/2013 |
| WO | WO-2013102602 A2 | 7/2013 |
| WO | WO-2013154157 A1 | 10/2013 |

(56) References Cited

FOREIGN PATENT DOCUMENTS

| WO | WO-2014092108 A1 | 6/2014 |
|---|---|---|
| WO | WO-2015197395 A8 | 12/2015 |
| WO | WO-2016009921 A1 | 1/2016 |

OTHER PUBLICATIONS

Jang, J. et al. "Neuro-fuzzy and Soft Computing." Prentice Hall, 1997, pp. 13-89, 199-293, 335-393, 453-496, 535-549.
Leonard I. Malis, M.D., "The Value of Irrigation During Bipolar Coagulation," 1989.
http://www.4-traders.com/JOHNSON-JOHNSON-4832/news/Johnson-Johnson-Ethicon-E . . . .
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Technology Overview, printed from www.harmonicscalpel.com, Internet site, website accessed on Jun. 13, 2007, (3 pages).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Chen et al., "Heat-induced changes in the mechanics of a collagenous tissue: pseudoelastic behavior at 37° C.," Journal of Biomechanics, 31, pp. 211-216 (1998).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Covidien 501(k) Summary Sonicision, dated Feb. 24, 2011 (7 pages).
http://www.valleylab.com/product/es/generators/index.html.
http://www.megadyne.com/es_generator.php.
http://www.medicalexpo.com/medical-manufacturer/electrosurgical-generator-6951.html.
http:/www.ethicon.com/gb-en/healthcare-professionals/products/energy-devices/capital//ge . . . .
http://www.dotmed.com/listing/electrosurical-unit/ethicon/ultracision-g110-/1466724.
http://www.apicalinstr.com/generators.htm.
Walsh, S. J., White, R. G., "Vibrational Power Transmission in Curved Beams," Journal of Sound and Vibration, 233(3), 455-488 (2000).
Morley, L. S. D., "Elastic Waves in a Naturally Curved Rod," Quarterly Journal of Mechanics and Applied Mathematics, 14: 155-172 (1961).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Graff, K.F., "Elastic Wave Propagation in a Curved Sonic Transmission Line," IEEE Transactions on Sonics and Ultrasonics, SU-17(1), 1-6 (1970).
Campbell et al, "Thermal Imaging in Surgery," p. 19-3, in Medical Infrared Imaging, N. A. Diakides and J. D. Bronzino, Eds. (2008).
F. A. Duck, "Optical Properties of Tissue Including Ultraviolet and Infrared Radiation," pp. 43-71 in Physical Properties of Tissue (1990).
Lim et al., "A Review of Mechanism Used in Laparoscopic Surgical Instruments," Mechanism and Machine Theory, vol. 38, pp. 1133-1147, (2003).
AST Products, Inc., "Principles of Video Contact Angle Analysis," 20 pages, (2006).
Wall et al., "Thermal modification of collagen," J Shoulder Elbow Surg, No. 8, pp. 339-344 (Jul./Aug. 1999).
Covidien Brochure, [Value Analysis Brief], LigaSure Advance™ Pistol Grip, dated Rev. Apr. 2010 (7 pages).
Kurt Gieck & Reiner Gieck, Engineering Formulas § Z.7 (7th ed. 1997).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
National Semiconductors Temperature Sensor Handbook—http://www.national.com/appinfo/tempsensors/files/temphb.pdf; accessed online: Apr. 1, 2011.
Sullivan, "Optimal Choice for Number of Strands in a Litz-Wire Transformer Winding," IEEE Transactions on Power Electronics, vol. 14, No. 2, Mar. 1999, pp. 283-291.
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www. erbe-med. com/erbe/media/Marketing materialien/85140170 ERBE EN VIO 200 S D027541.
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Wright, et al., "Time-Temperature Equivalence of Heat-Induced Changes in Cells and Proteins," Feb. 1998. ASME Journal of Biomechanical Engineering, vol. 120, pp. 22-26.
Humphrey, J.D., "Continuum Thermomechanics and the Clinical Treatment of Disease and Injury," Appl. Mech. Rev., vol. 56, No. 2 pp. 231-260 (Mar. 2003).
Gibson, "Magnetic Refrigerator Successfully Tested," U.S. Department of Energy Research News, accessed online on Aug. 6, 2010 at http://www.eurekalet.org/features/doe/2001-11/dl-mrs062802.php (Nov. 1, 2001).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Moran et al., "Thermally Induced Shrinkage of Joint Capsule," Clinical Orthopaedics and Related Research, No. 281, pp. 248-255 (Dec. 2000).

(56) References Cited

OTHER PUBLICATIONS

Lee et al., "A multi-sample denaturation temperature tester for collagenous biomaterials," Med. Eng. Phy., vol. 17, No. 2, pp. 115-121 (Mar. 1995).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Chen et al., "Heat-Induced Changes in the Mechanics of a Collagenous Tissue: Isothermal Free Shrinkage," Transactions of the ASME, vol. 119, pp. 372-378 (Nov. 1997).
Glaser and Subak-Sharpe, lntegrated Circuit Engineering, Addison-Wesley Publishing, Reading, MA (1979). (book—not attached).
Incropera et al., Fundamentals of Heat and Mass Transfer, Wiley, New York (1990). (Book—not attached).

\* cited by examiner

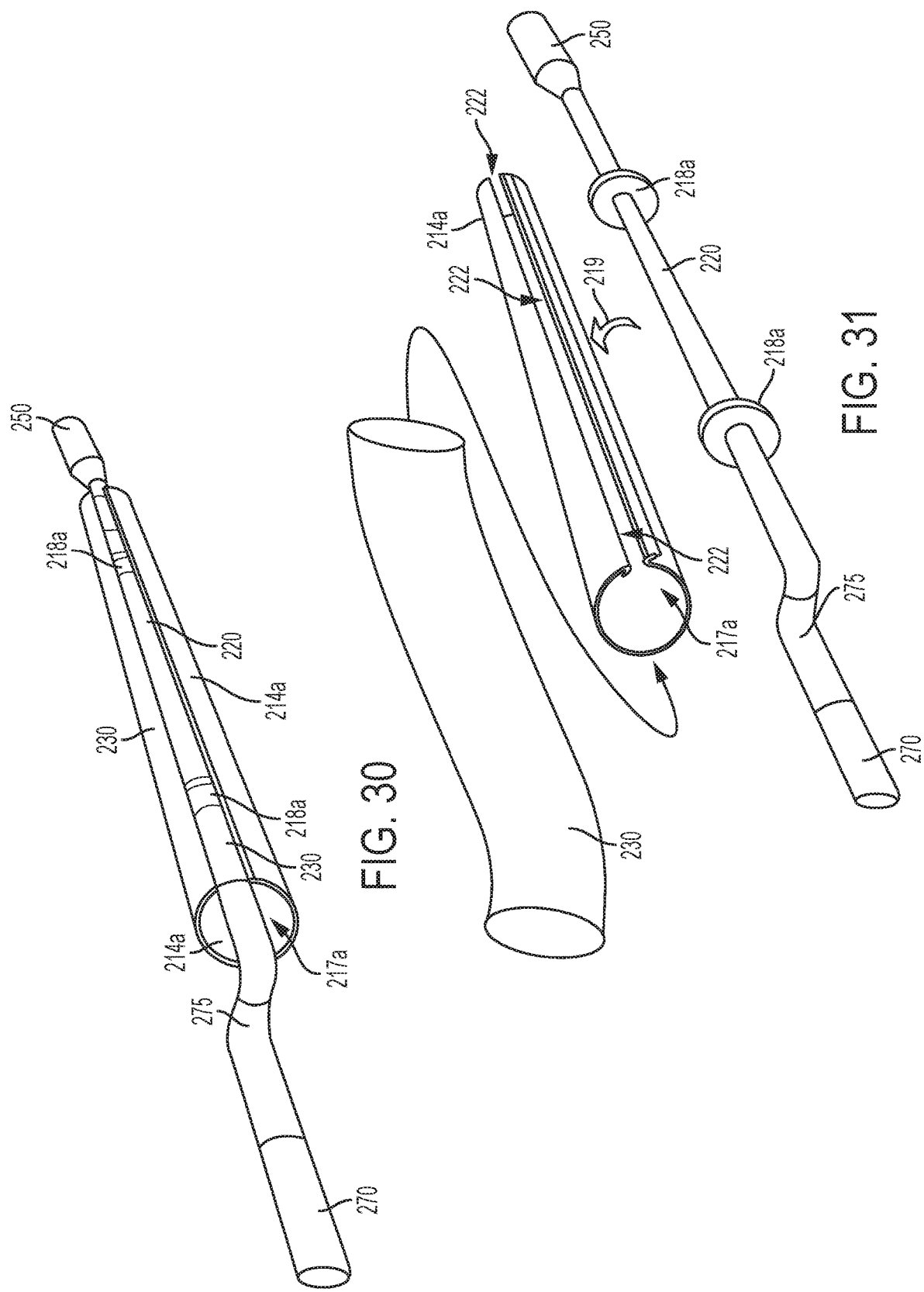

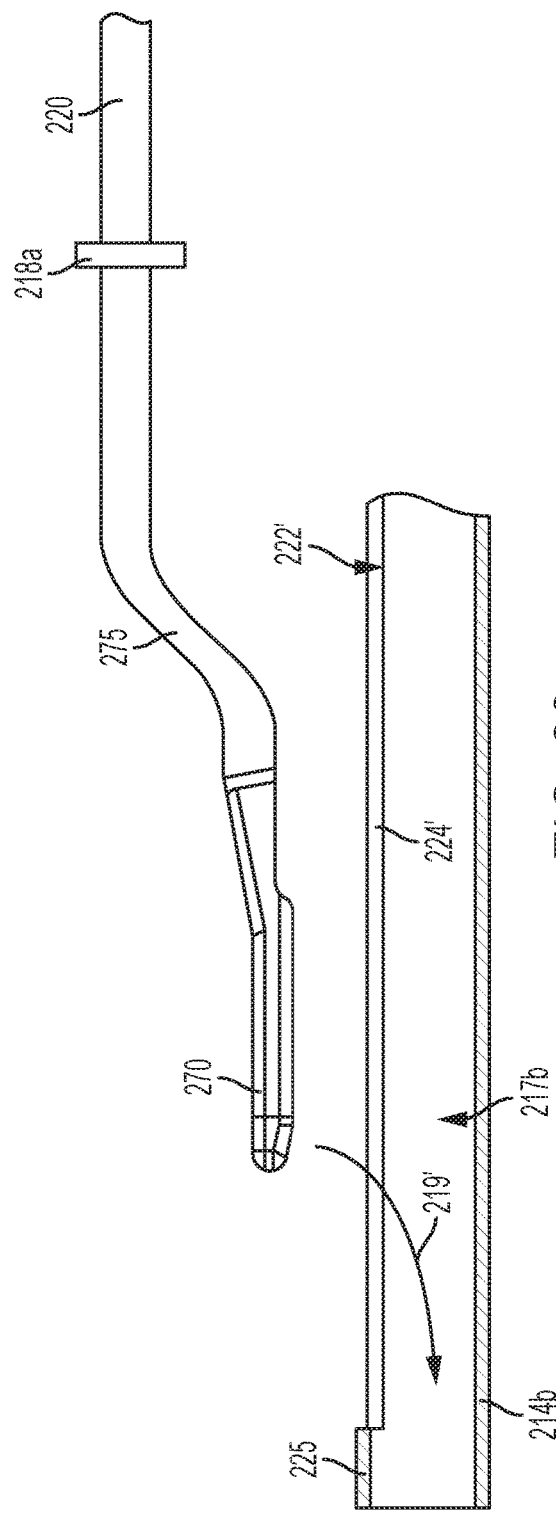
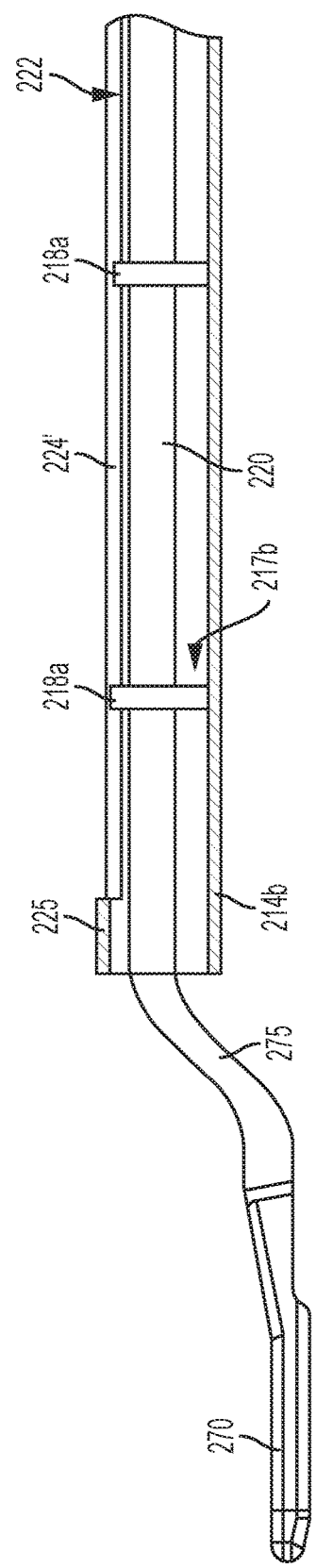

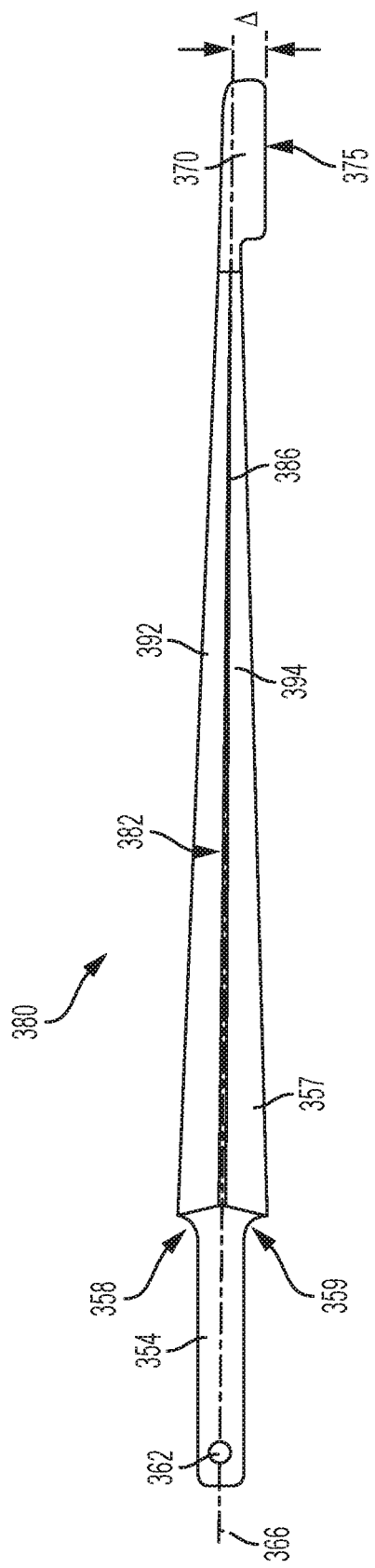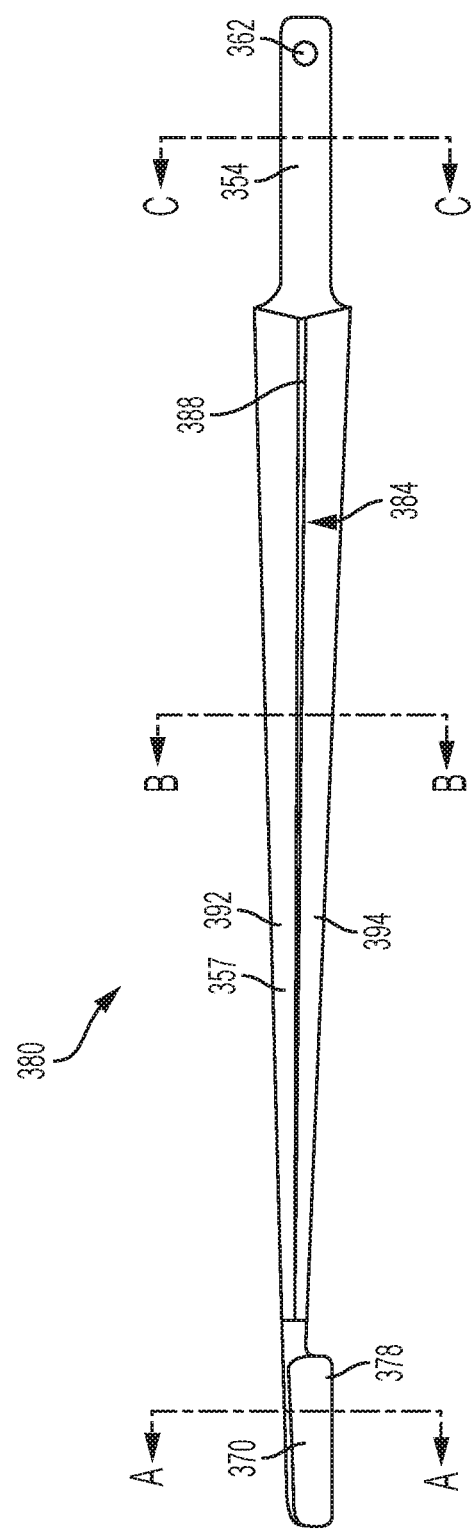
FIG. 55
FIG. 56

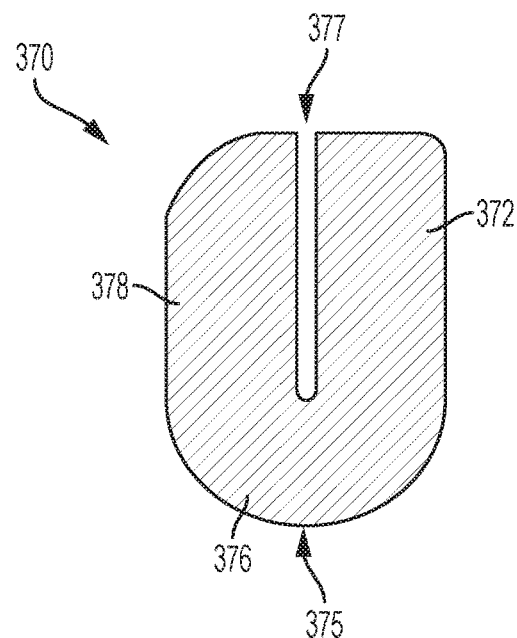
FIG. 57A
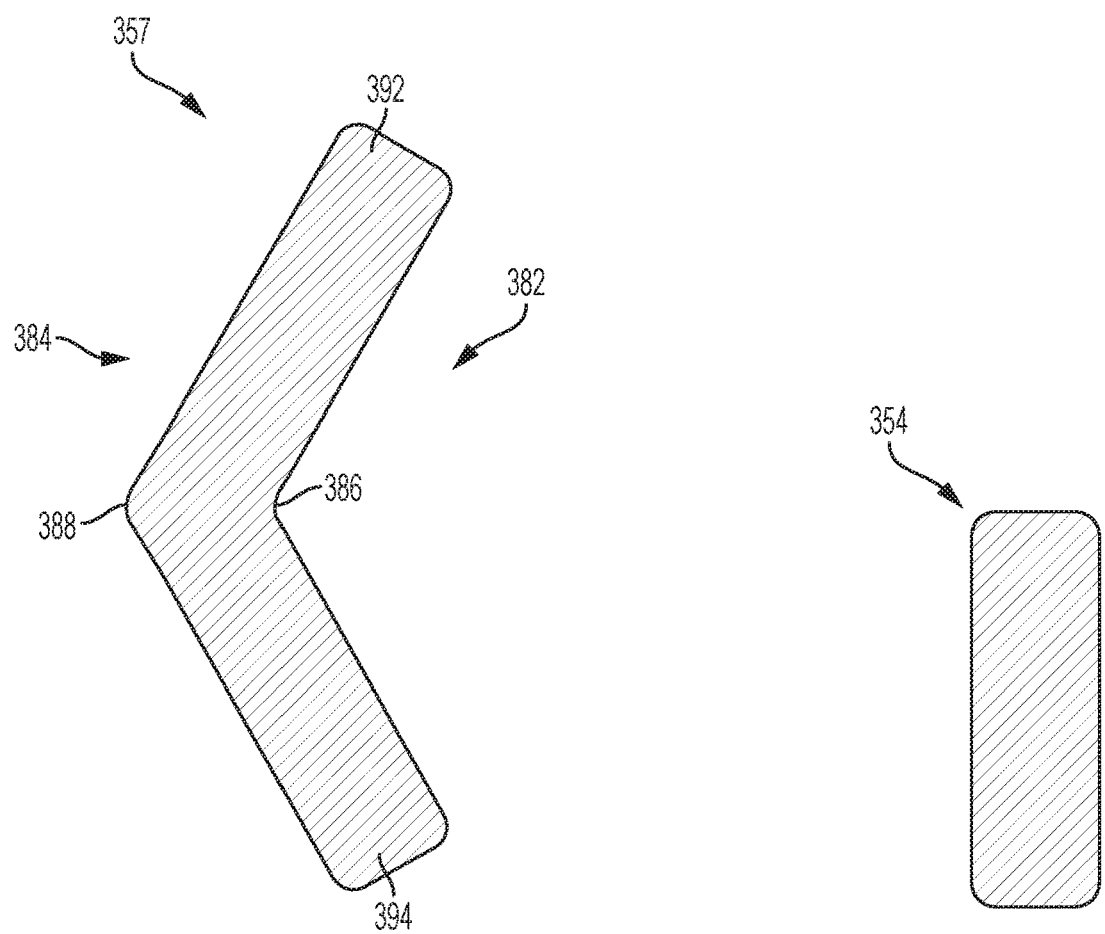
FIG. 57B
FIG. 57C

ULTRASONIC SURGICAL INSTRUMENTS HAVING OFFSET BLADES

BACKGROUND

Ultrasonic surgical instruments may be used to cut and/or coagulate biological tissue using energy in the form of mechanical vibrations transmitted to a surgical end-effector (comprising a cutting blade, for example) at ultrasonic frequencies (e.g., 55.5 kilohertz). Activating an end-effector at ultrasonic frequencies induces rapid longitudinal vibratory movement that generates localized heat within contacting tissue, which denatures protein in the tissue, locally disrupts intercellular cohesion, and forms a sticky coagulum. Pressure exerted on tissue surfaces with the blade of an ultrasonic surgical instrument collapses blood vessels and allows the coagulum to form a hemostatic seal.

The ultrasonic mechanical vibrations, when transmitted to biological tissue at suitable energy levels and using a suitable end-effector, may effectively and efficiently cut, dissect, and/or coagulate tissue in an accurate and precise manner. Thus, ultrasonic surgical instruments can minimize patient trauma during surgical procedures by facilitating substantially simultaneous cutting of tissue and hemostatic coagulation. Accordingly, ultrasonic surgical instruments are used by clinicians to perform various surgical procedures, including open (invasive), laparoscopic, endoscopic, and robotic-assisted surgical procedures.

Although ultrasonic surgical instruments have gained wide acceptance among surgeons and other clinicians, some areas of improvement still remain. For example, ultrasonic surgical instruments that facilitate increased surgical site access, visibility, and manipulability would be advantageous. Additionally, ultrasonic surgical instruments with decreased manufacturing costs would be advantageous.

SUMMARY

The invention described in this specification generally relates to ultrasonic surgical instruments. More specifically, the invention comprises ultrasonic surgical instruments having offset blade configurations, which provide for increased surgical site access and visibility to surgeons. The invention also comprises ultrasonic surgical instruments having blades that may be fabricated from sheet metal stock, which decreases manufacturing cost. The invention further comprises ultrasonic surgical blades and end-effectors configured for use with ultrasonic surgical instruments, and related assemblies and systems.

In one example, an ultrasonic surgical instrument comprises an ultrasonic transducer having a central transducer axis, an acoustic horn acoustically coupled to the ultrasonic transducer, and an ultrasonic transmission waveguide acoustically coupled to the acoustic horn. The ultrasonic transmission waveguide comprises a curved portion and a linear portion. An ultrasonic surgical blade is acoustically coupled to the ultrasonic transmission waveguide. The linear portion of the ultrasonic transmission waveguide and the ultrasonic surgical blade are angularly off-set from the central transducer axis.

In another example, an ultrasonic surgical instrument comprises an ultrasonic transducer, an acoustic horn acoustically coupled to the ultrasonic transducer, and an ultrasonic transmission waveguide acoustically coupled to the acoustic horn. The ultrasonic transmission waveguide has a central waveguide axis. An ultrasonic surgical blade is acoustically coupled to the ultrasonic transmission waveguide through a compound curvature component. The compound curvature component transversely off-sets the ultrasonic surgical blade from the central waveguide axis.

In another example, an ultrasonic surgical instrument comprises an ultrasonic transducer, an ultrasonic transmission waveguide acoustically coupled to the ultrasonic transducer, and an ultrasonic surgical blade integrally formed with the ultrasonic transmission waveguide. The ultrasonic transmission waveguide has a tapered width that decreases from a maximum at the acoustic coupling with the ultrasonic transducer to a minimum at a transition to the ultrasonic surgical blade.

It is understood that the invention described in this specification is not necessarily limited to the examples summarized in this Summary.

BRIEF DESCRIPTION OF THE DRAWINGS

Various features and characteristics of the invention described in this specification may be better understood by reference to the accompanying figures, in which:

FIG. 30 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath;

FIG. 31 is an exploded perspective view schematic diagram of the assembly shown in FIG. 30;

FIG. 33 is a side view schematic diagram, partially in cross-section, of an ultrasonic surgical blade, ultrasonic transmission waveguide, and sheath assembly, in a disassembled configuration, showing the positioning of the ultrasonic surgical blade into the sheath, wherein the ultrasonic surgical blade is transversely off-set from the ultrasonic transmission waveguide through a compound curvature component connecting the ultrasonic surgical blade to the ultrasonic transmission waveguide, and wherein the sheath comprises a slot forming an opening located along a portion of the sheath length;

FIG. 34 is a side view schematic diagram, partially in cross-section, showing the assembly illustrated in FIG. 33 in an assembled configuration;

FIG. 55 is a side view schematic diagram of the blade of the ultrasonic surgical instrument shown in FIGS. 43-46;

FIG. 56 is a side view schematic diagram of the blade of the ultrasonic surgical instrument shown in FIGS. 43-46;

FIG. 57A is a cross-sectional schematic diagram of the ultrasonic surgical blade shown in FIGS. 55 and 56 as viewed along line A-A in FIG. 56;

FIG. 57B is a cross-sectional schematic diagram of the ultrasonic surgical blade shown in FIGS. 55 and 56 as viewed along line B-B in FIG. 56; and FIG. 57C is a cross-sectional schematic diagram of the ultrasonic surgical blade shown in FIGS. 55 and 56 as viewed along line C-C in FIG. 56.

Figure 1:
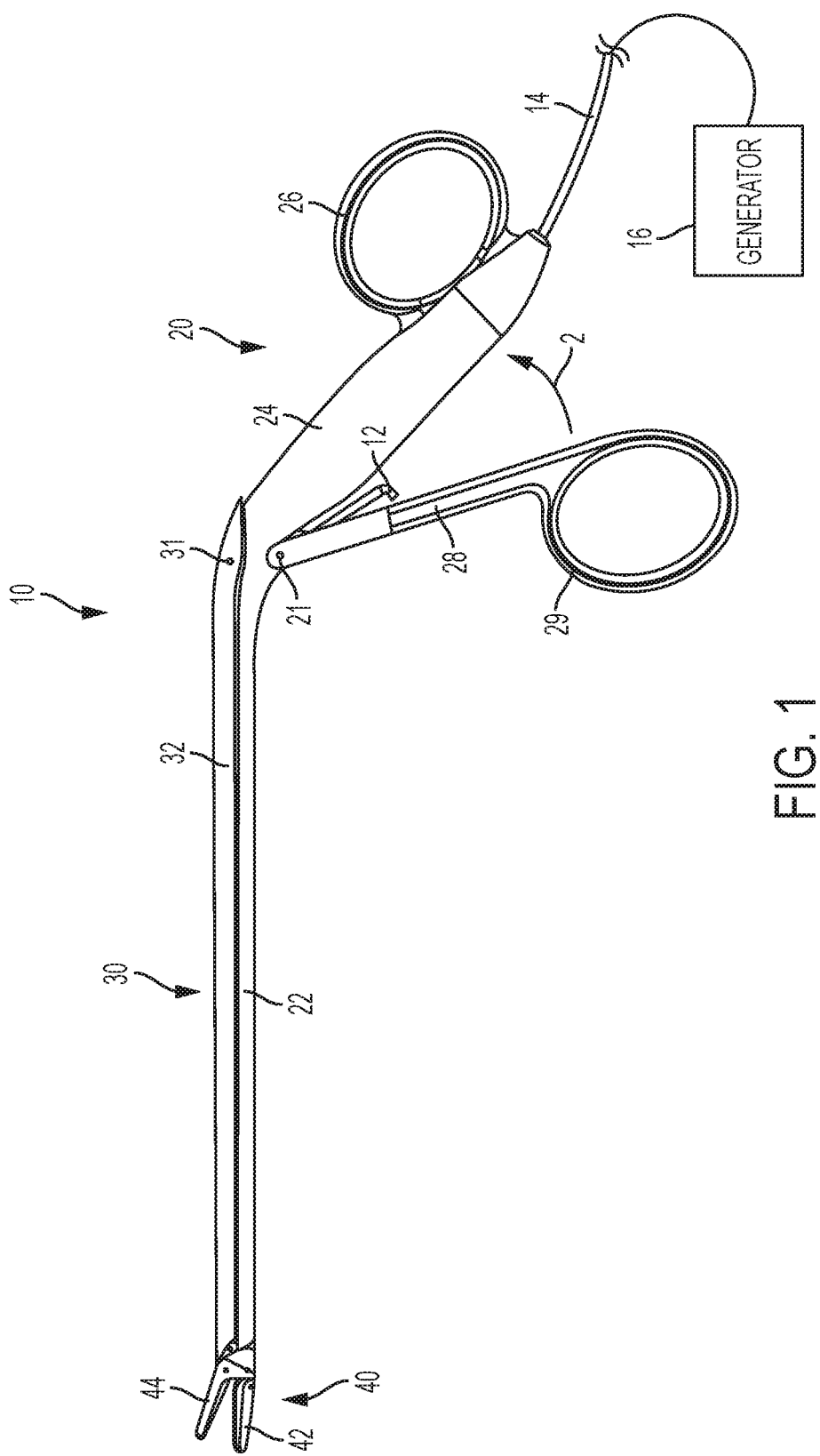
FIG. 1 is a side view of an ultrasonic surgical instrument having a tissue clamping mechanism, shown in an open position, with an angled scissor grip configuration and comprising an ultrasonic surgical blade that is angularly off-set from an ultrasonic transducer located within a handle assembly.
Figure 2:
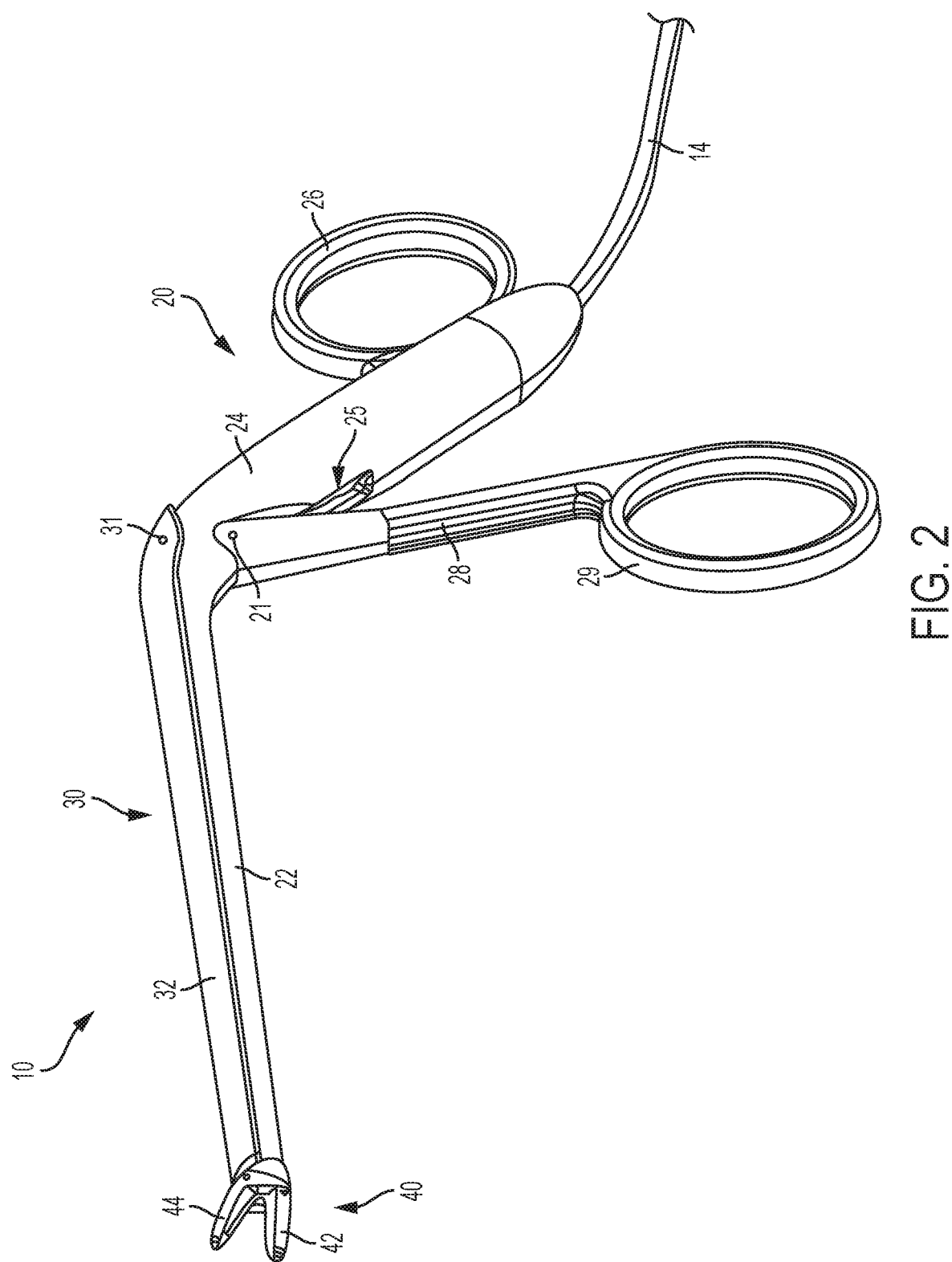
FIG. 2 is a front perspective view of the ultrasonic surgical instrument shown in FIG. 1.
Figure 3:
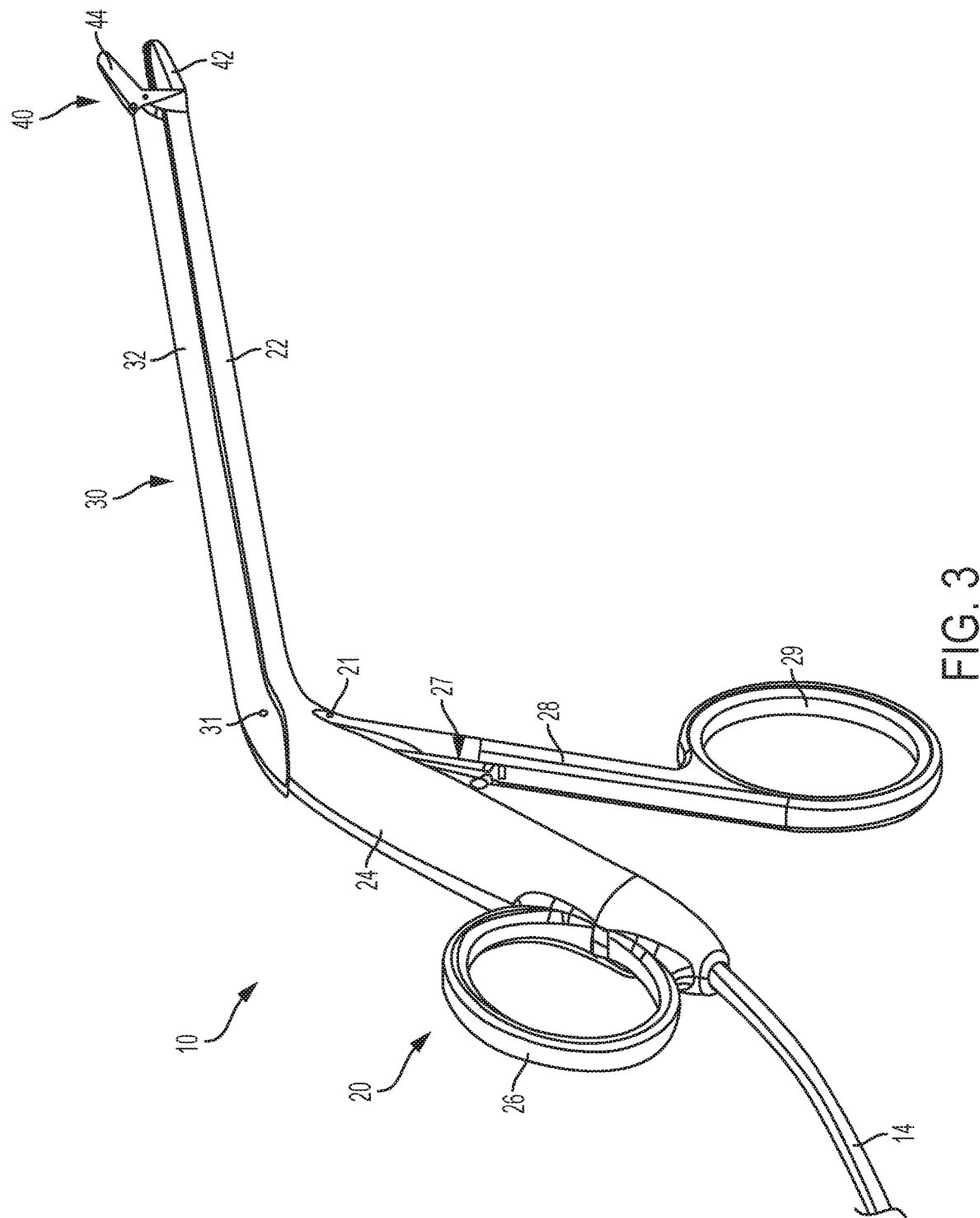
FIG. 3 is a rear perspective view of the ultrasonic surgical instrument shown in FIGS. 1 and 2.

The reader will appreciate the foregoing features and characteristics, as well as others, upon considering the following detailed description of the invention according to this specification.

DESCRIPTION

In this specification, including the claims, spatial terms (e.g., front, rear, back, top, bottom, upper, lower, vertical, horizontal, above, below, over, under, and the like), used to describe the relative orientation, location, or positioning of components, are used for clarity and convenience and are not to be construed as limited to any absolute frame of reference. Additionally, the terms "proximal" and "distal" (and grammatical variants such as "proximally" and "distally") are used in this specification with reference to a surgeon or other operator holding the handle portion of a surgical instrument comprising the feature or characteristic described as "proximal" or "distal," wherein the term "proximal" refers to the portion closest to the operator and the term "distal" refers to the portion located away from the operator. Also, where materials of construction are described for certain components is this specification, the components are not necessarily limited to the materials of construction so described, and other materials of construction may be used to implement the invention in practice.

Ultrasonic surgical instruments generally comprise an ultrasonic transducer acoustically coupled to an ultrasonic surgical blade through an ultrasonic transmission waveguide. In prior ultrasonic surgical instruments, the ultrasonic transducer, the ultrasonic transmission waveguide, and the ultrasonic surgical blade are co-axially aligned along a common longitudinal axis. Examples of such ultrasonic surgical instruments are described, for example, in the following documents, which are incorporated by reference into this specification.

U.S. Pat. No. 5,322,055, entitled "Clamp Coagulator/Cutting System for Ultrasonic Surgical Instruments," issued Jun. 21, 1994;

U.S. Pat. No. 5,873,873, entitled "Ultrasonic Clamp Coagulator Apparatus Having Improved Clamp Mechanism," issued Feb. 23, 1999

U.S. Pat. No. 5,980,510, entitled "Ultrasonic Clamp Coagulator Apparatus Having Improved Clamp Arm Pivot Mount," issued Nov. 9, 1999;

U.S. Pat. No. 6,325,811, entitled "Blades with Functional Balance Asymmetries for use with Ultrasonic Surgical Instruments," issued Dec. 4, 2001;

U.S. Pat. No. 6,773,444, entitled "Blades with Functional Balance Asymmetries for Use with Ultrasonic Surgical Instruments," issued Aug. 10, 2004;

U.S. Pat. No. 6,783,524, entitled "Robotic Surgical Tool with Ultrasound Cauterizing and Cutting Instrument," issued Aug. 31, 2004;

U.S. Publication No. 2006/0079874, entitled "Tissue Pad for Use with an Ultrasonic Surgical Instrument," published Apr. 13, 2006;

U.S. Publication No. 2007/0191713, entitled "Ultrasonic Device for Cutting and Coagulating," published Aug. 16, 2007;

U.S. Publication No. 2007/0282333, entitled "Ultrasonic Waveguide and Blade," published Dec. 6, 2007;

U.S. Publication No. 2008/0200940, entitled "Ultrasonic Device for Cutting and Coagulating," published Aug. 21, 2008;

U.S. Publication No. 2009/0105750, entitled "Ergonomic Surgical Instruments," published Apr. 23, 2009;

U.S. Publication No. 2010/0069940, entitled "Ultrasonic Device for Fingertip Control," published Mar. 18, 2010; and U.S. Publication No. 2011/0015660, entitled "Rotating Transducer Mount for Ultrasonic Surgical Instruments," published Jan. 20, 2011; and U.S. Publication No. 2012/0029546, entitled "Ultrasonic Surgical Instrument Blades," published Feb. 2, 2012.

U.S. Publication No. 2012/0112687, entitled "Recharge System for Medical Devices," published May 10, 2012;

U.S. Publication No. 2012/0116265, entitled "Surgical Instrument with Charging Devices," published May 10, 2012;

U.S. Publication No. 2014/0005701, entitled "Surgical Instruments with Articulating Shafts," published Jan. 2, 2014;

U.S. Publication No. 2014/0005704, entitled "Ultrasonic Surgical Instruments with Distally Positioned Jaw Assemblies," published Jan. 2, 2014;

U.S. Publication No. 2014/0114334, entitled "Flexible Harmonic Waveguides/Blades for Surgical Instruments," published Apr. 24, 2014;

U.S. Publication No. 2015/0148831, entitled "Handpiece and Blade Configurations for Ultrasonic Surgical Instrument," published May 28, 2015; and U.S. Publication No. 2016/0030076, entitled "Actuation Mechanism and Load Adjustment Assemblies for Surgical Instruments," published Feb. 4, 2016.

The ultrasonic surgical instruments described in this specification comprise angularly and/or transversely (linearly) off-set ultrasonic surgical blades. Referring to FIGS. 1-11, an ultrasonic surgical instrument 10 has tissue clamping functionality and an angled scissor grip configuration. The ultrasonic surgical instrument 10 comprises a handle assembly 20, a shaft assembly 30 connected to the handle assembly 20, and an end-effector 40 connected to the shaft assembly 30. The handle assembly 20 comprises a handle body 24 comprising a finger grip ring 26 integrally formed on the rear distal surface of the handle body 24 at the bottom end of the handle body 24. The shaft assembly 30 comprises a lower shaft member 22 that is integrally formed with the handle body 24 and a reciprocating upper shaft member 32 located above the lower shaft member 22. Although the lower shaft member 22 is shown integrally formed with the handle body 24, it is understood that the lower shaft member 22 can be otherwise fixedly attached (e.g., welded, fastened, and the like) to the handle body 24, and that the lower shaft member 22 and the handle body 24 are not necessarily required to be formed from a contiguous piece of material.

Figure 13:
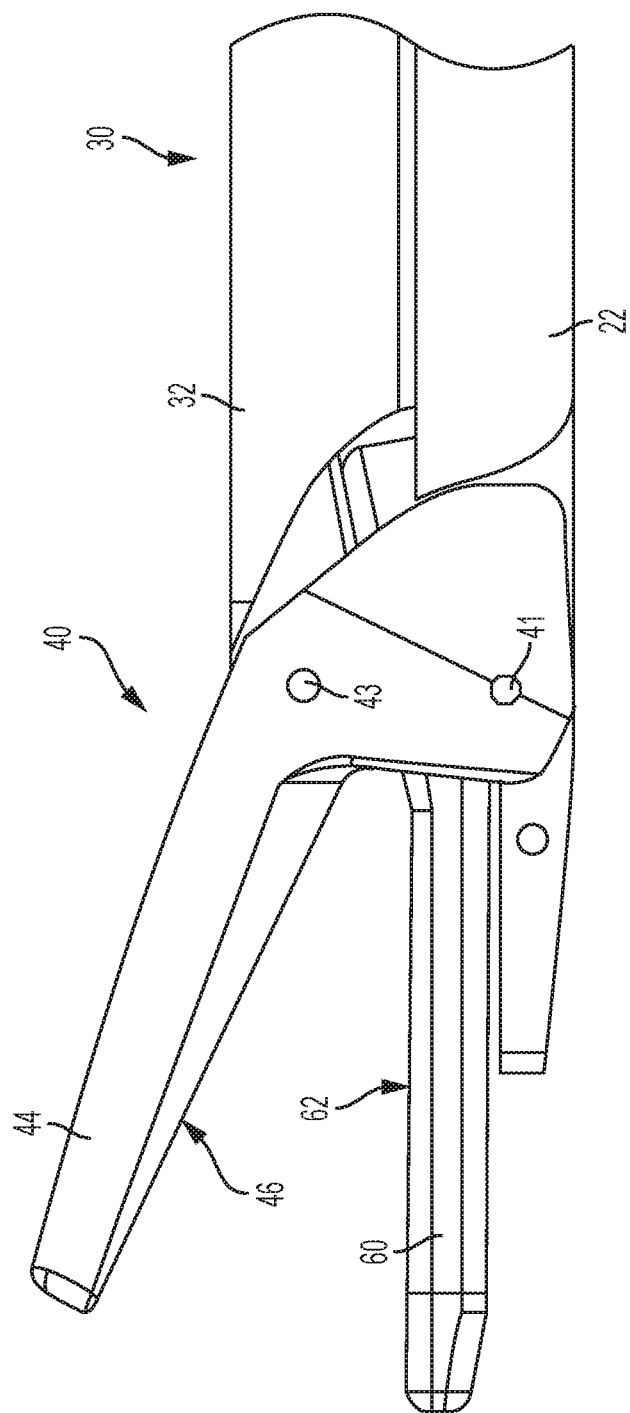
FIG. 13 is a side view of the end-effector of the ultrasonic surgical instrument shown in FIGS. 1-10 with a blade housing component removed to show the ultrasonic surgical blade.
Figure 14:
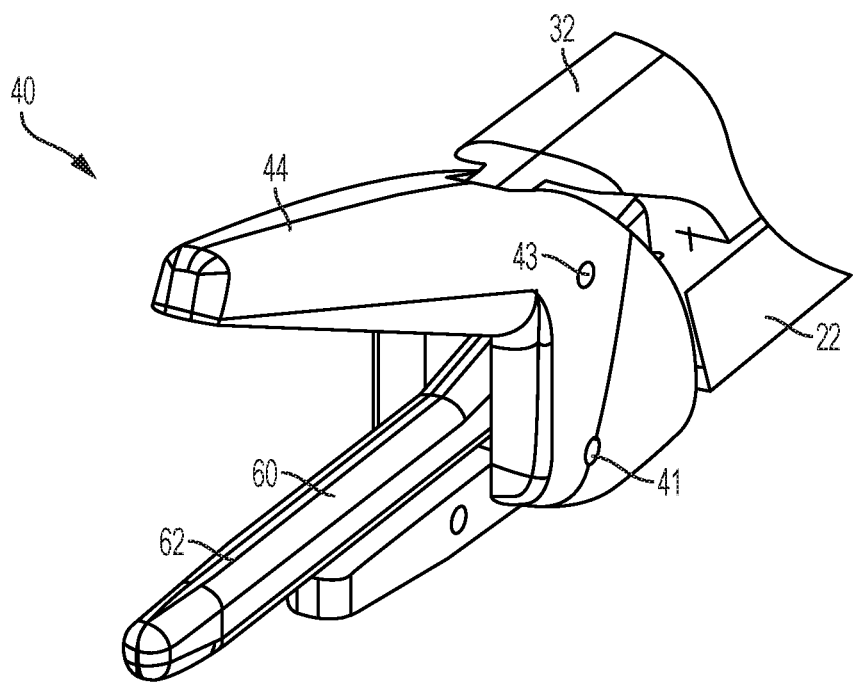
FIG. 14 is a perspective view of the end-effector shown in FIG. 13.
Figure 15:
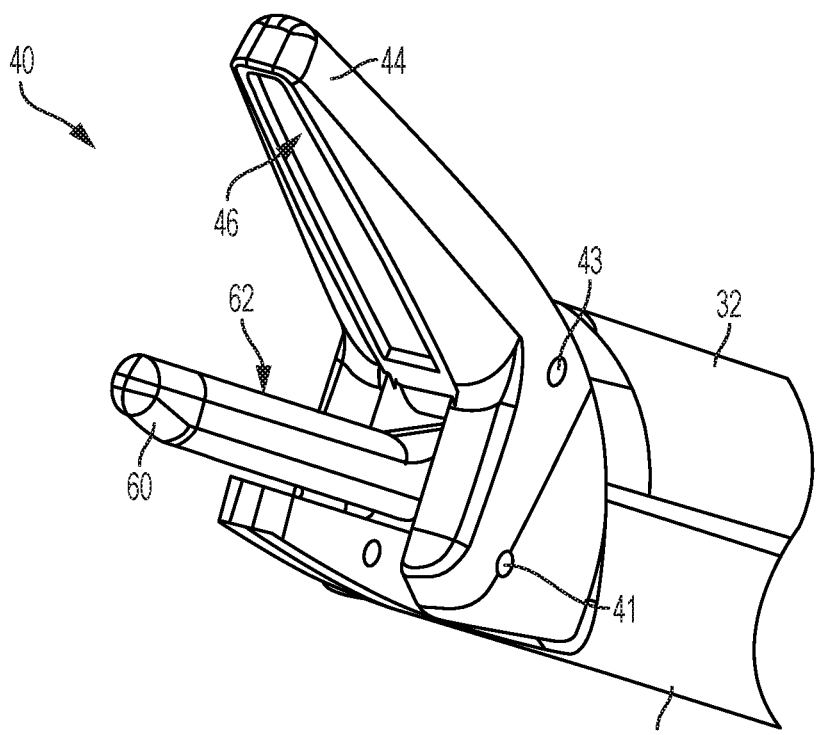
FIG. 15 is a perspective view of the end-effector shown in FIGS. 13 and 14.

The end-effector 40 comprises an ultrasonic surgical blade 60 (see FIGS. 9-15), a blade housing 42, and a clamp arm 44. The blade housing 42 of the end-effector 40 surrounds the non-tissue-engaging surfaces of the ultrasonic surgical blade 60, but the tissue-engaging surfaces 62 of the ultrasonic surgical blade 60 remain exposed for the cutting and coagulation of tissue during operation. The blade housing 42 of the end-effector 40 is connected to the lower shaft member 22 of the shaft assembly 30 using a suitable attachment (e.g., a fastener such as a pin, rivet, or screw). Referring to FIGS. 13-15, the end-effector 40 is shown with the blade housing 42 removed for ease of illustration. The clamp arm 44 is pivotably coupled to the lower shaft member 22 of the shaft assembly 30 through a pivotable joint 41 (e.g., a cylindrical pin located within a pin aperture 41a in the clamp arm 44 and a pin aperture 41b in the distal end of the lower shaft member 22—see FIGS. 9 and 10). The clamp arm 44 is also pivotably coupled to the reciprocating upper shaft member 32 of the shaft assembly 30 through a pivotable joint 43 (e.g., a cylindrical pin located within a pin aperture 43a in the clamp arm 44 and a pin aperture 43b in the distal end of the reciprocating upper shaft member 32—see FIGS. 9 and 10).

As described in more detail below, longitudinal translation of the reciprocating upper shaft member 32 causes pivoting actuation of the clamp arm 44 toward and away from the ultrasonic surgical blade 60 at the end-effector 40. In the open position, as shown in FIGS. 1-4 and 13-17, wherein the clamp arm 44 is pivoted away from the ultrasonic surgical blade 60, the end-effector 40 can be positioned in a surgical site so that tissue is located between a tissue-engaging surface 62 of the ultrasonic surgical blade 60 and a tissue-engaging surface 46 of the clamp arm 44. In the closed position, as shown in FIGS. 5-8 and 18, tissue is mechanically clamped between the respective tissue-engaging surfaces 62 and 46 of the ultrasonic surgical blade 60 and the clamp arm 44, and ultrasonic activation of the blade 60 can cause cutting and/or coagulation of the clamped tissue.

Figure 4:
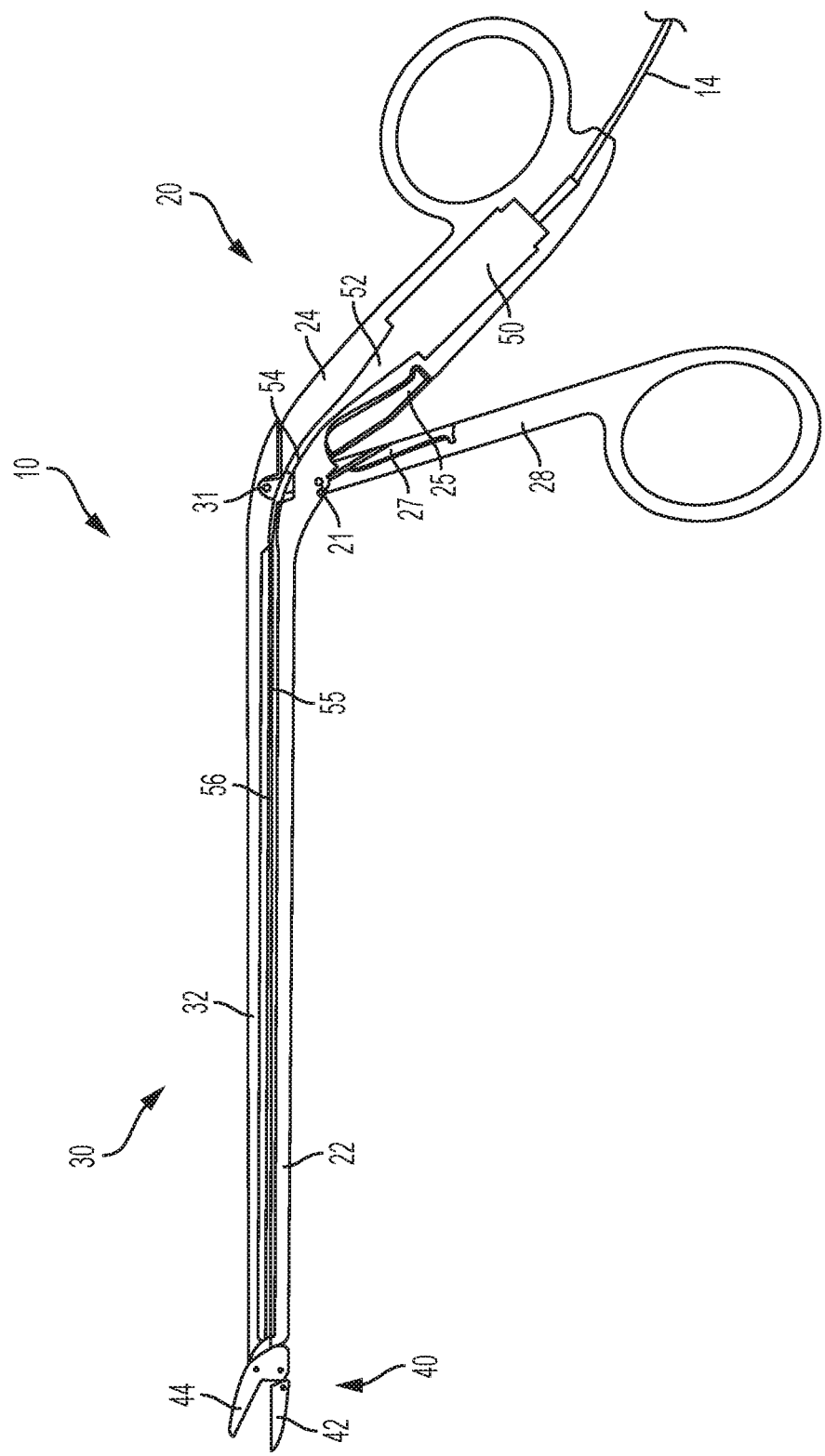
FIG. 4 is a side cross-sectional view of the ultrasonic surgical instrument shown in FIGS. 1-3.
Figure 5:
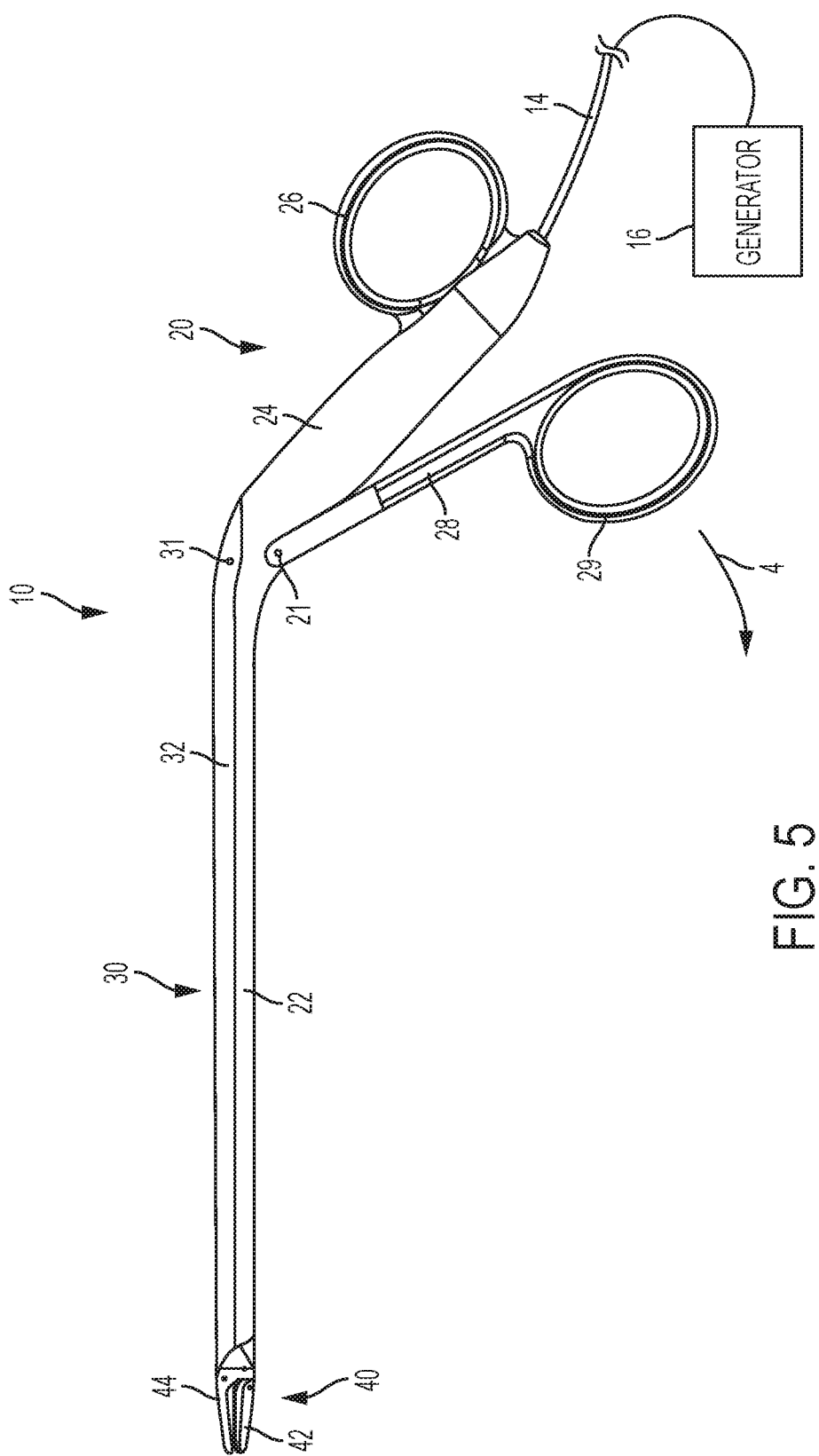
FIG. 5 is a side view of the ultrasonic surgical instrument shown in FIGS. 1-4 with the tissue clamping mechanism shown in a closed position.
Figure 6:
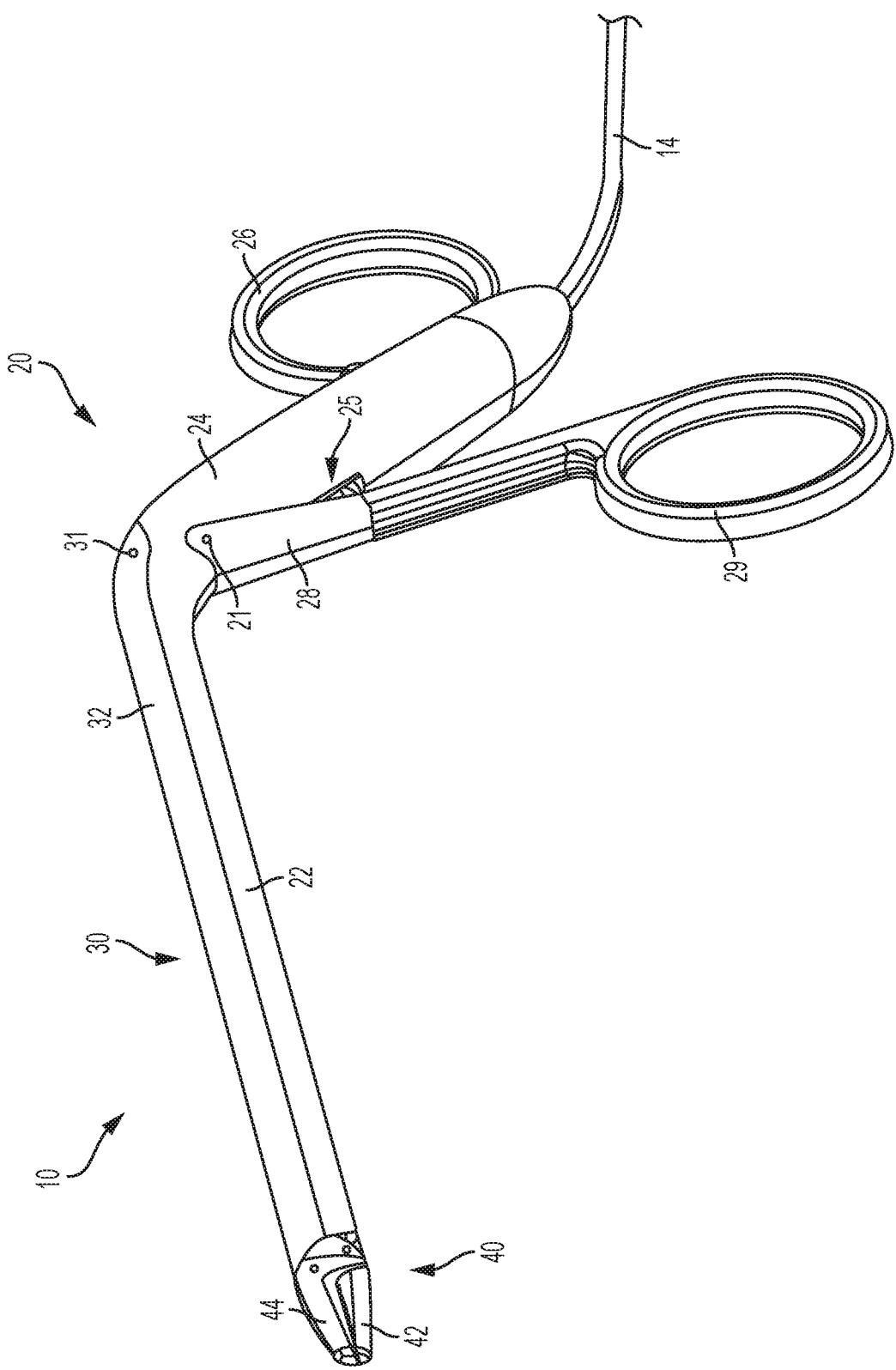
FIG. 6 is a front perspective view of the ultrasonic surgical instrument shown in FIG. 5.
Figure 7:
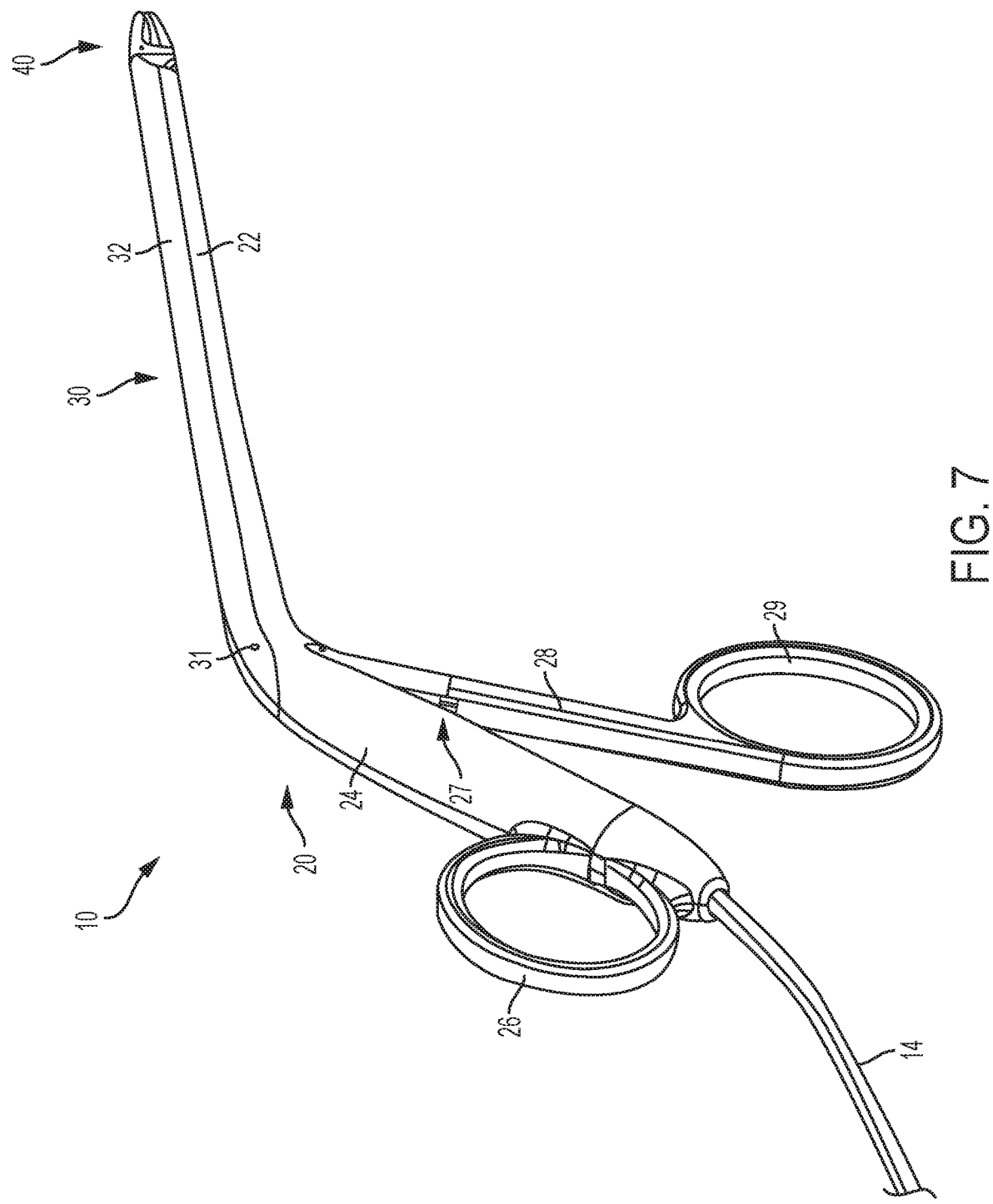
FIG. 7 is a rear perspective view of the ultrasonic surgical instrument shown in FIGS. 5 and 6.
Figure 8:
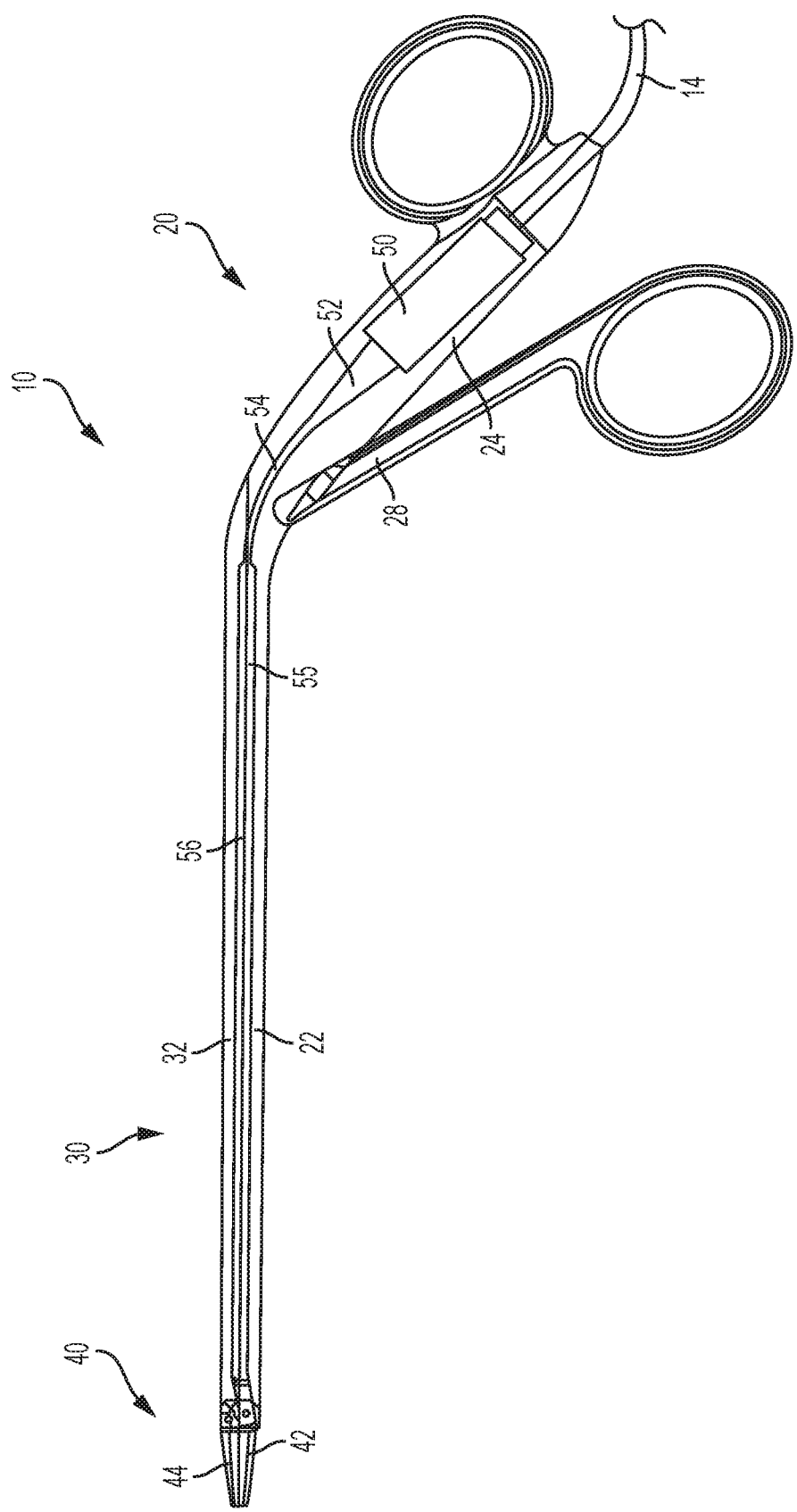
FIG. 8 is a side cross-sectional view of the ultrasonic surgical instrument shown in FIGS. 5-7.

Referring to FIGS. 4 and 8-11, the ultrasonic surgical blade 60 is acoustically coupled to an ultrasonic transmission waveguide 56. The ultrasonic transmission waveguide 56 is in turn acoustically coupled to an acoustic horn 52, which is in turn acoustically coupled to an ultrasonic transducer 50. The ultrasonic transmission waveguide 56 comprises a linear portion 55 located within the shaft assembly 30 between the lower shaft member 22 and the reciprocating upper shaft member 32. The ultrasonic transmission waveguide 56 further comprises a curved portion 54 acoustically coupled between the linear portion 55 and the acoustic horn 52. Referring to FIGS. 4 and 8, the curved portion 54 of the ultrasonic transmission waveguide 56, the acoustic horn 52, and the ultrasonic transducer 50 are located within the handle body 24 of the handle assembly 20. The ultrasonic transducer 50 is electrically coupled to a generator 16 (see FIGS. 1 and 16) via a cable 14.

During operation, the ultrasonic transducer 50 receives electrical power from the generator 16 and converts the electrical power into ultrasonic vibrations using at least one, and typically a stack of, for example, four to eight ceramic piezoelectric elements with a motion null point located at some point along the stack such as at the proximal rear end of the stack, for example. The generator 16 may include a power source and control module that is configured to provide an electrical power profile to the ultrasonic transducer 50 that is configured for the generation of ultrasonic vibrations through the transducer 50. By way of example only, the generator 16 may comprise a GEN 300 available from Ethicon Endo-Surgery, Inc. of Cincinnati, Ohio. The generator 16 may be constructed as described in U.S. Publication No. 2011/0087212, entitled "Surgical Generator for Ultrasonic and Electrosurgical Devices," published Apr. 14, 2011, which is incorporated by reference into this specification. It is understood that at least some of the functionality of the generator 16 may be integrated into the handle assembly 20; for example, the handle assembly 20 may include a battery or other on-board power source such that cable 14 is omitted.

The functionality provided by the generator 16 may also be provided as described in U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System), each of which is incorporated by reference into this specification.

Figure 9:
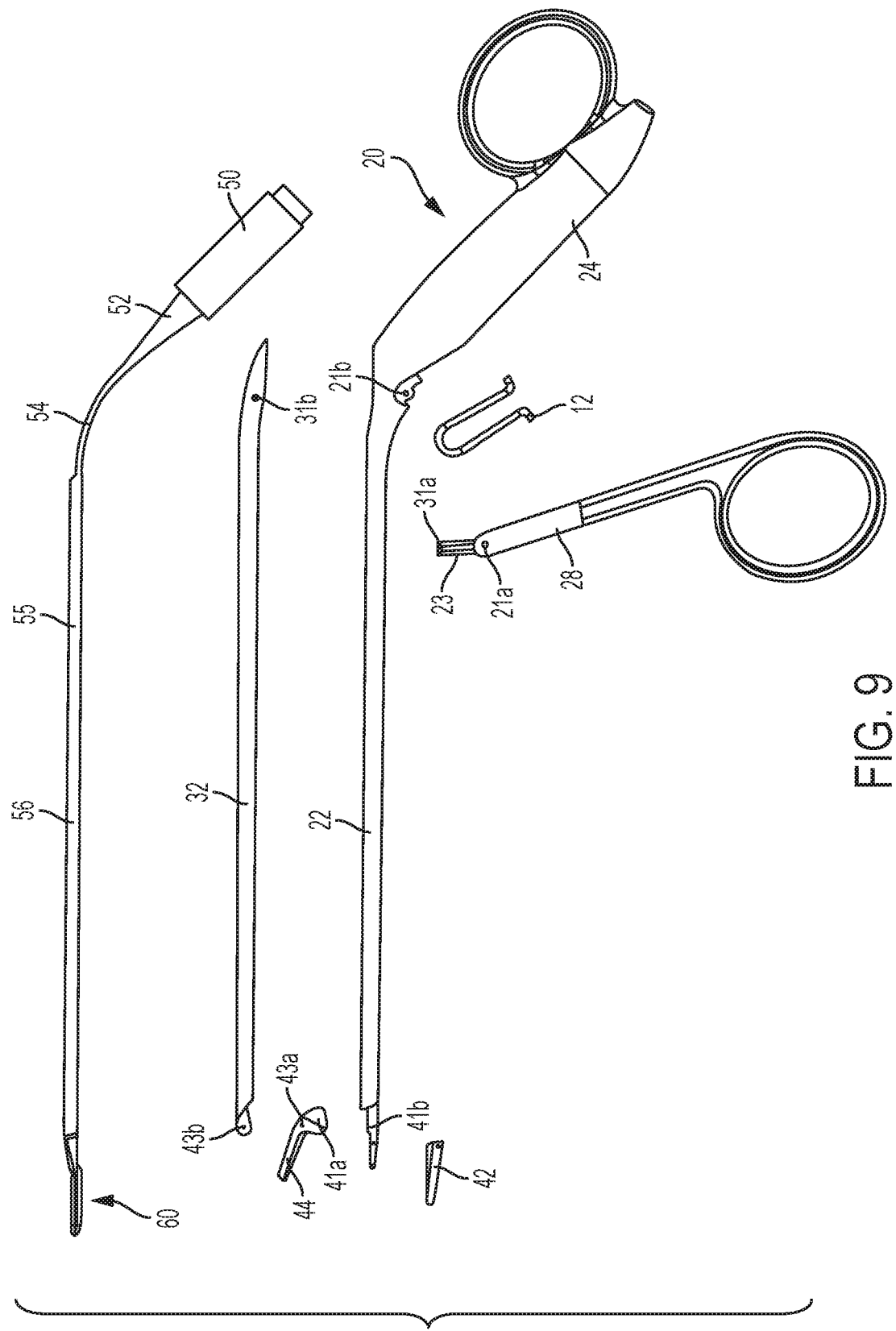
FIG. 9 is an exploded side view of the ultrasonic surgical instrument shown in FIGS. 1-8.
Figure 10:
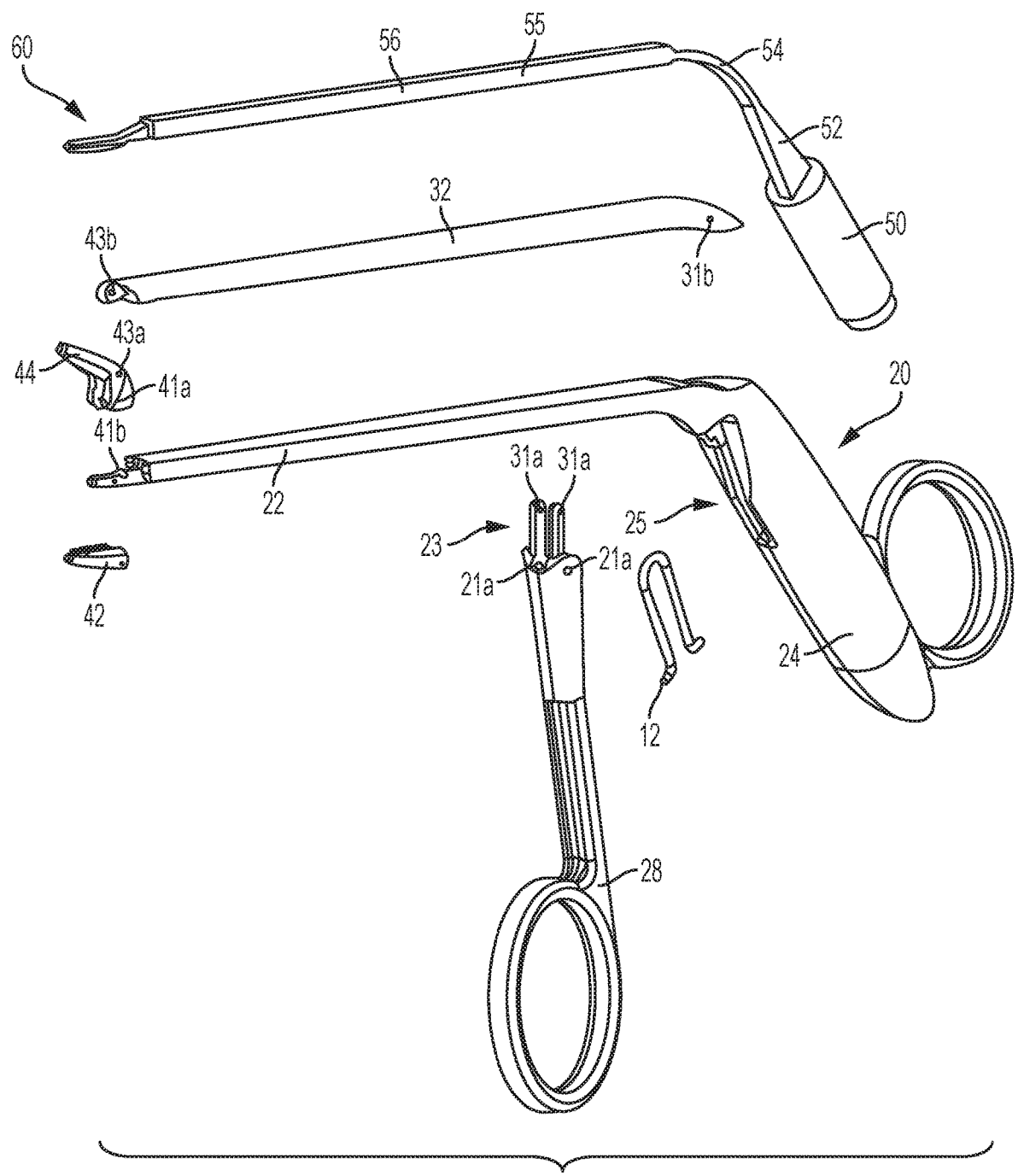
FIG. 10 an exploded front perspective view of the ultrasonic surgical instrument shown in FIGS. 1-9.

Referring again to FIGS. 1-11, the handle assembly 20 further comprises a clamp actuation member 28 comprising a finger grip ring 29 integrally formed on the front proximal surface of the clamp actuation member 28 at the bottom end of the clamp actuation member 28. Referring to FIGS. 9 and 10, the clamp actuation member 28 further comprises levering projections 23 extending from the top end of the clamp actuation member 28. The clamp actuation member 28 is pivotably coupled to the handle body 24 of the handle assembly 20 through a pivotable joint 21 (e.g., a cylindrical pin located within a pin aperture 21a in the clamp actuation member 28 and a pin aperture 21b in the handle assembly 20). The levering projections 23 of the clamp actuation member 28 are pivotably coupled to the reciprocating upper shaft member 32 of the shaft assembly 30 through a pivotable joint 31 (e.g., a cylindrical pin located within a pin aperture 31a in the levering projections 23 and a pin aperture 31b in the reciprocating upper shaft member 32).

As described above, the handle assembly 20 comprises a scissor grip configuration. It is understood, however, that a handle assembly can be structured in other configurations including, but not necessarily limited to, a pistol grip configuration as described below in connection with FIG. 21. In the illustrated scissor grip configuration, the pivoting of the clamp actuation member 28 toward and away from the handle body 24 (for example, by a surgeon's or other operator's hand with their thumb located through the finger grip ring 26 and their middle finger located through the finger grip ring 29—see FIGS. 17 and 18) longitudinally translates the reciprocating upper shaft member 32 distally and proximally, respectively, which in turn pivots the clamp arm 44 toward and away from the ultrasonic surgical blade 60, respectively, which closes and opens the clamping action of the end-effector 40. The reciprocating upper shaft member 32 translates distally and proximally relative to the lower shaft member 22, and over the linear portion 55 of the ultrasonic transmission waveguide 56, during closing and opening action of the ultrasonic surgical instrument 10.

Referring again to FIGS. 9 and 10, the handle assembly 20 comprises a biasing member 12. The biasing member 12 is illustrated in the form of a U-shaped spring clip, but it is understood that other biasing member configurations may be used. The biasing member 12 is located between the handle body 24 and the clamp actuation member 28. Referring to FIGS. 2-4, 6, 7, and 10, the biasing member 12 is seated within a recess 25 in the front proximal surface of the handle body 24 and a recess 27 in the rear distal surface of the clamp actuation member 28. The biasing member 12 biases the clamp actuation member 28 away from the handle body 24, which biases the reciprocating upper shaft member 32 proximally away from the end-effector 40, which biases the clamp arm 44 away from the ultrasonic surgical blade 60, thereby biasing the end-effector into an open position.

When a surgeon or other operator pivots the clamp actuation member 28 proximally about the joint 21, against the biasing force provided by the biasing member 12, and toward the handle body 20 (as indicated by arrow 2 in FIG. 1), the levering projections 23 pivot distally and transmit the distal motion to the reciprocating upper shaft member 32 through the joint 31. The distal motion of the reciprocating upper shaft member 32 transmits through the joint 43 to the clamp arm 44. The distal motion transmitted through the joint 43 causes the clamp arm 44 to pivot about the joint 41 toward the ultrasonic surgical blade 60, thereby closing the end-effector 40.

To open the end-effector 40, a surgeon or other operator releases the force provided by their hand against the biasing force provided by the biasing member 12. The biasing member 12 then pivots the clamp actuation member 28 distally about the joint 21 away from the handle body 20 (as indicated by arrow 4 in FIG. 5), and the levering projections 23 pivot proximally and transmit the proximal motion to the reciprocating upper shaft member 32 through the joint 31. The proximal motion of the reciprocating upper shaft member 32 transmits through the joint 43 to the clamp arm 44. The proximal motion transmitted through the joint 43 causes the clamp arm 44 to pivot about the joint 41 away from the ultrasonic surgical blade 60, thereby opening the end-effector 40.

Figure 11:
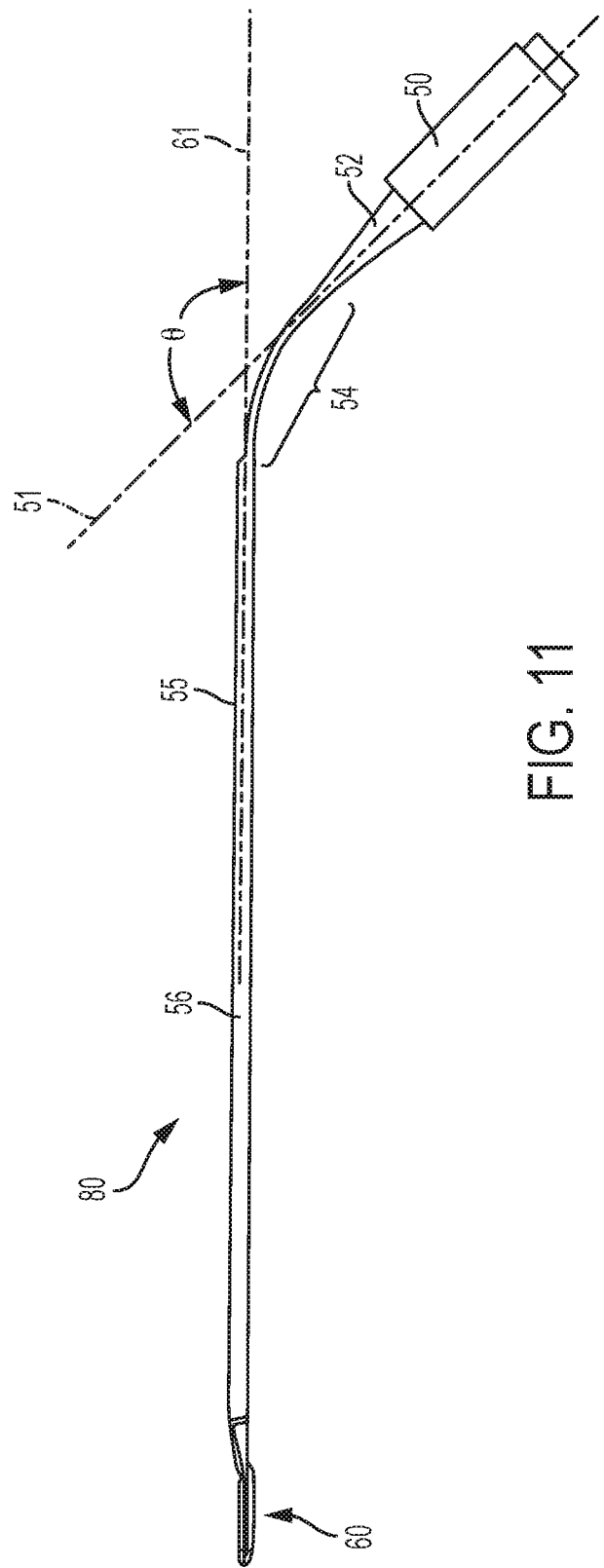
FIG. 11 is a side view schematic diagram of an acoustic system comprising an ultrasonic transducer, an ultrasonic transmission waveguide, and an ultrasonic surgical blade, showing the ultrasonic surgical blade angularly off-set from the ultrasonic transducer.

The ultrasonic surgical instrument 10 comprises an acoustic system 80. Referring to FIG. 11, the acoustic system 80 comprises the ultrasonic transducer 50, the acoustic horn 52, the ultrasonic transmission waveguide 56, and the ultrasonic surgical blade 60. As described above, the ultrasonic surgical blade 60 is acoustically coupled to the acoustic horn 52 and the ultrasonic transducer 50 through the ultrasonic transmission waveguide 56, which comprises a linear portion 55 located within the shaft assembly 30 and a curved portion 54 located within the handle assembly 20.

The orientation of the ultrasonic transducer 50 within the handle assembly 20 defines a central (linear) transducer axis 51, and the orientation of the linear portion 55 of the ultrasonic transmission waveguide 56 within the shaft assembly 30 defines a central (linear) waveguide/shaft axis 61. The central transducer axis 51 and the central waveguide/shaft axis 61 intersect and form an angle $\theta$ that angularly off-sets the ultrasonic surgical blade 60 from the central transducer axis 51. The angular off-set of the ultrasonic surgical blade 60 (and the linear portion 55 of the ultrasonic transmission waveguide 56) from the central transducer axis 51 is provided by the curved portion 54 of the ultrasonic transmission waveguide 56, which acoustically couples the linear portion 55 to the horn 52. The off-set angle $\theta$ may range, for example, from 120-degrees to 150-degrees, or any sub-range subsumed therein, such as, for example, from 130-degrees to 140-degrees. An off-set angle $\theta$ of approximately 135-degrees may provide an optimal balance of human factors and ergonomics for a surgeon or other operator of the ultrasonic surgical instrument 10 and effectiveness and efficiency of acoustic transmission through the curved portion 54 of the ultrasonic transmission waveguide 56.

The components of the acoustic system 80 may be configured to ultrasonically vibrate at the same resonant frequency. When the ultrasonic transducer 50 is energized, a standing wave is established in the ultrasonic transmission waveguide 56 defining nodes and antinodes, where the nodes represent regions of minimal or no displacement and the antinodes represent regions of maximum displacement. The nodes and antinodes occur periodically based on the driving frequency of approximately 55.5 kilohertz, for example, and the structure and materials of construction of the acoustic horn 52, the ultrasonic transmission waveguide 56, and the ultrasonic surgical blade 60. The nodes and antinodes are located at one quarter wavelength apart.

The ultrasonic transducer 50, the acoustic horn 52, the ultrasonic transmission waveguide 56, and the ultrasonic surgical blade 60 may be tuned such that the resulting length of each such element is one-half wavelength or a multiple thereof. The back and forth vibrating motion provided by the ultrasonic transducer 50 is amplified as the diameter of the acoustic horn 52 decreases closer to the ultrasonic transmission waveguide 56. The acoustic horn 52 and the ultrasonic transmission waveguide 56 may be shaped and dimensioned to amplify the motion of the ultrasonic surgical blade 60 and provide ultrasonic vibration in resonance with the rest of the acoustic system 80, which produces the maximum vibratory motion of the distal end of the acoustic horn 52 where it transitions to the ultrasonic transmission waveguide 56. For example, vibratory motion from 20 to 25 microns peak-to-peak at the piezoelectric elements of the ultrasonic transducer 50 may be amplified by the horn 52 into movement in the ultrasonic surgical blade 60 of about 40 to 100 microns peak-to-peak.

The ultrasonic vibrations that are generated by the ultrasonic transducer 50 and amplified by the horn 52 are transmitted along the ultrasonic transmission waveguide 56, through the handle assembly 20 and the shaft assembly 30, and reach the ultrasonic surgical blade 60 in the end-effector 40. The ultrasonic transmission waveguide 56 is secured within and acoustically isolated from the handle assembly 20 and the shaft assembly 30 using, for example, attachments and/or isolation spacers (not shown). The attachments and/or isolation spacers used to secure and isolate the ultrasonic transmission waveguide 56 within the handle assembly 20 and the shaft assembly 30 are located at position(s) along the length of the waveguide 56 corresponding to a node (no vibratory motion) associated with resonant ultrasonic vibrations transmitted through the ultrasonic transmission waveguide 56.

As described above, when the ultrasonic surgical blade 60 is in an activated state (i.e., vibrating ultrasonically), the ultrasonic surgical blade 60 is operable to effectively cut through and seal tissue, particularly when the tissue is being clamped between the clamp arm 44 and the ultrasonic surgical blade 60. It is understood that the waveguide 56, like the horn 52, may be configured to amplify ultrasonic mechanical vibrations transmitted through the waveguide 56, and may include features operable to control the gain of the vibrations along the waveguide 56 and/or features to tune the waveguide 56 to the resonant frequency of the acoustic system 80.

In one example, the distal end of the ultrasonic surgical blade 60 is located at a position corresponding to an anti-node associated with resonant ultrasonic vibrations communicated through the ultrasonic transmission waveguide 56, in order to tune the acoustic system 80 to a preferred resonant frequency $f_o$ when the acoustic system 80 is not loaded by tissue. When the ultrasonic transducer 50 is energized, the distal end of the ultrasonic surgical blade 60 is configured to move longitudinally along the central waveguide/shaft axis 61 (see FIG. 12) in the range of, for example, approximately 10 to 500 microns peak-to-peak, and in some instances in the range of about 20 to about 200 microns at a predetermined vibratory frequency $f_o$ of, for example, 55.5 kHz. When the ultrasonic transducer 50 is activated, the piezoelectric-mechanical vibrations are transmitted through the acoustic horn 52 and the ultrasonic transmission waveguide 56 to reach the ultrasonic surgical blade 60, thereby providing vibration of the ultrasonic surgical blade 60 at the resonant ultrasonic frequency.

In another example, the distal end of the ultrasonic surgical blade 60 is located at a position corresponding to a node associated with resonant ultrasonic vibrations communicated through the waveguide 56. When the ultrasonic transducer 50 is energized, the distal end of the ultrasonic surgical blade 60 does not move longitudinally, but a region of the tissue-engaging surface 62 corresponds to an anti-node, and that portion of the ultrasonic surgical blade 60 moves along the central waveguide/shaft axis 61 (see FIG. 12) in the range of, for example, approximately 10 to 500 microns peak-to-peak, and in some instances in the range of about 20 to about 200 microns at a predetermined vibratory frequency $f_o$ of, for example, 55.5 kHz. When the ultrasonic transducer 50 is activated, the piezoelectric-mechanical vibrations are transmitted through the acoustic horn 52 and the ultrasonic transmission waveguide 56 to reach the ultrasonic surgical blade 60, thereby providing vibration of the ultrasonic surgical blade 60 at the resonant ultrasonic frequency.

Thus, when tissue is clamped between the ultrasonic surgical blade 60 and the clamp arm 44, the ultrasonic vibration of the ultrasonic surgical blade 60 may simultaneously sever the tissue and denature the proteins in the adjacent cells and intercellular matrix of the tissue, thereby providing a coagulative effect with relatively little thermal spread. In some examples, an alternating electrical current (e.g., at radio frequencies (RF)), may also be provided through the ultrasonic surgical blade 60 and/or through electrode(s) (not shown) located on the tissue-engaging surfaces 46 of the clamp arm 44 to provide cauterization and additional tissue sealing functionality.

In various examples, a foot pedal or other switching device (not shown) operably connected to the generator 16 may be employed to control the application of electrical power from the generator 16 to the ultrasonic transducer 50. When power is applied to the ultrasonic transducer 50 by operation of a foot pedal or other switch arrangement, the acoustic system 80 may, for example, cause the ultrasonic surgical blade 60 to vibrate longitudinally along the central waveguide/shaft axis 61 (see FIGS. 11 and 12) at approximately 55.5 kHz, and the amount of longitudinal movement will vary proportionately with the amount of driving power (electrical current) applied, which may be adjustably selected by a surgeon or other operator of the ultrasonic surgical instrument 10.

When relatively high power is applied, the ultrasonic surgical blade 60 may be configured to move longitudinally in the range of about 40 to 100 microns at the ultrasonic vibrational rate. Such ultrasonic vibration of the blade 60 will generate heat as the blade contacts tissue, i.e., the acceleration of the ultrasonic surgical blade 60 through the tissue converts the mechanical energy of the moving ultrasonic surgical blade 60 to thermal energy in the localized tissue-contact area. This localized heat creates a narrow zone of coagulation, which will reduce or eliminate bleeding in small blood vessels, such as blood vessels less than one millimeter in diameter. The cutting efficiency of the ultrasonic surgical blade 60, as well as the degree of hemostasis, will vary with the level of driving power applied, the cutting rate or force applied by the surgeon to the blade 60 through the clamp arm 44, and the properties of the tissue type and the vascularity of the tissue.

Figure 16:
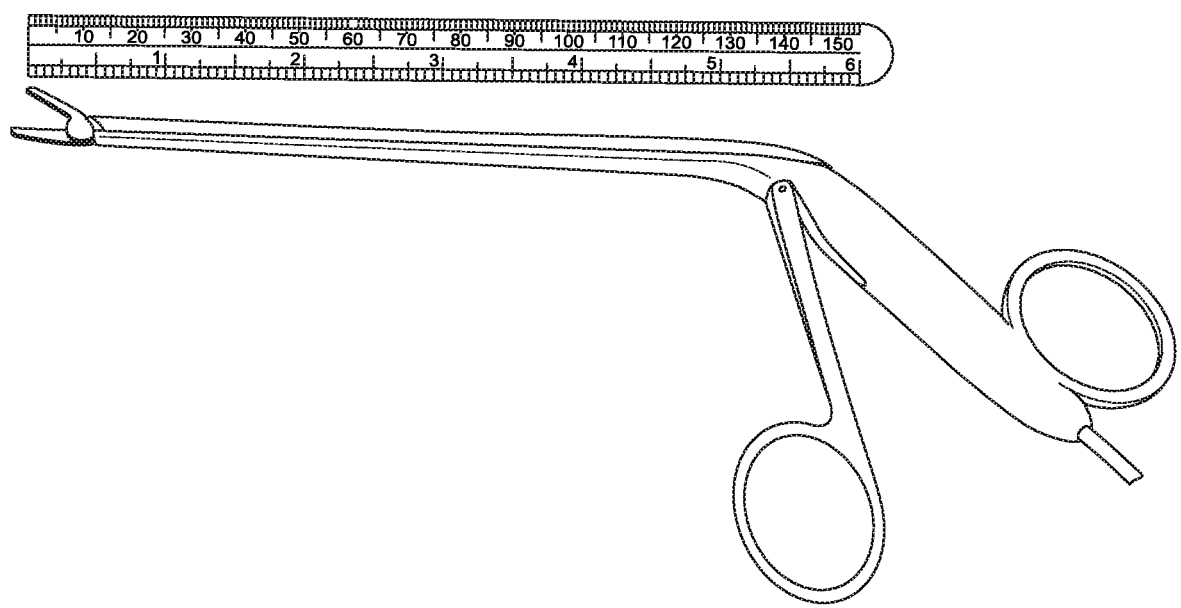
FIG. 16 is a drawing of a prototype ultrasonic surgical instrument comprising features shown in FIGS. 1-15.
Figure 17:
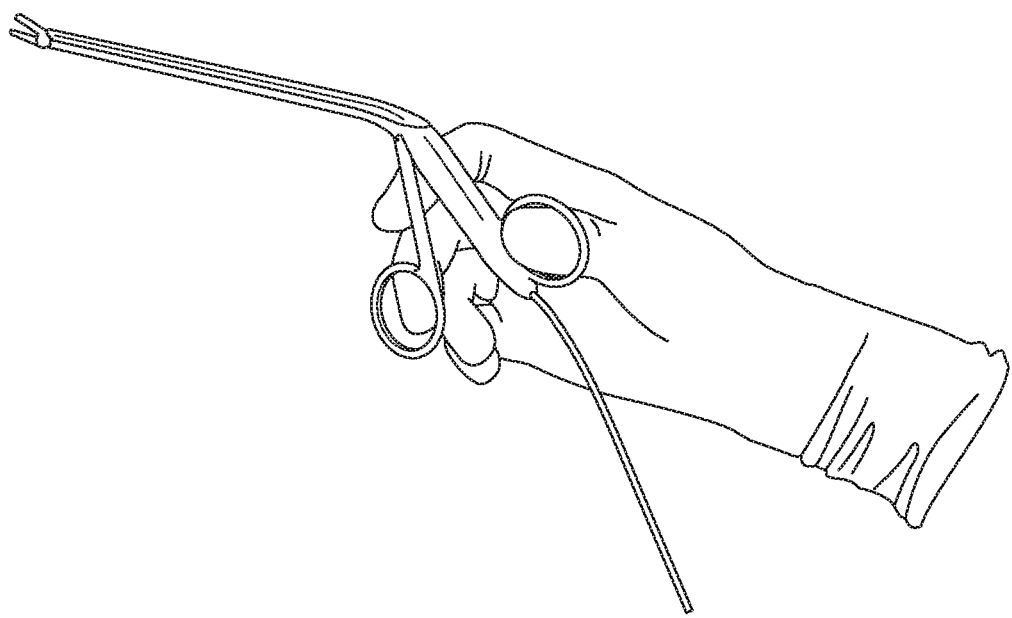
FIG. 17 is a drawing of the prototype ultrasonic surgical instrument shown in FIG. 16 in an open position in a surgeon's or other operator's hand.
Figure 18:
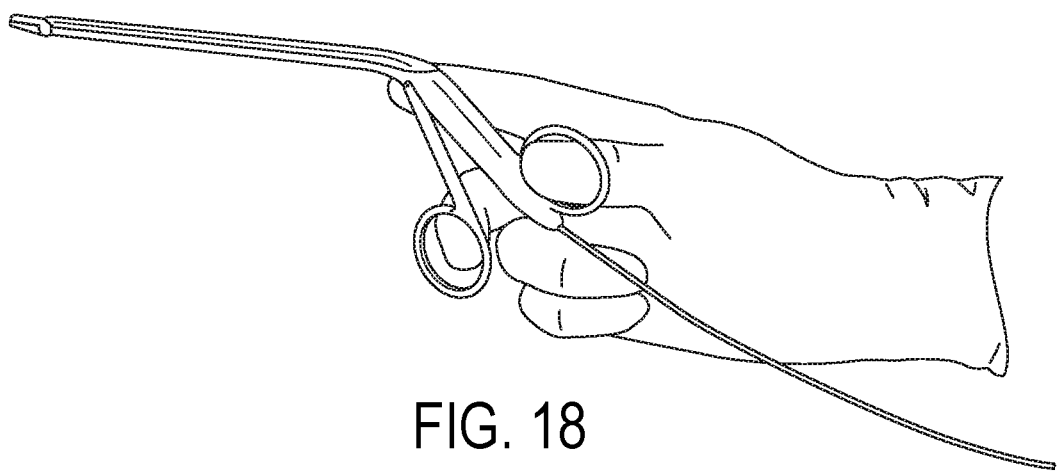
FIG. 18 is a drawings of the prototype ultrasonic surgical instrument shown in FIG. 17 in a closed position actuated by the surgeon's or other operator's hand.

Referring to FIGS. 16-18, a prototype ultrasonic surgical instrument is shown comprising the features shown in FIGS. 1-15 and described above. The prototype ultrasonic surgical instrument is shown in FIGS. 16 and 17 in an open position with the clamp arm pivoted away from the ultrasonic surgical blade, the reciprocating upper shaft member translated proximally, and the clamp actuation member pivoted away from the handle body (compare with FIG. 1). The prototype ultrasonic surgical instrument is shown in FIG. 18 in a closed position with the clamp arm pivoted toward the ultrasonic surgical blade, the reciprocating upper shaft member translated distally, and the clamp actuation member pivoted toward the handle body (compare with FIG. 5).

The ultrasonic surgical instrument 10 shown in FIGS. 1-15 (and the prototype shown in FIGS. 16-18) may facilitate improved surgical technique and execution in procedures where the surgical area is too small for the effective use of conventional scissor clamp ultrasonic devices. The angled scissor grip configuration of the ultrasonic surgical instrument 10 (provided by the angular off-set of the ultrasonic surgical blade 60 from the central transducer axis 51 of the ultrasonic transducer 50) moves the ultrasonic transducer 50 out of longitudinal alignment with the blade, which increases surgical site access, visibility, and manipulability because the shaft assembly 30 extends away from the operator's hand when grasping the handle assembly 20. In this manner, a surgeon or other operator can readily see the end-effector 40 without any obscuring or impairment of their line-of-sight by the location of the ultrasonic transducer 50 or by the location of their hand when grasping the instrument 10.

Figure 12:
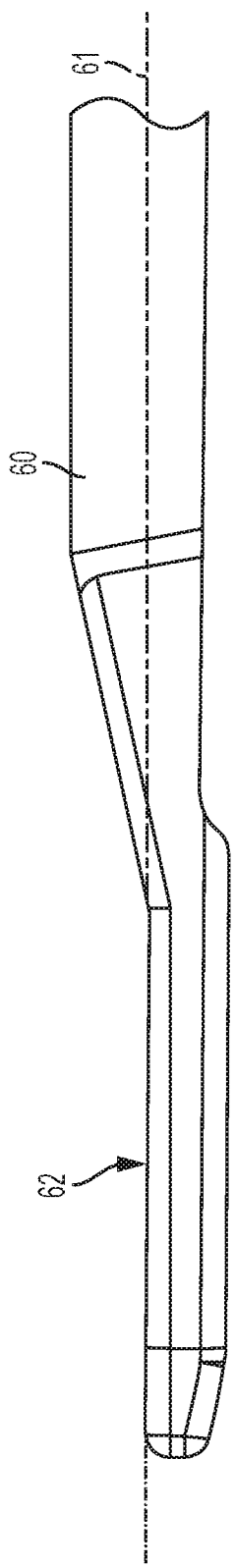
FIG. 12 is a side view schematic diagram of the ultrasonic surgical blade shown in FIG. 11.
Figure 19:
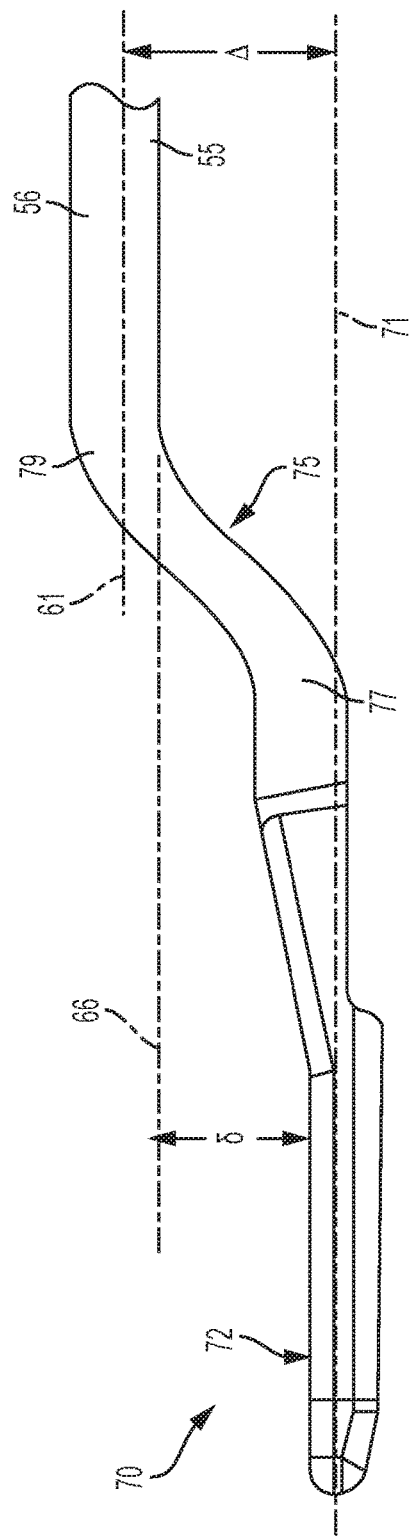
FIG. 19 is a side view schematic diagram of an ultrasonic surgical blade transversely off-set from an ultrasonic transmission waveguide through a compound curvature component connecting the ultrasonic surgical blade to the ultrasonic transmission waveguide.

As shown in FIG. 12, the ultrasonic surgical blade 60 is aligned with the central waveguide/shaft axis 61. In some examples, it would be advantageous for an ultrasonic surgical blade to off-set transversely from the central waveguide/shaft axis 61. Referring to FIG. 19, an ultrasonic surgical blade 70 is shown transversely (linearly) off-set from the linear portion 55 of the ultrasonic transmission waveguide 56. The ultrasonic surgical blade 70 has a central blade axis 71 that is parallel to the central waveguide/shaft axis 61. The tissue-engaging surface 72 of the ultrasonic surgical blade 70 is parallel to the central blade axis 71, the central waveguide/shaft axis 61, and the lower surface (indicated by the line 66) of the linear portion 55 of the ultrasonic transmission waveguide 56.

The ultrasonic surgical blade 70 is coupled to the linear portion 55 of the ultrasonic transmission waveguide 56 through a compound curvature component 75. As used herein, the term "compound curvature component" means a transitional component of an acoustic system located between a distal ultrasonic surgical blade and a proximal ultrasonic transmission waveguide or other proximal component of an acoustic system (e.g., the distal end of an acoustic horn) comprising at least two bends along the length of the component. Still referring to FIG. 19, the compound curvature component 75 comprises a distal curved portion 77 and a proximal curved portion 79. The distal curved portion 77 of the compound curvature component 75 is coupled to the ultrasonic surgical blade 70. The proximal curved portion 79 of the compound curvature component 75 is coupled to the linear portion 55 of the ultrasonic transmission waveguide 56. Although the curved portions 77 and 79 are shown as smooth curves or bends in the material forming the compound curvature component 75, it is understood that any one or more of the at least two bends along the length of a compound curvature component can be shaped such that the compound curvature component comprises a J-shape. The shape of a compound curvature component can be generally defined using a spline function.

Still referring to FIG. 19, and as described above, the compound curvature component 75 transversely (linearly) off-sets the ultrasonic surgical blade 70 from the linear portion 55 of the ultrasonic transmission waveguide 56. The central blade axis 71 is transversely off-set from the central waveguide/shaft axis 61 by a linear distance 4. As a result, the tissue-engaging surface 72 of the ultrasonic surgical blade is transversely off-set from the lower surface 66 of the linear portion 55 of the ultrasonic transmission waveguide 56 by a linear distance δ. The ultrasonic surgical blade 70 is therefore located off-axis relative to the ultrasonic transmission waveguide 56 (linearly off-axis relative to the linear portion 55, and angularly off-axis relative to the curved portion 54—see FIG. 11). The compound curvature component 75 may be connected to the linear portion 55 at a location that is distal to the most distal node in the ultrasonic transmission waveguide 56.

Figure 20:
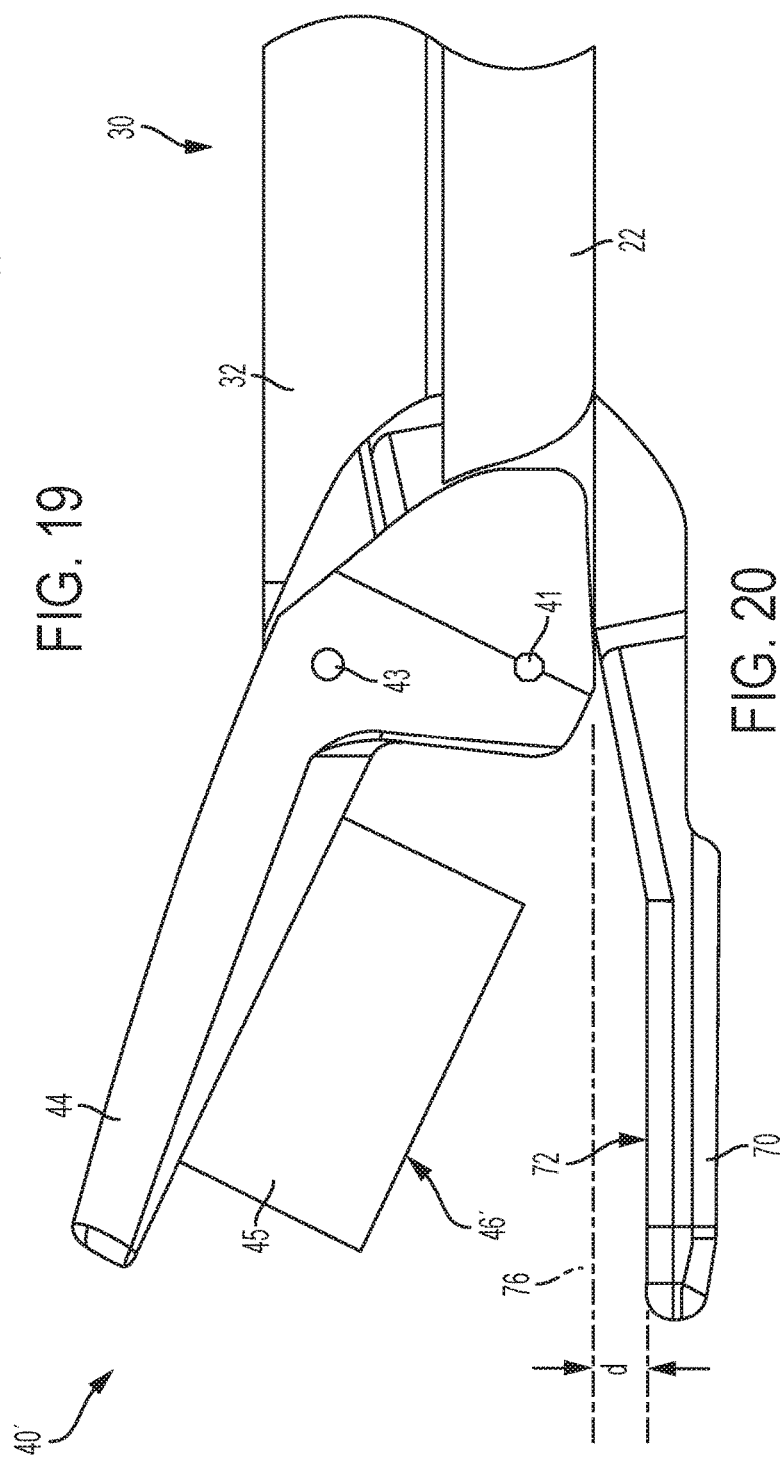
FIG. 20 is a side view of an end-effector of an ultrasonic surgical instrument comprising the ultrasonic surgical blade shown in FIG. 19.

As illustrated in FIG. 20, the transversely (linearly) off-set ultrasonic surgical blade 70 and the compound curvature component 75 can be incorporated in place of the ultrasonic surgical blade 60 in the ultrasonic surgical instrument 10 shown in FIGS. 1-18. The end-effector 40' comprises the ultrasonic surgical blade 70 and the clamp arm 44 (for ease of illustration, an optional blade housing that surrounds the non-tissue-engaging surfaces of the ultrasonic surgical blade 70, but that exposes the tissue-engaging surface 72 of the ultrasonic surgical blade 70 for the cutting and coagulation of tissue during operation, is omitted from FIG. 20). As described above, the clamp arm 44 is pivotably coupled to the lower shaft member 22 of the shaft assembly 30 through a pivotable joint 41 (e.g., a cylindrical pin located within a pin aperture 41a in the clamp arm 44 and a pin aperture 41b in the distal end of the lower shaft member 22). The clamp arm 44 is also pivotably coupled to the reciprocating upper shaft member 32 of the shaft assembly 30 through a pivotable joint 43 (e.g., a cylindrical pin located within a pin aperture 43a in the clamp arm 44 and a pin aperture 43b in the distal end of the reciprocating upper shaft member 32). The clamp arm 44 actuates in the manner described above.

Still referring to FIG. 20, the tissue-engaging surface 72 of the ultrasonic surgical blade 70 is transversely off-set from the lower surface (indicated by line 76) of the lower shaft member 22 of the shaft assembly 30 by a linear distance (d). The ultrasonic surgical blade 70 is transversely off-set away from the central waveguide/shaft axis 61 and the clamp arm 44, while the tissue-engaging surface 72 remains parallel to the waveguide/shaft axis 61. In this manner, the ultrasonic surgical blade 70 is effectively stepped-down away from the clamp arm 44, which may improve surgical site visibility and ergonomics for a surgeon or other operator. The transverse off-set of the ultrasonic surgical blade 70 away from the waveguide/shaft axis 61 and the clamp arm 44 also allows for the optional use of a thicker clamp pad 45 (with tissue-engaging surface 46') than can be accommodated in an ultrasonic surgical instrument with an ultrasonic surgical blade that is not transversely off-set away from the clamp arm 44 (see, e.g., FIG. 13).

Figure 21:
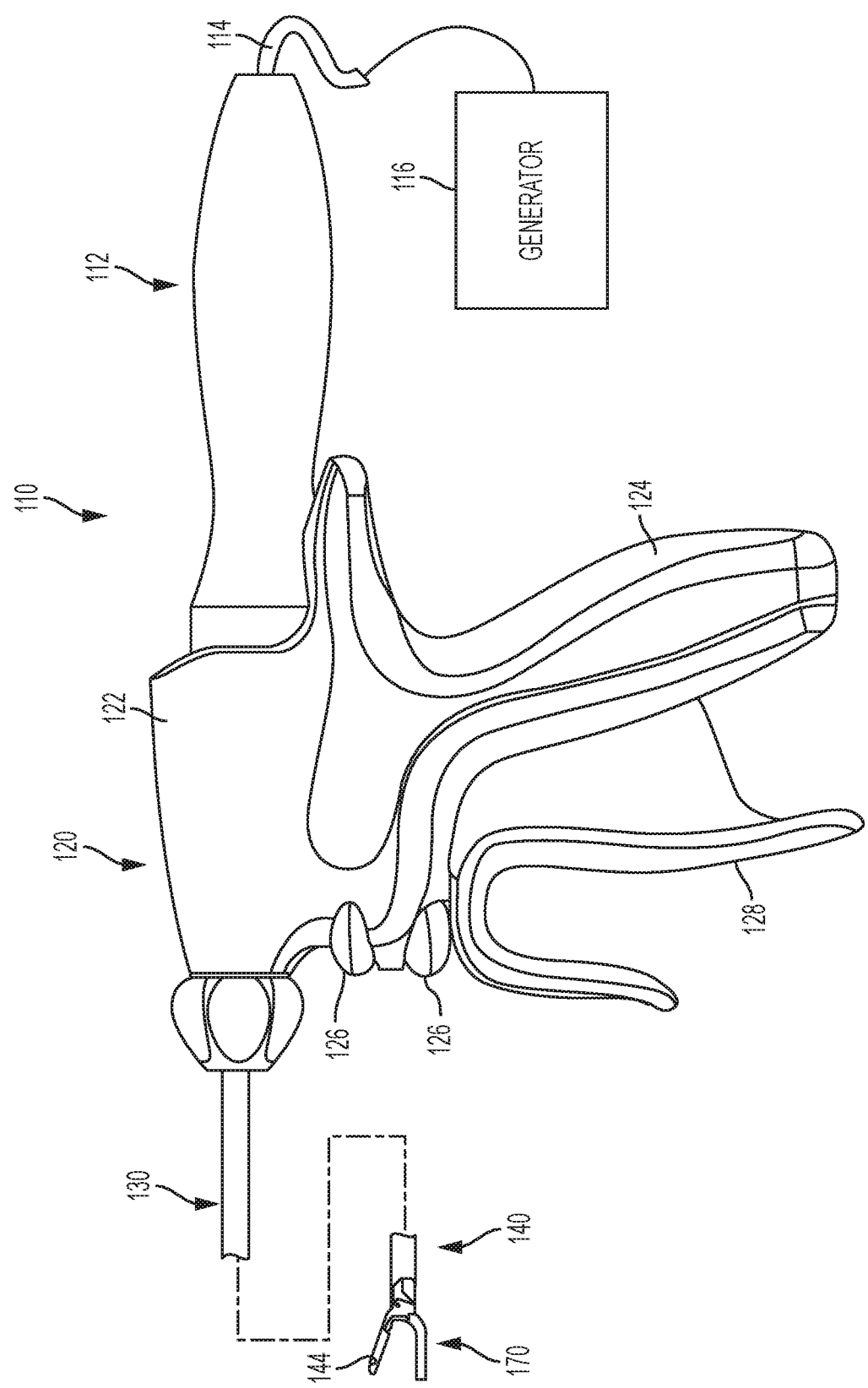
FIG. 21 is a side view of an ultrasonic surgical instrument having a tissue clamping mechanism, shown in an open position, with a pistol grip configuration and comprising an ultrasonic surgical blade that is transversely off-set from an ultrasonic transmission waveguide through a compound curvature component connecting the ultrasonic surgical blade to the ultrasonic transmission waveguide.

As described above, the examples of the ultrasonic surgical instrument 10 illustrated in FIGS. 1-20 comprise a scissor grip configuration. Although scissor grip configurations often provide excellent manual control of end-effector operation and haptic feedback from manipulated tissue, the ultrasonic surgical instruments described in this specification can be implemented using alternative configurations such as, for example, a pistol grip configuration. For example, FIG. 21 illustrates an ultrasonic surgical instrument 110 comprising a handle assembly 120, a shaft assembly 130, and an end-effector 140. As described, for example, in U.S. Publication No. 2015/0148831, which is incorporated by reference into this specification, the shaft assembly 130 can comprise an outer sheath, an inner tube slidably disposed within the outer sheath, and a waveguide disposed within the inner tube. Longitudinal translation of the inner tube causes actuation of a clamp arm 144 at an end-effector 140. Still referring to FIG. 21, the handle assembly 120 comprises a body 122 including a pistol grip 124 and a pair of buttons 126. The handle assembly 120 also includes a trigger 128 that is pivotable toward and away from the pistol grip 124.

Still referring to FIG. 21, an ultrasonic transducer assembly 112 extends proximally from the body 122 of the handle assembly 120. It is understood, however, that the ultrasonic transducer assembly 112 can be located within the pistol grip 124, for example, in a manner analogous to the location of the ultrasonic transducer 50 within the handle body 24 of the handle assembly 20 of the ultrasonic surgical instrument 10 described above in connection with FIGS. 1-11. In such examples, the ultrasonic transducer assembly 112 is structured and configured as part of an acoustic system analogous to the acoustic system 80 shown in FIG. 11, wherein the central axis of an ultrasonic surgical blade 170 and the central axis of the shaft assembly 130 are both angularly off-set from the central transducer axis of the ultrasonic transducer assembly 112 located within the pistol grip 124. The transducer assembly 112 is coupled to a generator 116 via a cable 114 and may operate and comprise the features and characteristics described above.

The end-effector 140 comprises an ultrasonic surgical blade 170 and a clamp arm 144. The end-effector 140 may comprise features and characteristics described above in connection with end-effectors 40 and 40' (see, e.g., FIGS. 13-15 and 20). An operator may activate buttons 126 to selectively activate the ultrasonic transducer assembly 112 to activate the ultrasonic surgical blade 170. In the illustrated example, the ultrasonic surgical instrument 110 is activated by two buttons 126—one for activating the ultrasonic surgical blade 170 at a lower power and another for activating the ultrasonic surgical blade 170 at a higher power. However, it is understood that any other operable number of buttons, alternative activation devices, and/or selectable power levels may be implemented. For instance, a foot pedal may be provided to selectively activate the ultrasonic transducer assembly 112.

The buttons 126 are located such that an operator may readily fully operate the ultrasonic surgical instrument 110 with a single hand. For instance, the operator may position their thumb about the pistol grip 124, position their middle, ring, and/or little finger(s) about the trigger 128, and manipulate the buttons 126 using their index finger. In operation, pivoting the trigger 128 toward the pistol grip 124 causes the clamp arm 144 to pivot toward the ultrasonic surgical blade 170, thereby closing the end-effector 144. Conversely, pivoting the trigger 128 away from the pistol grip 124 causes the clamp arm 144 to pivot away from the ultrasonic surgical blade 170, thereby opening the end-effector 144.

The example ultrasonic surgical instruments described above (10/100) comprise either a scissor grip or a pistol grip configuration to actuate an end-effector (40/40'/140) comprising a clamp arm (44/144) and an ultrasonic surgical blade (60/70/170) that is off-set angularly and/or linearly to provide an off-axis configuration (relative to the central transducer axis and/or the central waveguide/shaft axis). However, off-set ultrasonic surgical blade may be advantageous in ultrasonic surgical instruments comprising end-effectors having unencumbered ultrasonic surgical blades without clamping functionality.

Figure 22:
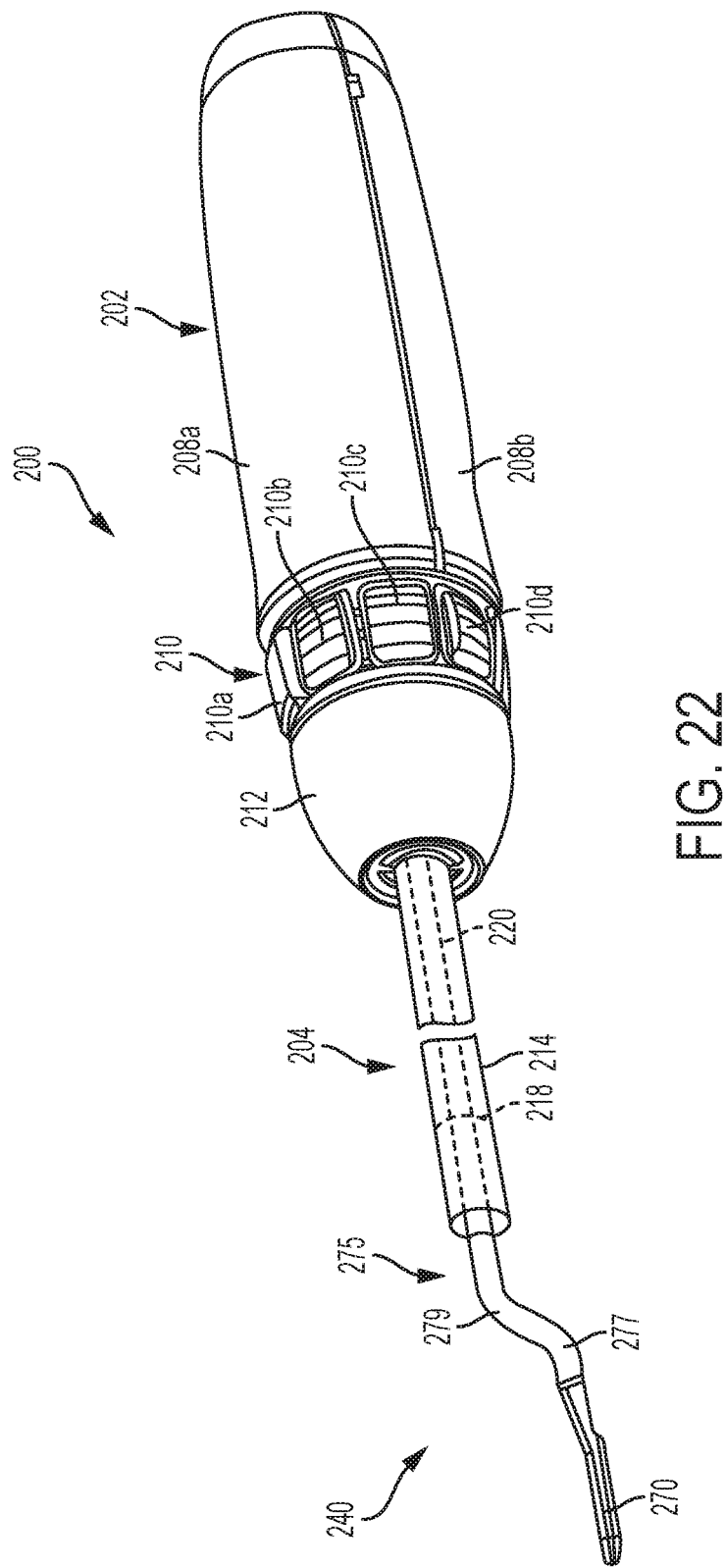
FIG. 22 is a perspective view of an ultrasonic surgical instrument without a tissue clamping mechanism and comprising an ultrasonic surgical blade that is transversely off-set from an ultrasonic transmission waveguide through a compound curvature component connecting the ultrasonic surgical blade to the ultrasonic transmission waveguide.

Referring to FIG. 22, an ultrasonic surgical instrument 200 comprises a handle assembly 202, a shaft assembly 204, and a surgical end-effector 240. The handle assembly 202 comprises a first shroud 208a and a second shroud 208b, an activation button assembly 210, and a nose cone 212. The activation button assembly 210 comprises a plurality of activation buttons 210a-210d distributed about the handle assembly 202. The shaft assembly 204 comprises an outer sheath 214. The end-effector 240 comprises an ultrasonic surgical blade 270 connected to an ultrasonic transmission waveguide 220 through a compound curvature component 275. The ultrasonic surgical blade 270 is transversely (linearly) off-set from the ultrasonic transmission waveguide 220 and the shaft assembly 204 (including the outer sheath 214). The ultrasonic transmission waveguide 220 is isolated from the outer sheath 214 with multiple isolation spacers 218, which can be overmolded over the ultrasonic transmission waveguide 220.

The handle assembly 202 also comprises an ultrasonic transducer (not shown) located within the handle assembly 202 and acoustically coupled to the ultrasonic transmission waveguide 220, which in turn is acoustically coupled to the ultrasonic surgical blade 270 through the compound curvature component 275. The handle assembly 202 is electrically connected to an ultrasonic energy generator (not shown), which can be activated by one of the plurality of activation buttons 210a-210d, for example the activation button 210a. Depressing the activation button 210a activates the ultrasonic generator and delivers electrical energy to the ultrasonic transducer located in the handle assembly 202. The ultrasonic transducer in the handle assembly 202 converts the electrical energy to ultrasonic vibratory motion, which is acoustically coupled to the ultrasonic transmission waveguide 220, the compound curvature component 275, and the ultrasonic surgical blade 270. The ultrasonic surgical blade 270 vibrates, for example, at a frequency of approximately 55.5 kilohertz and a peak-to-peak displacement of 10 to 500 microns, as described above.

Figure 23:
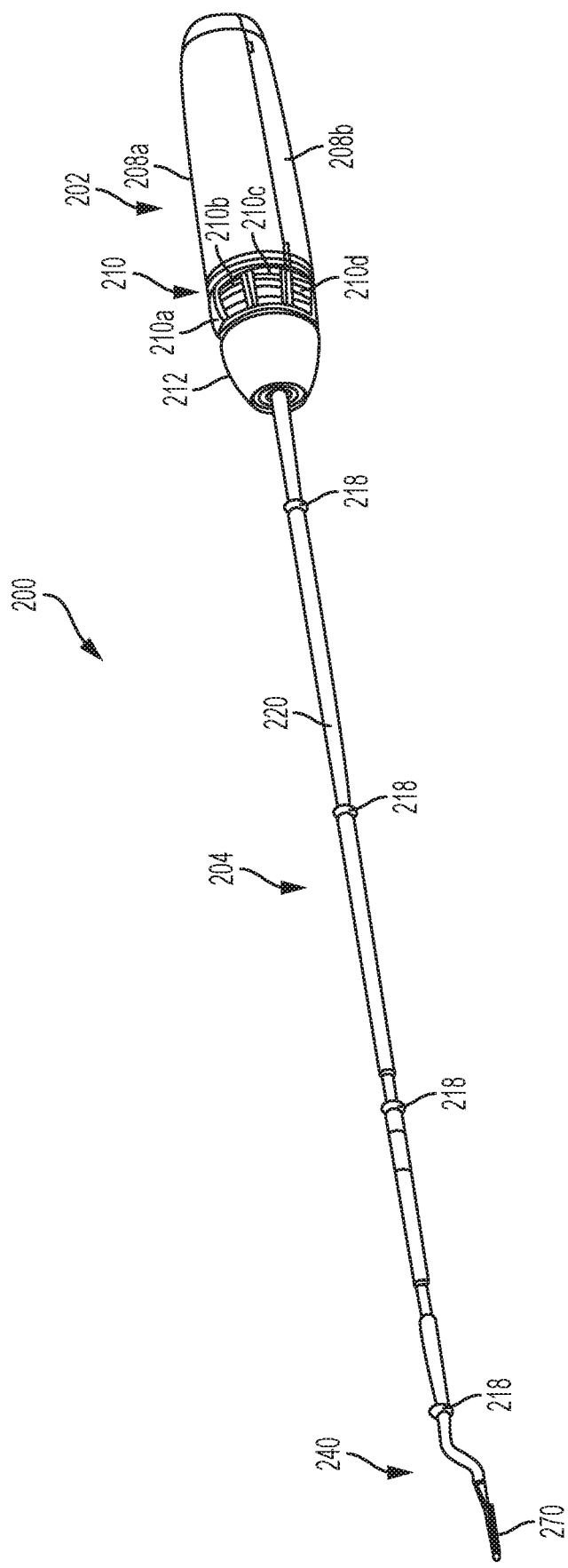
FIG. 23 is a perspective view of an ultrasonic surgical instrument comprising an ultrasonic surgical blade that is transversely off-set from an ultrasonic transmission waveguide through a compound curvature component connecting the ultrasonic surgical blade to the ultrasonic transmission waveguide.

FIG. 23 shows the ultrasonic surgical instrument 200 shown in FIG. 23 with the outer sheath 214 removed to reveal the underlying ultrasonic transmission waveguide 220. The isolation spacers 218 are located over the ultrasonic transmission waveguide 220 to acoustically isolate the outer sheath 214 from the ultrasonic transmission waveguide 220. Accordingly, the plurality of isolation spacers 218 are located on respective nodes along the ultrasonic transmission waveguide 220 to minimize the vibrations acoustically coupled to the outer sheath 214. In one example, the isolation spacers 218 may be overmolded over the ultrasonic transmission waveguide 220.

Figure 24:
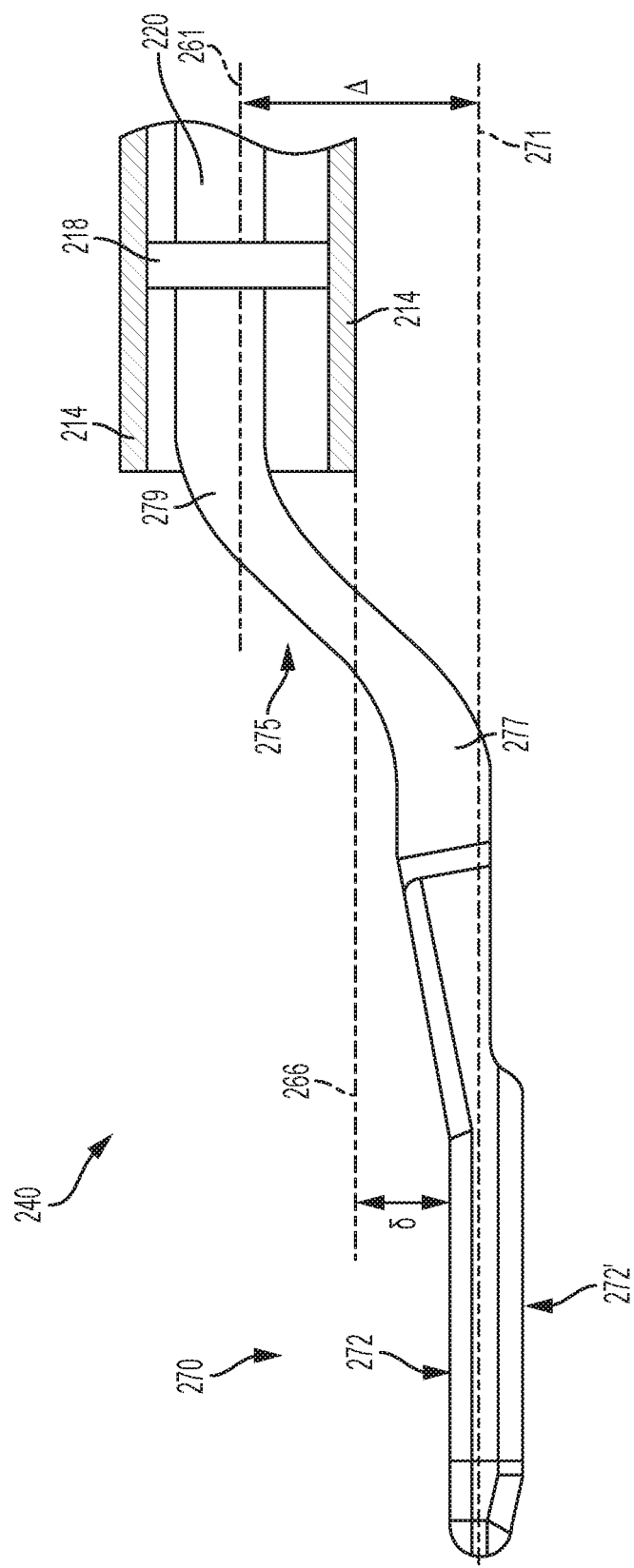
FIG. 24 is a side view schematic diagram, partially in cross-section, of an ultrasonic surgical blade that is transversely off-set from an ultrasonic transmission waveguide through a compound curvature component connecting the ultrasonic surgical blade to the ultrasonic transmission waveguide, wherein the ultrasonic transmission waveguide is located within a sheath.

Referring to FIG. 24, the ultrasonic surgical blade 270 is transversely (linearly) off-set from the ultrasonic transmission waveguide 220. The ultrasonic surgical blade 270 is coupled to the ultrasonic transmission waveguide 220 through a compound curvature component 275. The compound curvature component 275 comprises a distal curved portion 277 and a proximal curved portion 279. The distal curved portion 277 of the compound curvature component 275 is coupled to the ultrasonic surgical blade 270. The proximal curved portion 279 of the compound curvature component 275 is coupled to the ultrasonic transmission waveguide 220. Although the curved portions 277 and 279 are shown as smooth curves or bends in the material forming the compound curvature component 275, it is understood that any one or more of the at least two bends along the length of a compound curvature component can be shaped such that the compound curvature component comprises a J-shape. The shape of a compound curvature component can be generally defined using a spline function. The compound curvature component 275 may be coupled to the ultrasonic transmission waveguide 220 at a location that is distal to the most distal node in the ultrasonic transmission waveguide 220.

Still referring to FIG. 24, the compound curvature component 275 transversely off-sets the ultrasonic surgical blade 270 from the ultrasonic transmission waveguide 220. The ultrasonic surgical blade 270 defines a central blade axis 271 that is parallel to the central waveguide/shaft axis 261. The tissue-engaging surface 272 of the ultrasonic surgical blade 270 is parallel to the central blade axis 271, the central waveguide/shaft axis 261, and the outer surface (indicated by the line 266) of the outer sheath 214. The central blade axis 271 is transversely off-set from the central waveguide/shaft axis 261 by a linear distance Δ. As a result, the tissue-engaging surface 272 is transversely off-set from the outer surface 266 of the ultrasonic transmission waveguide 220 by a linear distance δ. The ultrasonic surgical blade 270 is therefore located off-axis relative to the ultrasonic transmission waveguide 220 and the outer sheath 214.

The ultrasonic surgical blade 270 comprises a tissue-engaging surface 272 facing inwardly toward the central waveguide/shaft axis 261. Alternatively, or additionally, the ultrasonic surgical blade 270 may optionally comprise a tissue-engaging surface 272' facing outwardly away from the central waveguide/shaft axis 261. Because the ultrasonic surgical instrument 200 comprises an unencumbered ultrasonic surgical blade 270, and the end-effector 240 does not comprise clamping functionality, the presence of two or more tissue-engaging surfaces 272 and 272' on the ultrasonic surgical blade 270 may increase the functionality of the ultrasonic surgical instrument 200 during surgical operations.

Figure 25:
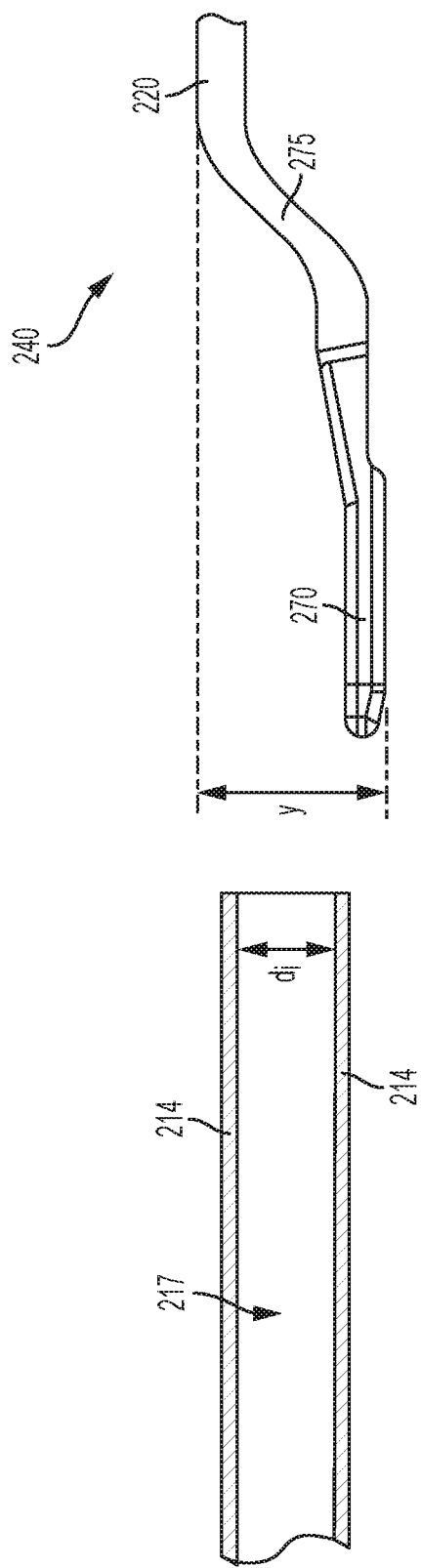
FIG. 25 is a side view schematic diagram, partially in cross-section, showing the mechanical interference caused by the size difference between a small diameter sheath and an ultrasonic surgical blade that is transversely off-set from an ultrasonic transmission waveguide through a compound curvature component connecting the ultrasonic surgical blade to the ultrasonic transmission waveguide.

The transverse off-set of the ultrasonic surgical blade 270 from the ultrasonic transmission waveguide 220 through the compound curvature component 275 increases the effective transverse size of the end-effector 240. Referring to FIG. 25, the effective transverse size (y) of the end-effector 240 may be larger than the inside diameter ($d_i$) of the outer sheath 214. The relative size difference between the inside diameter ($d_i$) of the outer sheath 214 and the effective transverse size (y) of the end-effector 240 may create mechanical interference that prevents the positioning of the ultrasonic transmission waveguide 220 within the lumen 217 of the outer sheath 214 because the inside diameter ($d_i$) is too small to accommodate the effective transverse size (y). As a result, the assembly and manufacture of ultrasonic surgical instruments, such as instruments 110 and 200 that comprise a transversely off-set ultrasonic surgical blade connected to an ultrasonic transmission waveguide located within an outer sheath, may be problematic, particularly where the ultrasonic transmission waveguide, the distally-coupled compound curvature component, and proximally-coupled components (e.g., an acoustic horn having an effective transverse size greater than $d_i$) are formed from a single piece of material (e.g., machined from metal or alloy rod or bar stock).

Additionally, in surgical applications where the surgical sites are relatively small and/or awkwardly located (e.g., transcranial, ear-nose-throat, or neck surgeries), it is advantageous to minimize the cross-sectional size of the ultrasonic transmission waveguide and the outer sheath, which further increases the size difference between the inner diameter of the outer sheath and the effective transverse size of an end-effector. Examples of slotted sheath assemblies are described below which address the assembly and manufacturing issues created by size differences between the inner diameter of an outer sheath and the effective transverse size of an end-effector comprising a transversely off-set ultrasonic surgical blade. Slotted sheath assemblies, examples of which are illustrated in FIGS. 26-42, may be used with end-effectors comprising a transversely off-set ultrasonic surgical blade, such as end-effector 240, in ultrasonic surgical instruments having unencumbered ultrasonic surgical blades without clamping functionality, or in ultrasonic surgical instruments with clamping functionality and comprising, for example, either a scissor grip or a pistol grip configuration, such as the ultrasonic surgical instruments described above (10/110/200).

Figure 26:
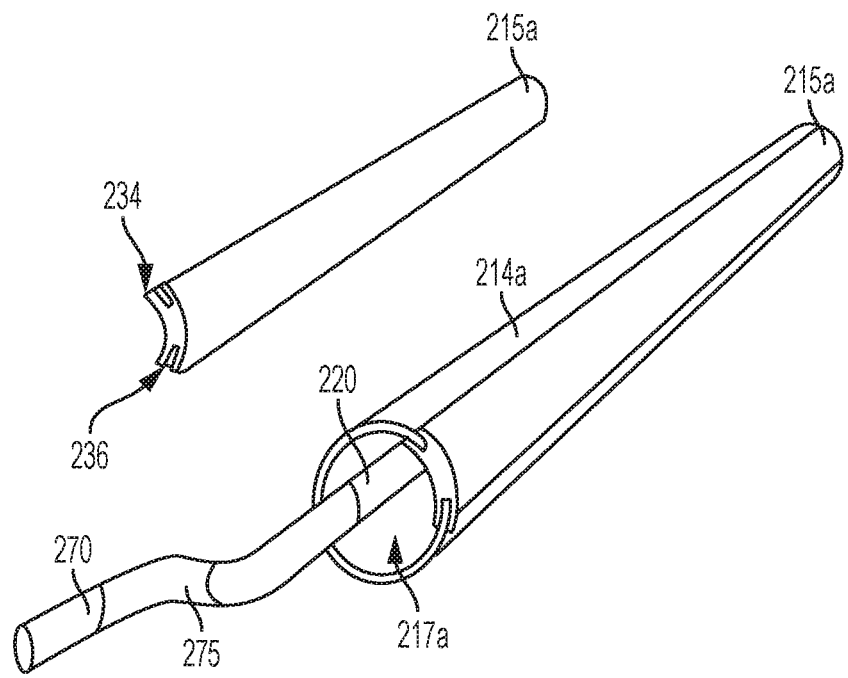
FIG. 26 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 27:
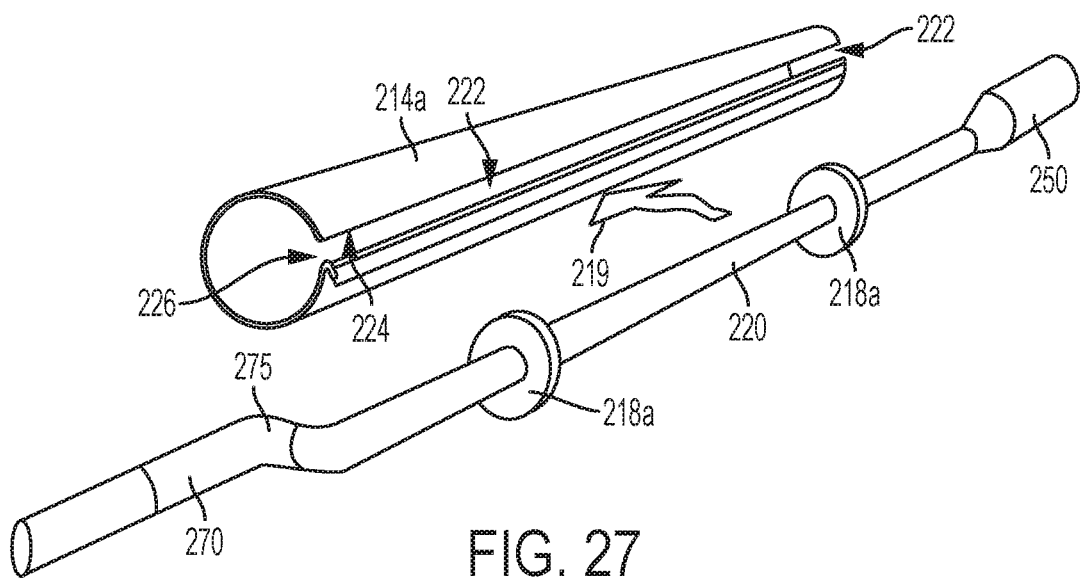
FIG. 27 is an exploded perspective view schematic diagram of the assembly shown in FIG. 26.

Referring to FIGS. 26 and 27, an acoustic system comprises an ultrasonic transducer 250, an ultrasonic transmission waveguide 220 acoustically coupled to the ultrasonic transducer 250, and an ultrasonic surgical blade 270 acoustically coupled to and transversely off-set from the ultrasonic transmission waveguide 220 through a compound curvature component 275. The proximally-coupled ultrasonic transducer 250 and the distally-coupled compound curvature component 275 prevent the ultrasonic transmission waveguide 220 and overmolded isolation spacers 218a from being inserted into a circumferentially closed sheath, as described above (see FIG. 25).

Still referring to FIGS. 26 and 27, a sheath 214a comprises an open slot 222 extending longitudinally along the proximal-distal length of the sheath 214a. The slot 222 comprises longitudinal edges 224 and 226. The sheath 214a may be made of compliant material having elastic properties (e.g., a thermoplastic material such as polytetrafluoroethylene (TEFLON) or a metallic material such as aluminum or stainless steel, for example) that permit the width of the slot 222 to be increased so that the ultrasonic transmission waveguide 220 and the isolation spacers 218a can be inserted into the lumen 217a of the sheath 214a, as indicated by the arrow 219, without the need to insert either the ultrasonic transducer 250 or the compound curvature component 275 and the ultrasonic surgical blade 270 through the lumen 217a of the sheath 214a. A sealing member 215a is then inserted into the slot 222 of the sheath 214a to bridge the slot 222, circumferentially close the sheath 214a, and seal the ultrasonic transmission waveguide 220 and the isolation spacers 218a within the lumen 217a of the sheath 214a.

The sealing member 215a comprises closed slots 234 and 236 in the longitudinal edges of the sealing member 215a and extending along the proximal-distal length of the sealing member 215a. When the sealing member 215a is inserted into the slot open 222 of the sheath 214a, the longitudinal edges 224 and 226 of the open slot 222 are secured within the closed slots 234 and 236 in the longitudinal edges of the sealing member 215a, as shown in FIG. 26. The mutual engagement of the edges 224 and 226 and the slots 234 and 236 secure the sealing member 215a in place within the slot 222, thereby bridging the slot 222, circumferentially closing the sheath 214a, and sealing the ultrasonic transmission waveguide 220 and the isolation spacers 218a within the lumen 217a of the sheath 214a. In some examples, the sealing member 215a may be made of an elastomer material (e.g., a silicone rubber material). In some examples, both the sealing member 215a and the isolation spacers 218a may be made of an elastomer material (e.g., a silicone rubber material).

Figure 28:
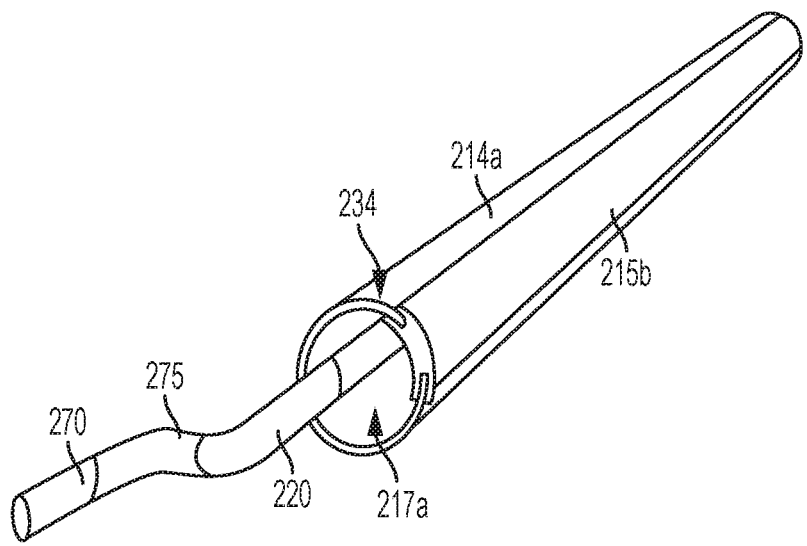
FIG. 28 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 29:
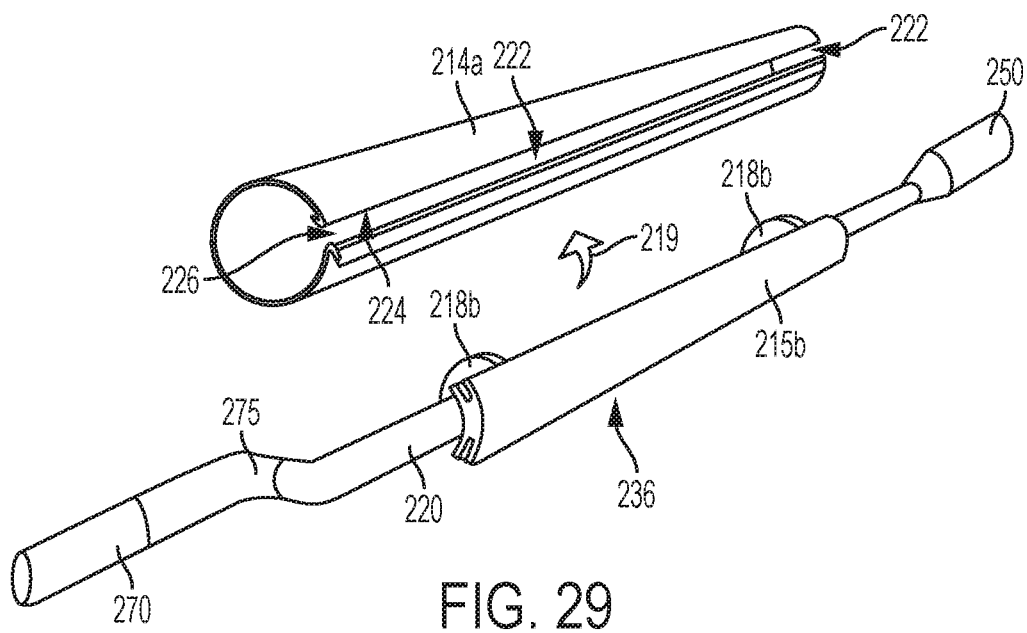
FIG. 29 is an exploded perspective view schematic diagram of the assembly shown in FIG. 28.

Referring to FIGS. 28 and 29, an alternative example is shown in which the isolation spacers 218b and the sealing member 215b are overmolded on the ultrasonic transmission waveguide 220 as a single, integral component. The ultrasonic transmission waveguide 220, the isolation spacers 218b, and the sealing member 215b are simultaneously inserted into the sheath 214a as a single assembly, as indicated by the arrow 219, without a need to insert either the ultrasonic transducer 250 or the compound curvature component 275 and the ultrasonic surgical blade 270 through the lumen 217a of the sheath 214a. When the sealing member 215b is inserted into the slot 222 of the sheath 214a, the longitudinal edges 224 and 226 of the slot 222 are secured within the slots 234 and 236 in the longitudinal edges of the sealing member 215b, as shown in FIG. 28. The mutual engagement of the edges 224 and 226 and the slots 234 and 236 secure the sealing member 215b in place within the slot 222, thereby bridging the slot 222, circumferentially closing the sheath 214a, and sealing the ultrasonic transmission waveguide 220 and the isolation spacers 218b within the lumen 217a of the sheath 214a.

Referring to FIGS. 30 and 31, an alternative example is shown in which a shrinkable tube 230 is provided instead of a sealing member 215a/215b. The ultrasonic transmission waveguide 220 and the isolation spacers 218a are inserted through the slot 222 and into the lumen 217a of the sheath 214a, as indicated by the arrow 219, without a need to insert either the ultrasonic transducer 250 or the compound curvature component 275 and the ultrasonic surgical blade 270 through the lumen 217a of the sheath 214a. The shrinkable tube 230 is then positioned over the outer circumference of the sheath 214a and shrunk to circumferentially seal the ultrasonic transmission waveguide 220 and the isolation spacers 218a within the lumen 217a of the sheath 214a. Although not shown in FIG. 30, it is understood that the shrinking of the tube 230 may impart sufficient to circumferential force to the sheath 214a to circumferentially deform the sheath 214a and bring the longitudinal edges 224 and 226 of the slot 222 into contact with each other, thereby eliminating the slot 222 and circumferentially closing the sheath 214a. The shrinkable tube 230 may be made of a heat-shrinkable material such as a crosslinked polyolefin (e.g., heat-shrinkable polyethylene, polypropylene, or poly (ethylene-propylene) copolymers).

Figure 32:
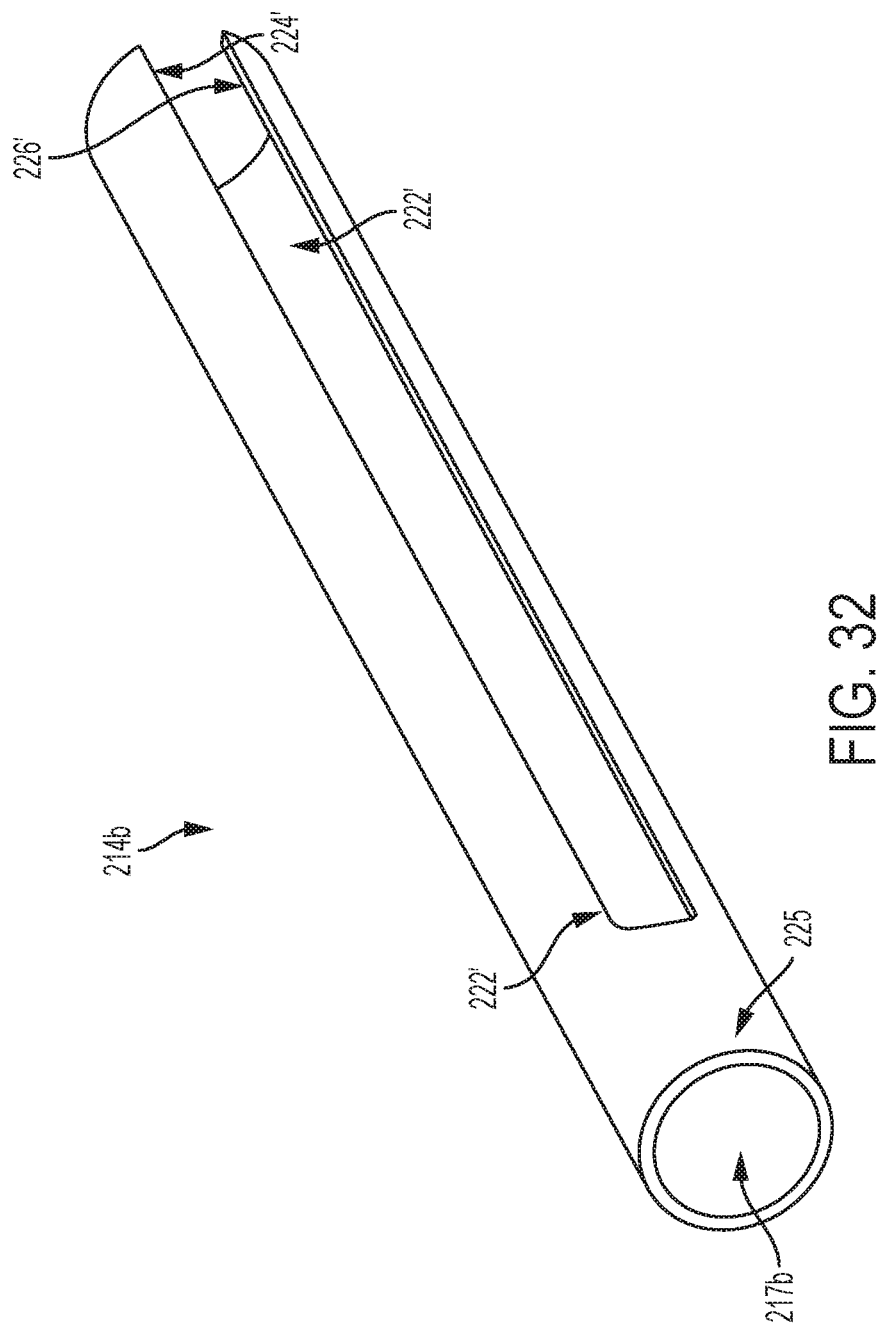
FIG. 32 is a perspective view schematic diagram of a sheath comprising a slot forming an opening located along a portion of the sheath length.

Referring to FIG. 32, an alternative example of a slotted sheath (214b) is shown, which may be used in place of the slotted sheath 214a in the examples illustrated in FIGS. 26-31. The sheath 214b comprises an open slot 222' extending longitudinally along a portion of the proximal-distal length of the sheath 214a. The sheath 214b comprises a fully-closed circumferential portion 225 at the distal end of the sheath 214b. Therefore, the slot 222' and the longitudinal edges 224' and 226' of the slot 222' only extend along a proximal portion of the total length of the sheath 214b. The fully-closed circumferential portion 225 may provided increased hoop strength to the sheath 214b.

Referring to FIGS. 33 and 34, the ultrasonic surgical blade 270, the compound curvature component 275, the ultrasonic transmission waveguide 220, and the isolation spacers 218a can be inserted through the slot 222' into the lumen 217b of the sheath 214b, as indicated by the arrow 219'. The ultrasonic surgical blade 270 and the compound curvature component 275 are inserted through the fully-closed circumferential portion 225. A sealing member 215a/215b (not shown, but see FIGS. 26-29) is then inserted into the slot 222' of the sheath 214b to bridge the slot 222', circumferentially close the sheath 214b, and seal the ultrasonic transmission waveguide 220 and the isolation spacers 218a within the lumen 217b of the sheath 214b. Alternatively, shrinkable tube 230 (not shown) is then positioned over the outer circumference of the sheath 214b and shrunk to circumferentially seal the ultrasonic transmission waveguide 220 and the isolation spacers 218a within the lumen 217b of the sheath 214b.

Figure 35:
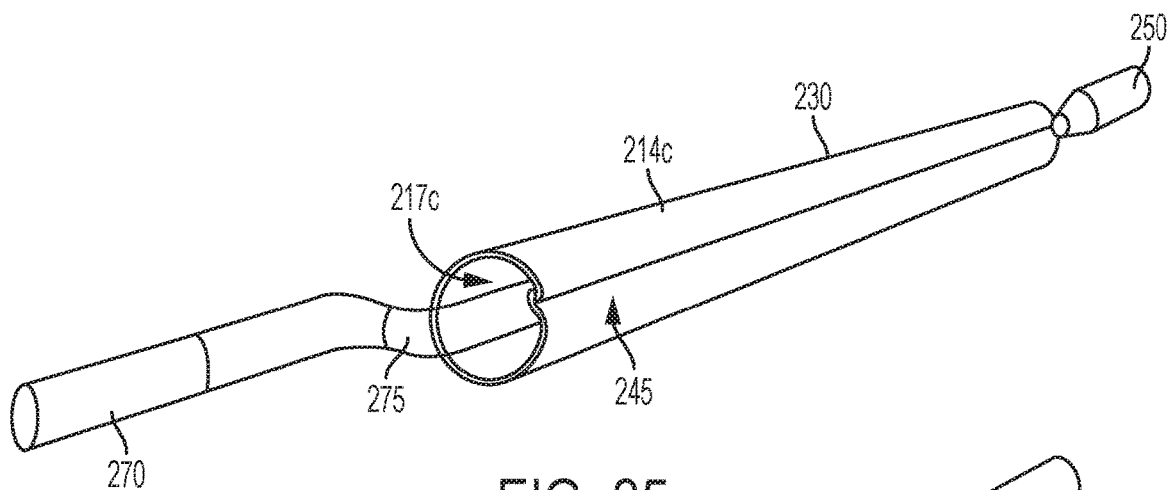
FIG. 35 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 36A:
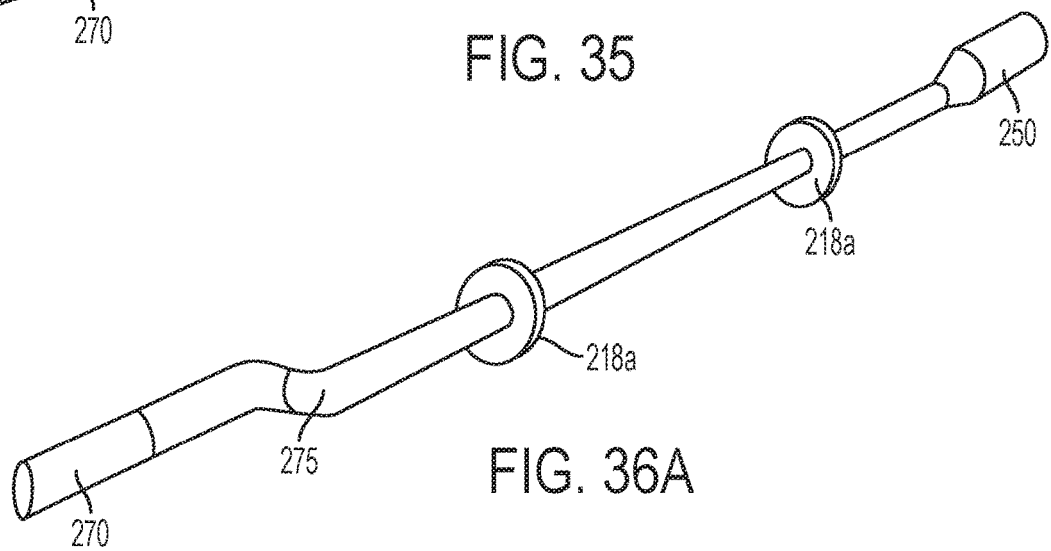
FIG. 36A is an exploded perspective view schematic diagram of the assembly shown in FIG. 35.
Figure 36B:
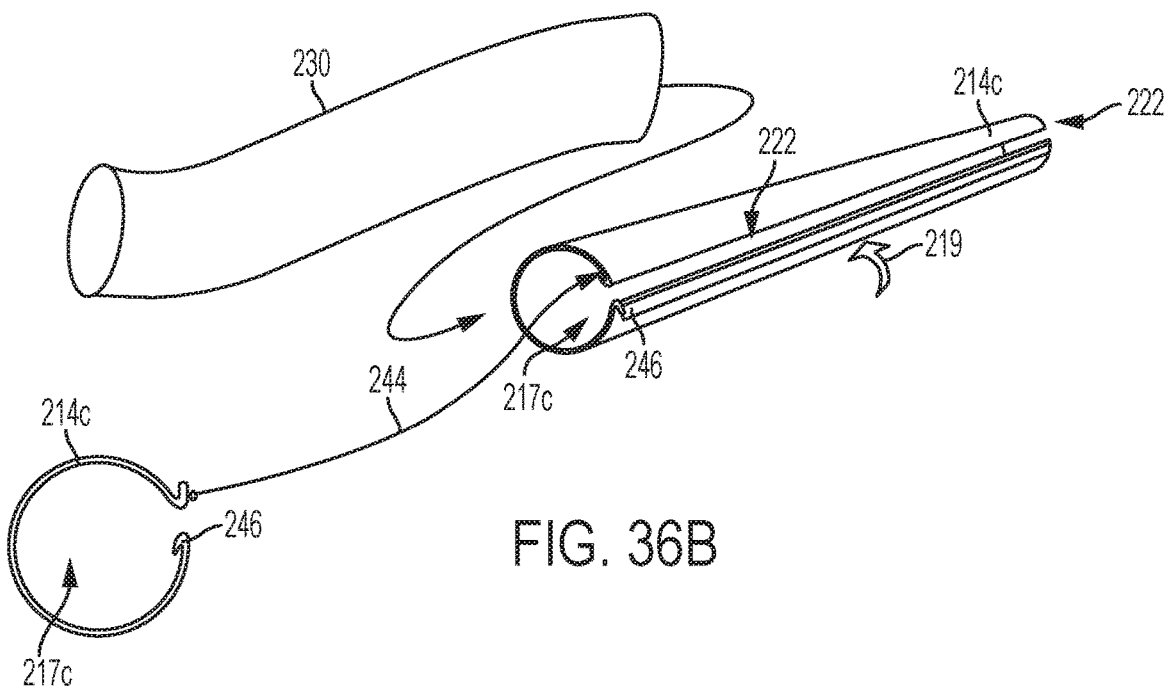
FIG. 36B is an end view schematic diagram of the sheath shown in FIG. 36A.

Referring to FIGS. 35, 36A, and 36B, a sheath 214c comprises an open slot 222 extending longitudinally along the proximal-distal length of the sheath 214c. The slot 222 comprises crimped edges 244 and 246 along the length of the slot 222. The ultrasonic transmission waveguide 220 and the isolation spacers 218a are inserted into the lumen 217C of the sheath 214C, as indicated by the arrow 219, without a need to insert either the ultrasonic transducer 250 or the compound curvature component 275 and the ultrasonic surgical blade 270 through the lumen 217c of the sheath 214c. The circumference of the sheath 214c is then compressed until the crimped edges 244 and 246 meet and interlock to form a crimped edge seam 245, as shown in FIG. 35, which closes the slot 222. A shrinkable tube 230 is then positioned over the outer circumference of the sheath 214c and shrunk to circumferentially seal the ultrasonic transmission waveguide 220 and the isolation spacers 218a within the lumen 217c of the sheath 214c.

Figure 37:
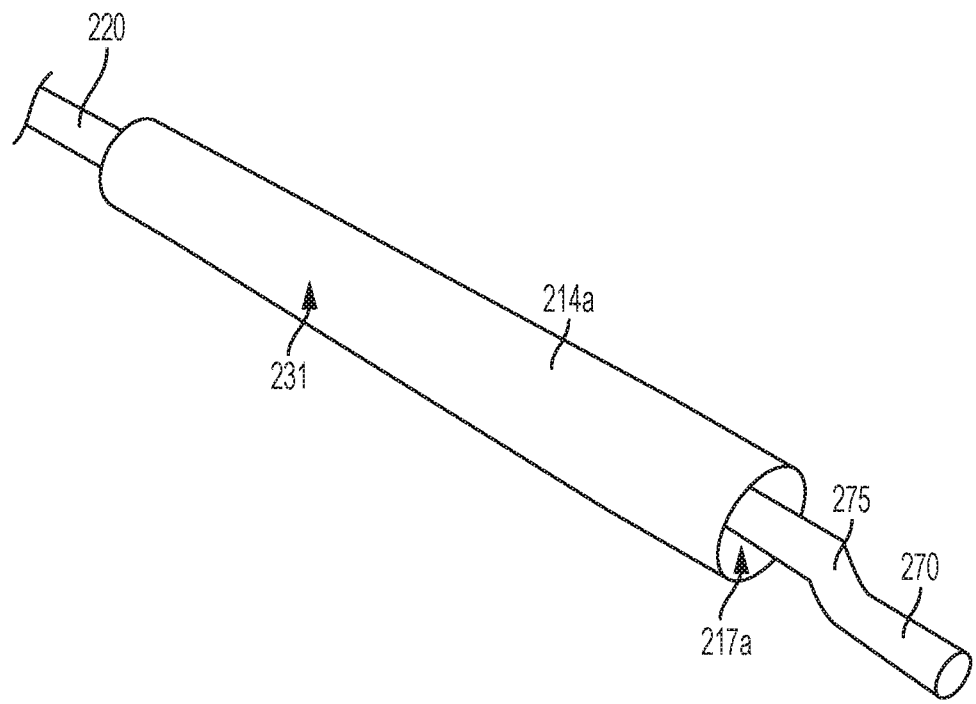
FIG. 37 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 38:
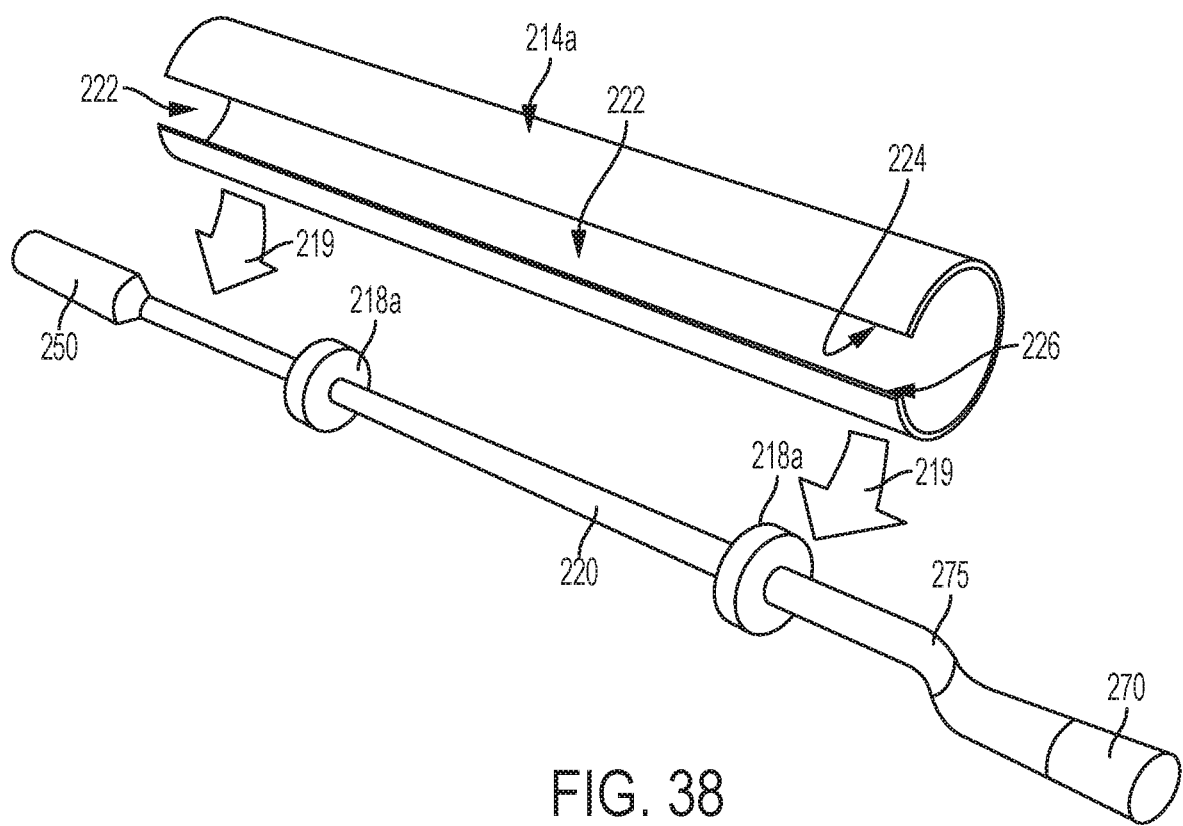
FIG. 38 is an exploded perspective view schematic diagram of the assembly shown in FIG. 37.

Referring to FIGS. 37 and 38, the ultrasonic transmission waveguide 220 and the isolation spacers 218a are inserted through the slot 222 and into the lumen 217a of the sheath 214a, as indicated by the arrows 219, without a need to insert either the ultrasonic transducer 250 or the compound curvature component 275 and the ultrasonic surgical blade 270 through the lumen 217a of the sheath 214a. The circumference of the sheath 214a is then compressed until the edges 224 and 226 of the slot 222 meet and form a seam 231, thereby closing the slot 222. The slot 222 may be permanently closed, for example, by laser welding the seam 231, ultrasonic welding the seam 231, applying adhesive to the seam 231, or otherwise bonding together the edges 224 and 226 of the slot 222 to form a bonded seam 231, which seals the ultrasonic transmission waveguide 220 and the isolation spacers 218a within the lumen 217a of the sheath 214a. Alternatively, or additionally, a shrinkable tube (not shown) is positioned over the outer circumference of the sheath 214a and shrunk to circumferentially seal the ultrasonic transmission waveguide 220 and the isolation spacers 218a within the lumen 217a of the sheath 214a.

Figure 39:
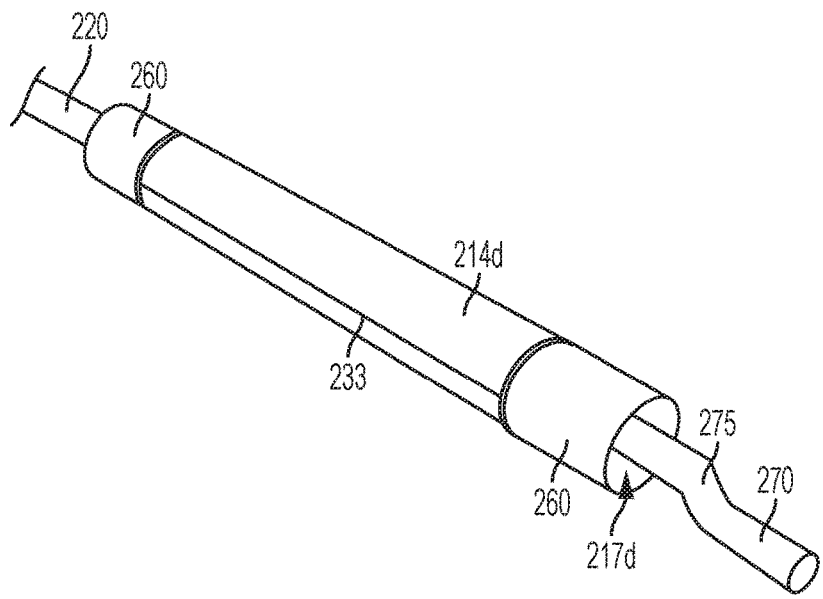
FIG. 39 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 40:
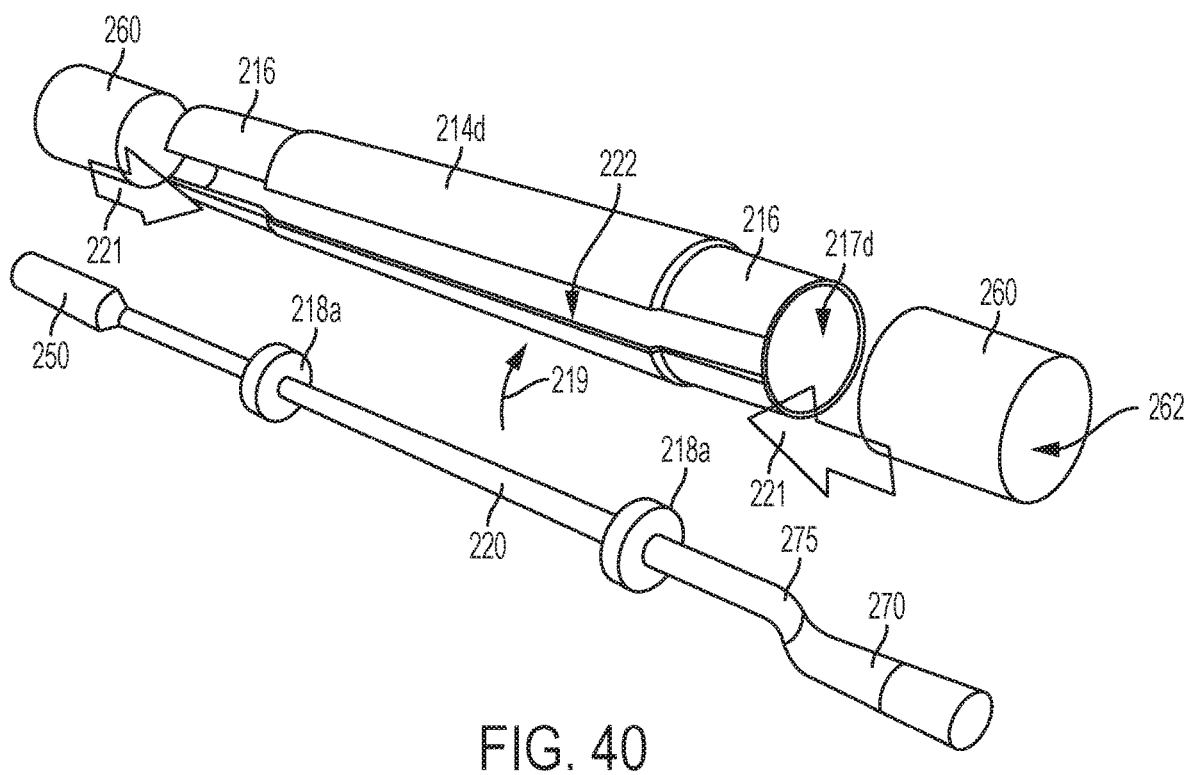
FIG. 40 is an exploded perspective view schematic diagram of the assembly shown in FIG. 39.

Referring to FIGS. 39 and 40, a sheath 214d comprises an open slot 222 extending longitudinally along the entire proximal-distal length of the sheath 214d. The sheath 214d also comprises reduced outside diameter portions 216 located on the proximal and distal ends of the sheath 214d. The ultrasonic transmission waveguide 220 and the isolation spacers 218a are inserted through the slot 222 and into the lumen 217d of the sheath 214d, as indicated by the arrow 219, without a need to insert either the ultrasonic transducer 250 or the compound curvature component 275 and the ultrasonic surgical blade 270 through the lumen 217d of the sheath 214d. The circumference of the sheath 214d is then compressed until the longitudinal edges of the slot 222 meet and form a seam 233, thereby closing the slot 222. End caps 260 are then press fit onto the proximal and distal ends of the sheath 214d, as indicated by arrows 221, wherein the reduced outside diameter portions 216 of the sheath 214d are inserted into the lumens 262 of the end caps 260.

The press fitting of the end caps 260 over the reduced outside diameter portions 216 of the sheath 214d close the slot 222, which seals the ultrasonic transmission waveguide 220 and the isolation spacers 218a within the lumen 217d of the sheath 214d. Optionally, the seam 233 may be laser welded, ultrasonic welded, bonded with an adhesive, or otherwise bonded. Alternatively, or additionally, a shrinkable tube (not shown) is positioned over the outer circumference of the sheath 214d and shrunk to further circumferentially seal the ultrasonic transmission waveguide 220 and the isolation spacers 218a within the lumen 217d of the sheath 214d.

Figure 41:
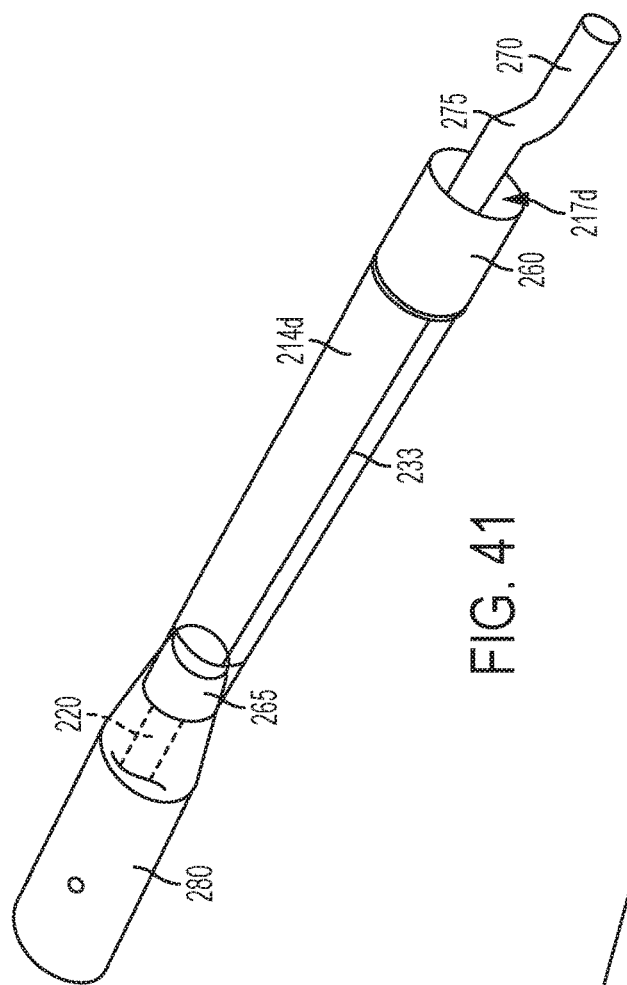
FIG. 41 is a perspective view schematic diagram of an ultrasonic surgical blade that is transversely off-set from an ultrasonic transmission waveguide through a compound curvature component connecting ultrasonic surgical blade to the ultrasonic transmission waveguide, wherein the ultrasonic transmission waveguide is located within a sheath.
Figure 42:
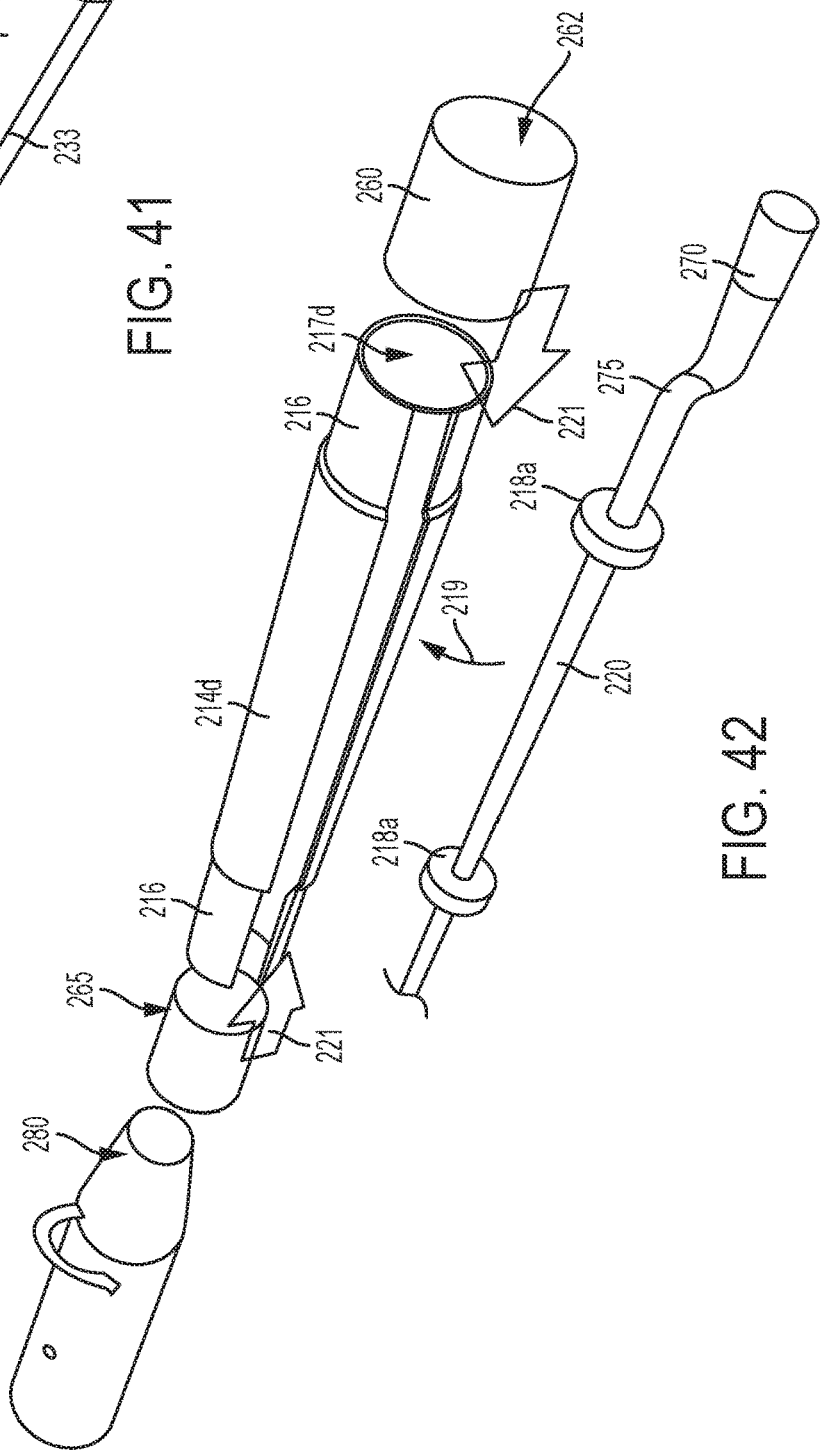
FIG. 42 is an exploded perspective view schematic diagram of the assembly shown in FIG. 41.
Figure 43:
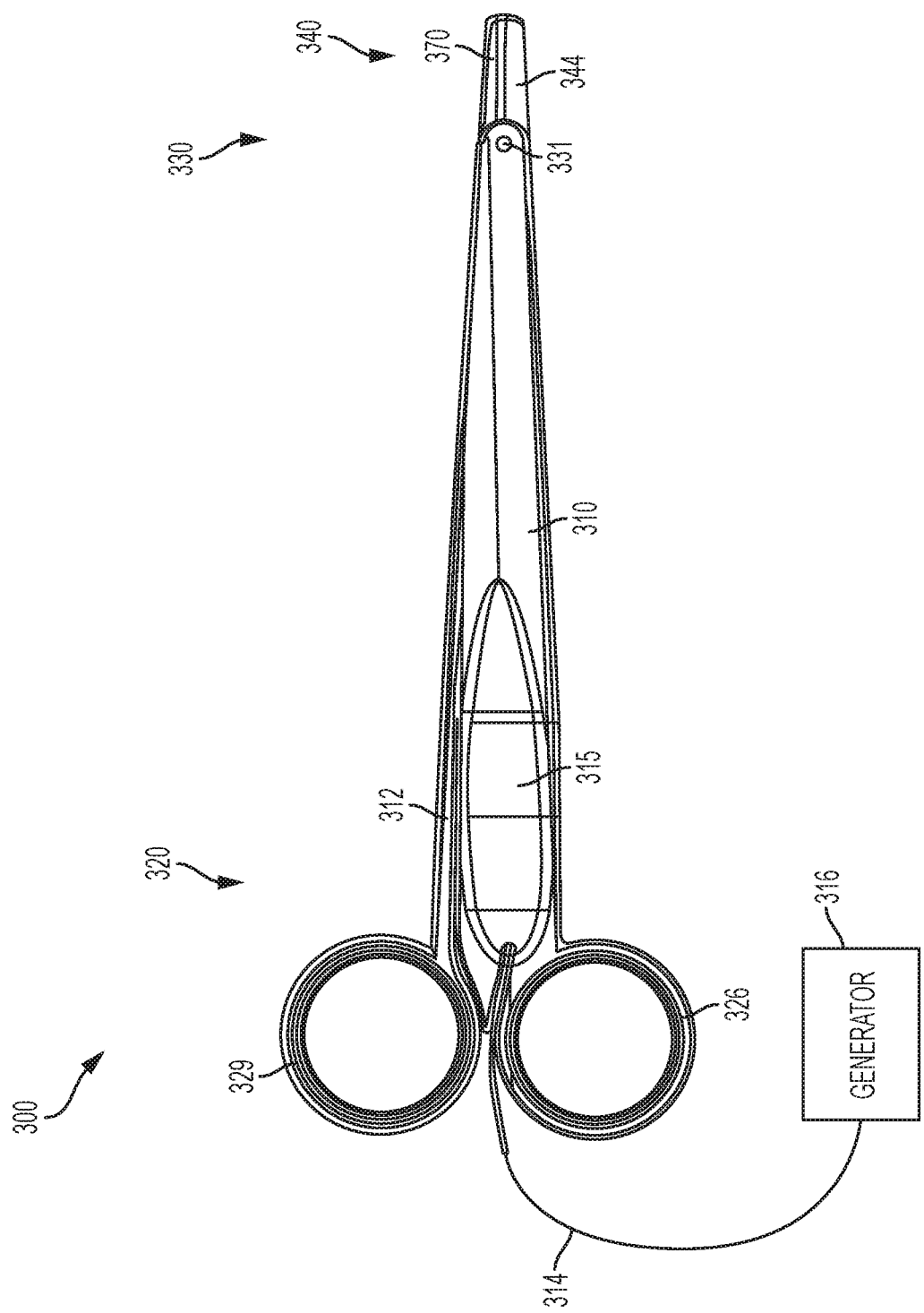
FIG. 43 is a side view of an ultrasonic surgical instrument having a scissor grip configuration.
Figure 44:
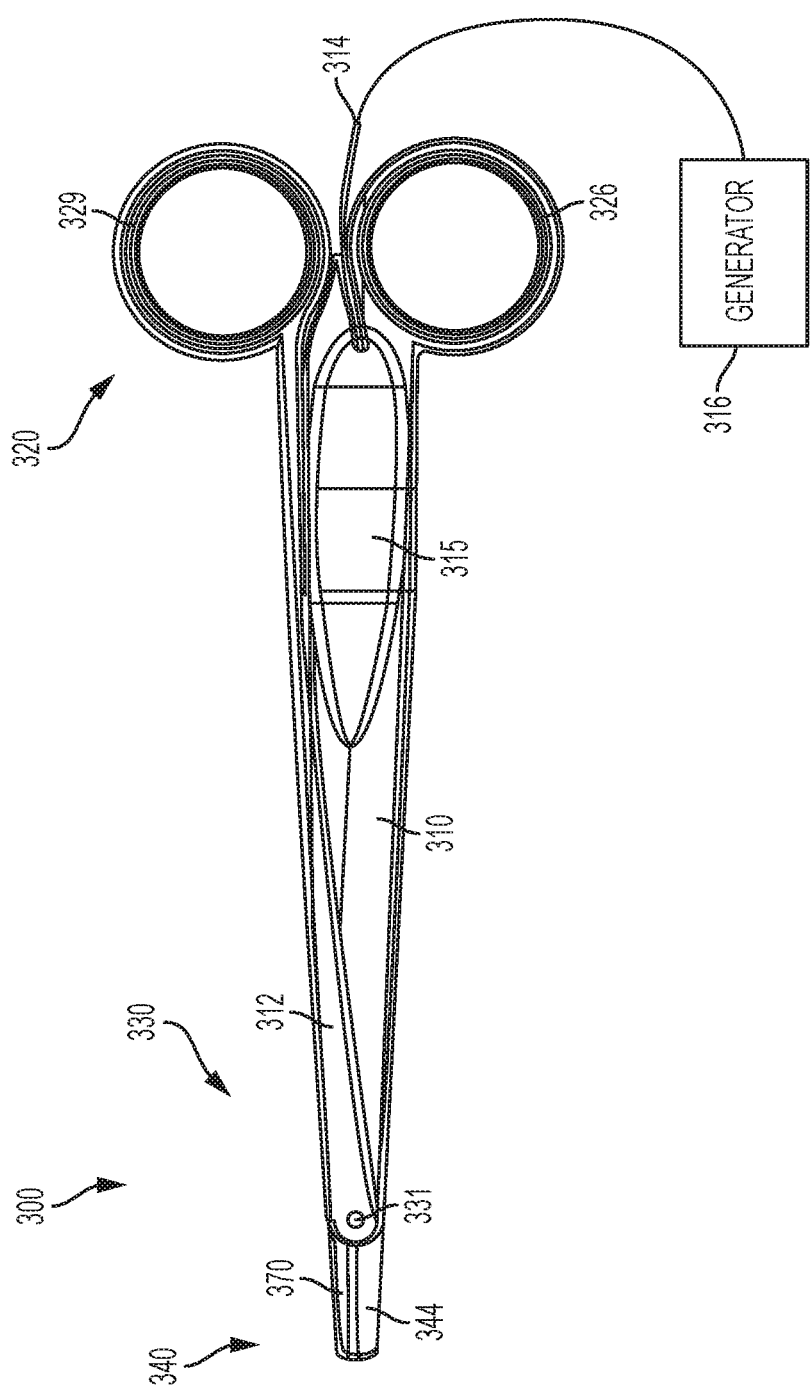
FIG. 44 is a side view of the ultrasonic surgical instrument shown in FIG. 43.
Figure 45:
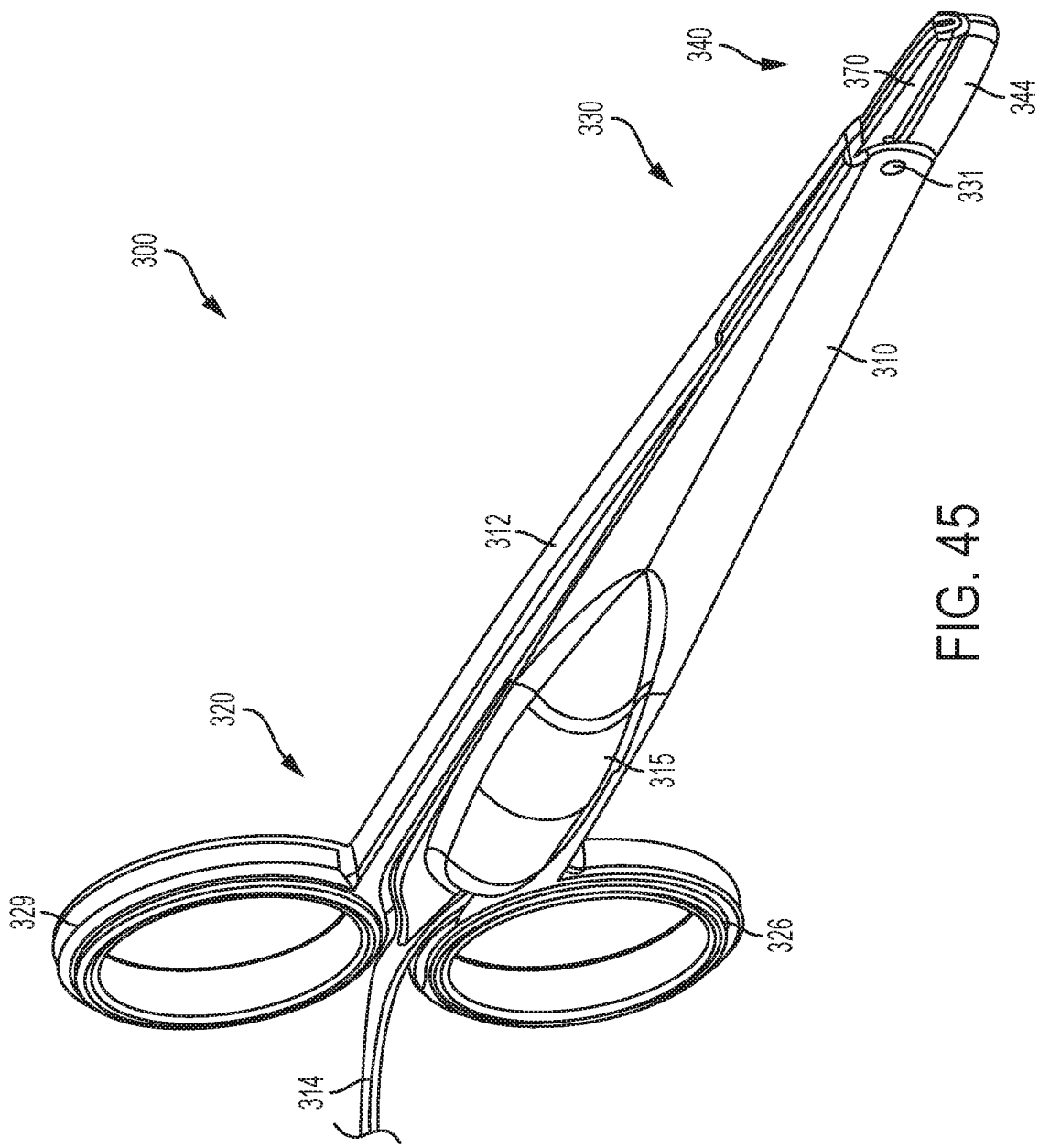
FIG. 45 is a front perspective view of the ultrasonic surgical instrument shown in FIGS. 43 and 44.
Figure 46:
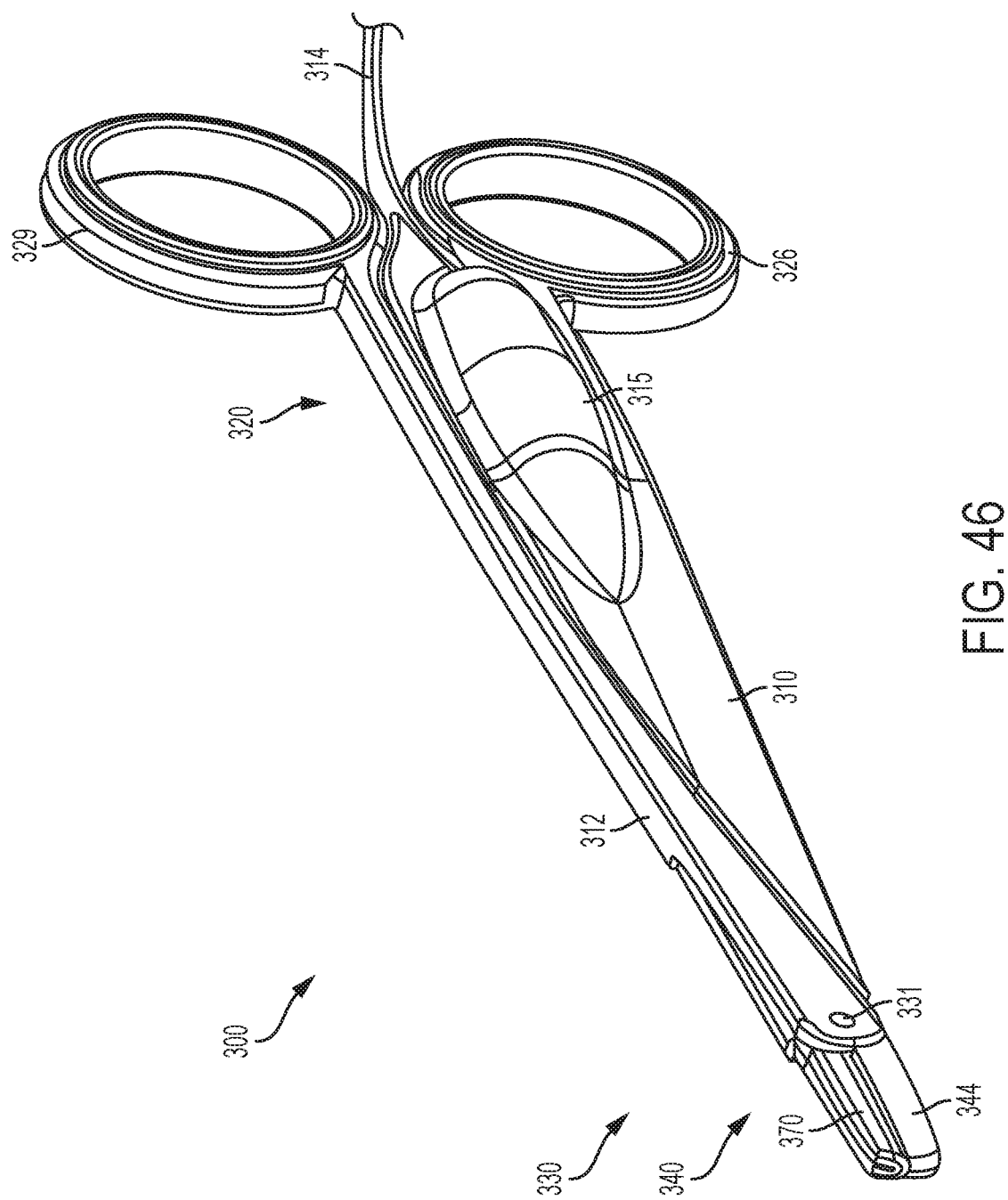
FIG. 46 is a front perspective view of the ultrasonic surgical instrument shown in FIGS. 43-45.

Referring to FIGS. 41 and 42, a sheath 214d comprises an open slot 222 extending longitudinally along the entire proximal-distal length of the sheath 214d. The sheath 214d also comprises reduced outside diameter portions 216 located on the proximal and distal ends of the sheath 214d. The ultrasonic transmission waveguide 220 and the isolation spacers 218a are inserted through the slot 222 and into the lumen 217d of the sheath 214d, as indicated by the arrow 219, without a need to insert either an ultrasonic transducer or the compound curvature component 275 and the ultrasonic surgical blade 270 through the lumen 217d of the sheath 214d. The circumference of the sheath 214d is then compressed until the longitudinal edges of the slot 222 meet and form a seam 233, thereby closing the slot 222. A distal end cap 260 and a proximal end cap 265 are then press fit onto the distal and proximal ends, respectively, of the sheath 214d, as indicated by arrows 221, wherein the reduced outside diameter portions 216 of the sheath 214d are inserted into the lumens 262 of the end caps 260 and 265.

The press fitting of the end caps 260 and 265 over the reduced outside diameter portions 216 of the sheath 214d close the slot 222, which seals the ultrasonic transmission waveguide 220 and the isolation spacers 218a within the lumen 217*d* of the sheath 214*d*. Optionally, the seam 233 may be laser welded, ultrasonic welded, bonded with an adhesive, or otherwise bonded. Alternatively, or additionally, a shrinkable tube (not shown) is positioned over the outer circumference of the sheath 214*d* and shrunk to further circumferentially seal the ultrasonic transmission waveguide 220 and the isolation spacers 218*a* within the lumen 217*d* of the sheath 214*d*.

The proximal end cap 265 may comprise external threads (not shown) located on the outer circumference surface of the end cap 265. A second sheath 280 has an inside diameter that is larger than the outside diameter of the sheath 214*d* and the proximal end cap 265. The second sheath 280 may comprise internal threads (not shown) located on the inner circumferential surface of the second sheath. The external threads on the proximal end cap 265 and the internal threads on the second sheath 280 mutually engage to attach the second sheath 280 to the sheath 214*d*. This allows multiple sheath segments to be joined together using an end cap as a coupler, where the diameter of the most distal sheath segment can be minimized relative to the more proximal sheath segment(s). In examples comprising a shrinkable tube (not shown), the shrunk tube may extend over both of the sheath segments 214*d* and 280, including the threaded joint between the second sheath 280 and the proximal end cap 265.

In connection with the examples described above, certain components of the acoustic systems (ultrasonic surgical blades, compound curvature components, ultrasonic transmission waveguides (including separate linear and curved regions), acoustic horns, and the like) are illustrated in the drawings as a single, contiguous piece of material (see, e.g., FIGS. 9-12, 19, 23, and 27-31, and 33-42). In such examples, the acoustic couplings between each component (or portions thereof) is provided by the contiguous material of the integrally formed components (and portions thereof). It is understood, however, that each component (or portion thereof) may be produced separately and acoustically coupled together in an operable manner, for example, using operable fastening mechanisms (e.g., threaded couplings) or metallurgical bonding techniques (e.g., welding).

Ultrasonic surgical blades and the associated acoustic components (e.g., ultrasonic transmission waveguides, acoustic horns, and the like) may be produced by forming and/or machining round bar or rod stock of a suitable metallic material such as titanium or titanium alloy, for example, to form an at least partially integral acoustic system. In some examples, it may be advantageous to produce ultrasonic surgical blades and integral acoustic components from a single piece of sheet metal stock that can be cut and formed instead of machined like bar or rod stock, and thus decrease manufacturing costs.

Referring to FIGS. 43-46, an ultrasonic surgical instrument 300 is shown having a scissor grip configuration. The ultrasonic surgical instrument 300 comprises a transducer/waveguide housing 310 and a clamp actuation member 312. The transducer/waveguide housing 310 and the clamp actuation member 312 are pivotably connected through a pivotable joint 331. The ultrasonic surgical instrument 300 comprises finger grip rings 326 and 329 integrally formed on the transducer/waveguide housing 310 and the clamp actuation member 312, respectively, at the proximal end 320 of the ultrasonic surgical instrument 300. The transducer/waveguide housing 310 comprises a transducer portion 315 within which an ultrasonic transducer 350 is housed (see FIGS. 51-54). The ultrasonic transducer 350 is coupled to a generator 316 via a cable 314 and may operate and comprise the features and characteristics described above.

Figure 47:
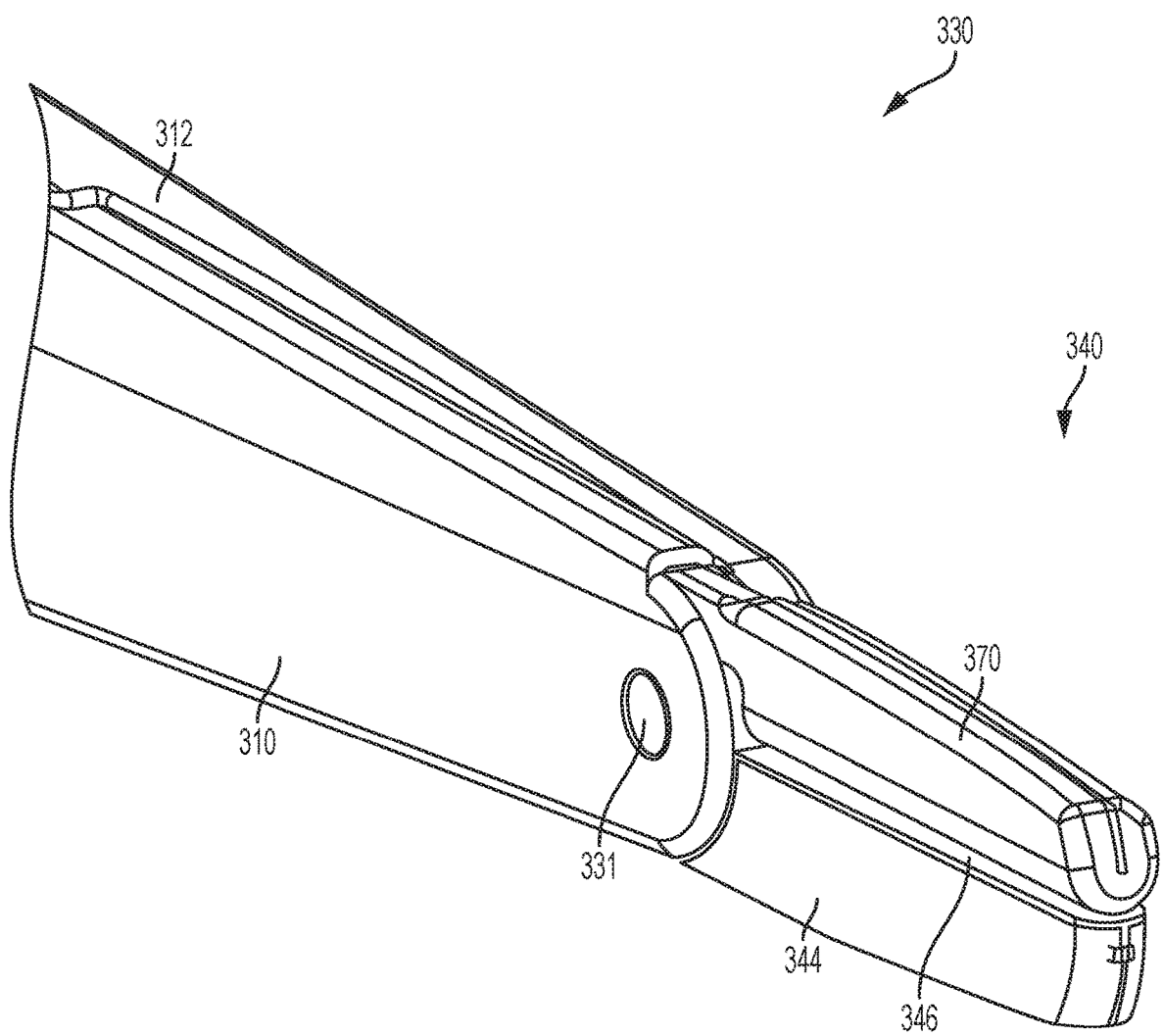
FIG. 47 is a front perspective view of the end-effector of the ultrasonic surgical instrument shown in FIGS. 43-46.
Figure 48:
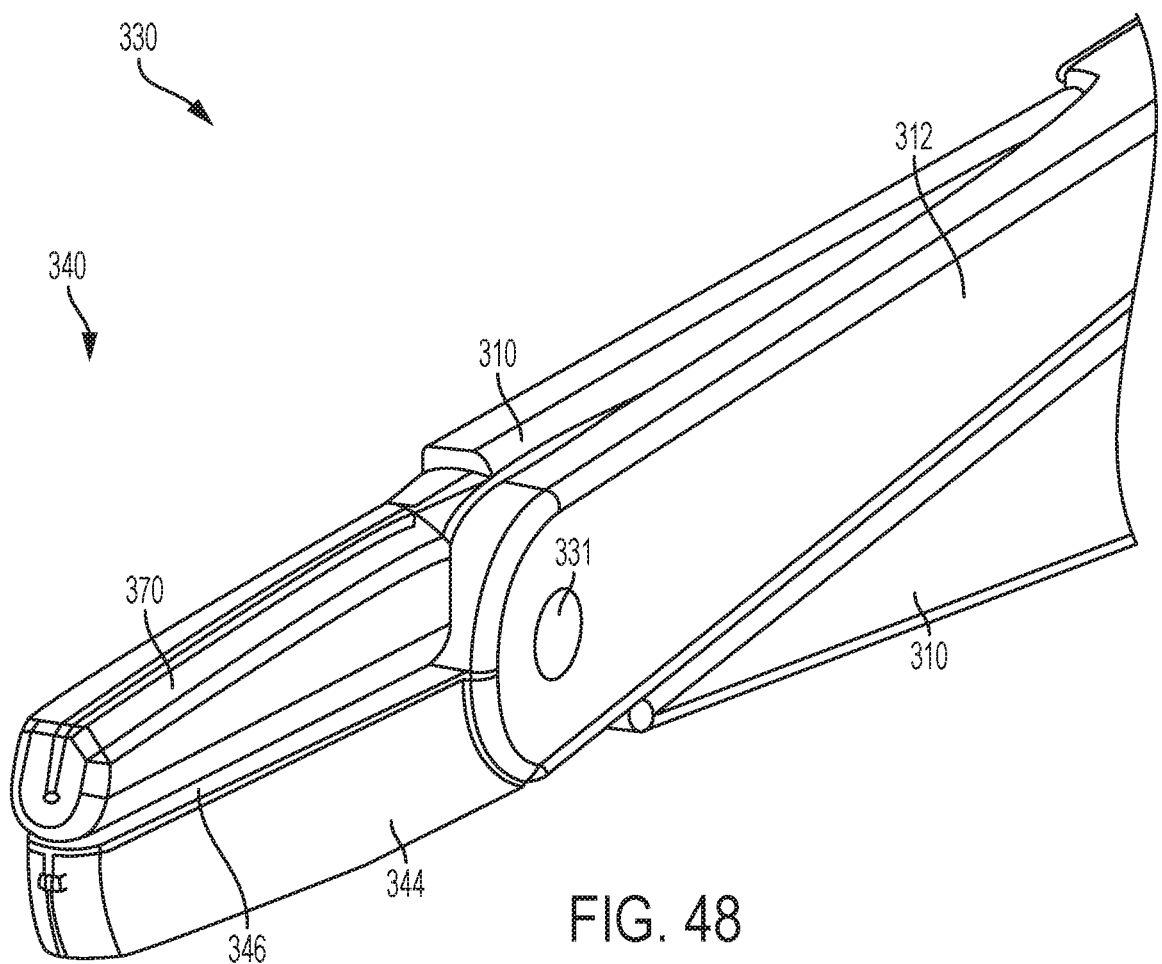
FIG. 48 is a front perspective view of the end-effector of the ultrasonic surgical instrument shown in FIGS. 43-46.

Referring to FIGS. 47 and 48, the transducer/waveguide housing 310 and the clamp actuation member 312 extend proximally from the pivotable joint 331. The ultrasonic surgical instrument 300 comprises an end-effector 340 extending distally from the pivotable joint 331 at the distal end 330 of the ultrasonic surgical instrument 300. The end-effector 340 comprises an ultrasonic surgical blade 370 and a clamp arm 344. The clamp arm 344 is integrally formed with the clamp actuation member 312 and extends distally from the pivotable joint 331. The clamp arm 344 comprises an optional clamp pad 346 which provides a tissue-engaging surface on the clamp arm 344.

Figure 49:
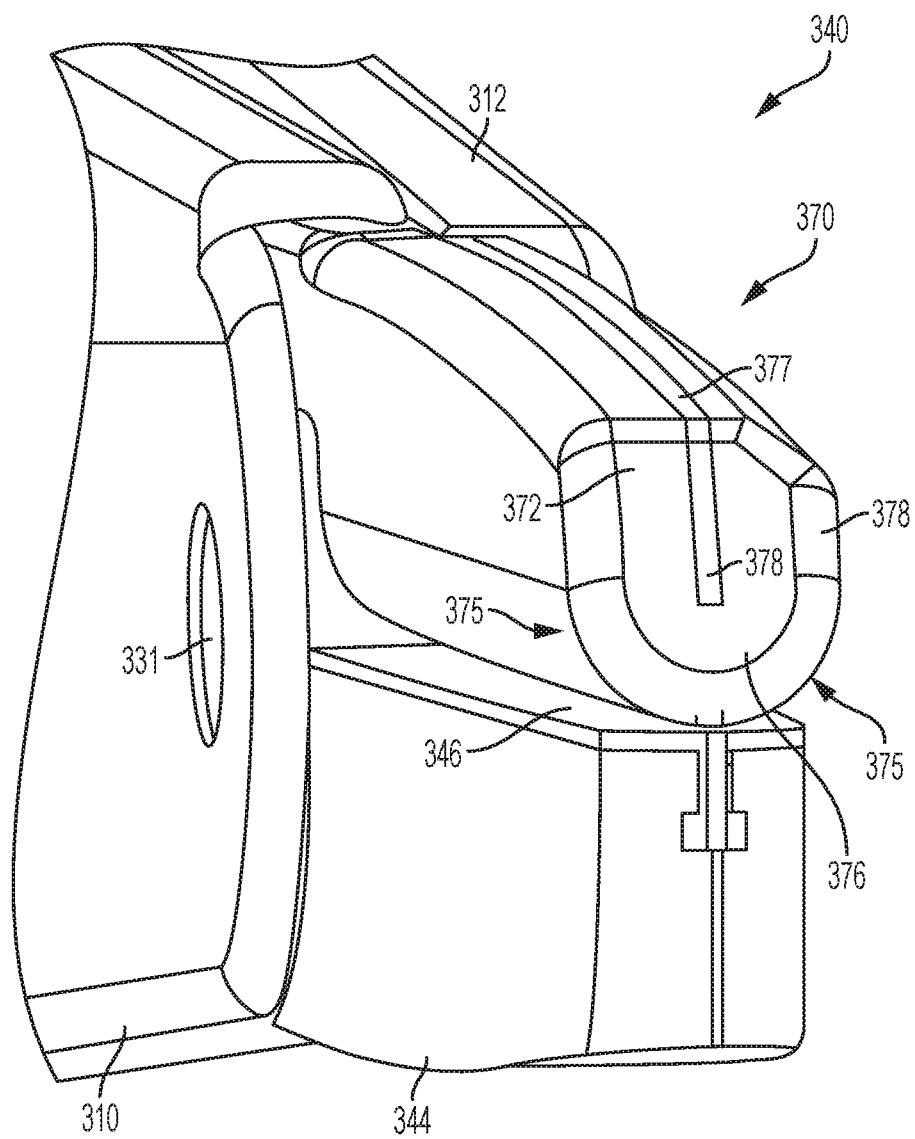
FIG. 49 is a front perspective view of the end-effector of the ultrasonic surgical instrument shown in FIGS. 43-46.
Figure 50:
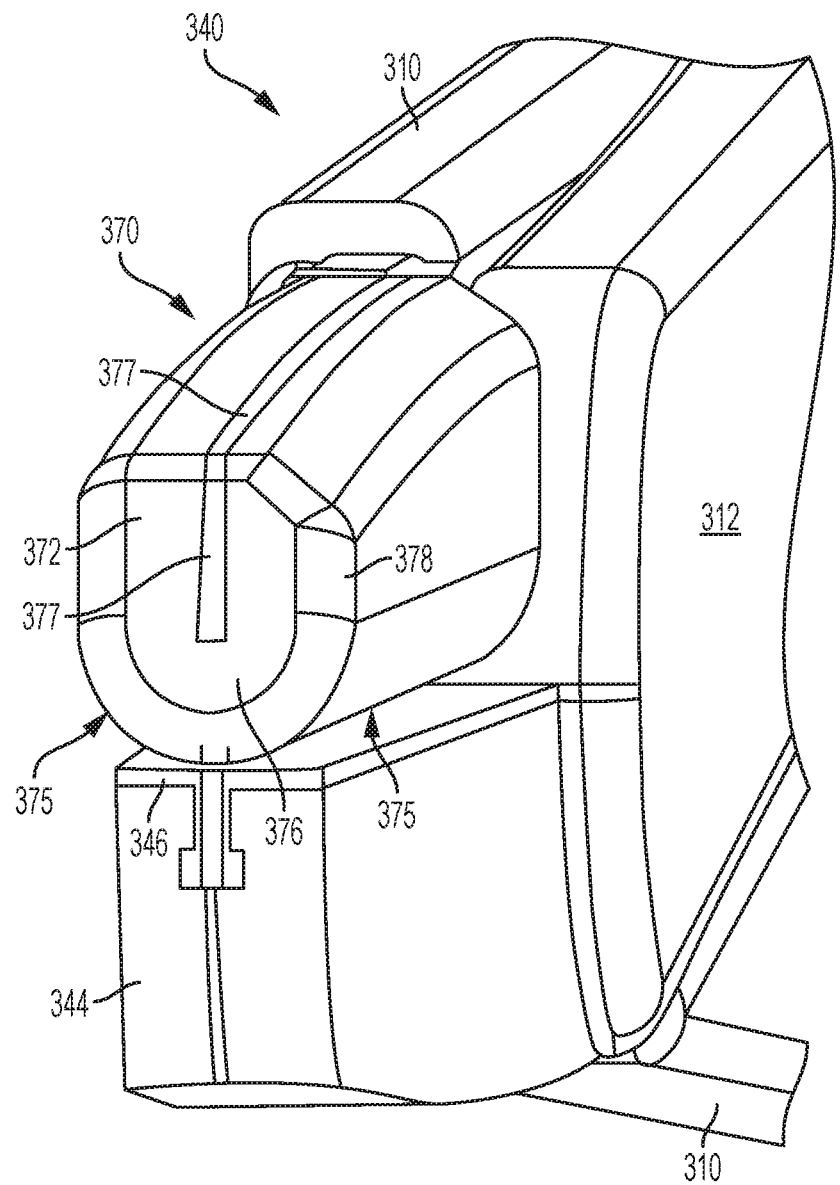
FIG. 50 is a front perspective view of the end-effector of the ultrasonic surgical instrument shown in FIGS. 43-46.
Figure 51:
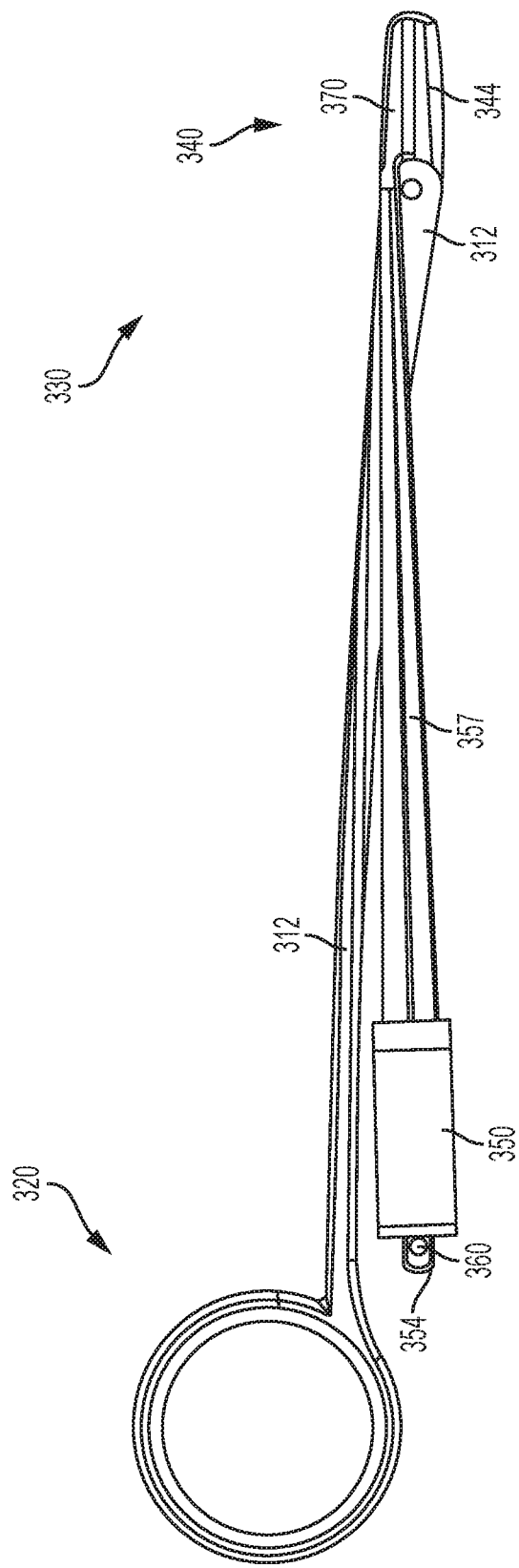
FIG. 51 is a side view schematic diagram of the ultrasonic surgical instrument shown in FIGS. 43-46 with a transducer/waveguide housing removed to show the ultrasonic transducer and the ultrasonic transmission waveguide.
Figure 52:
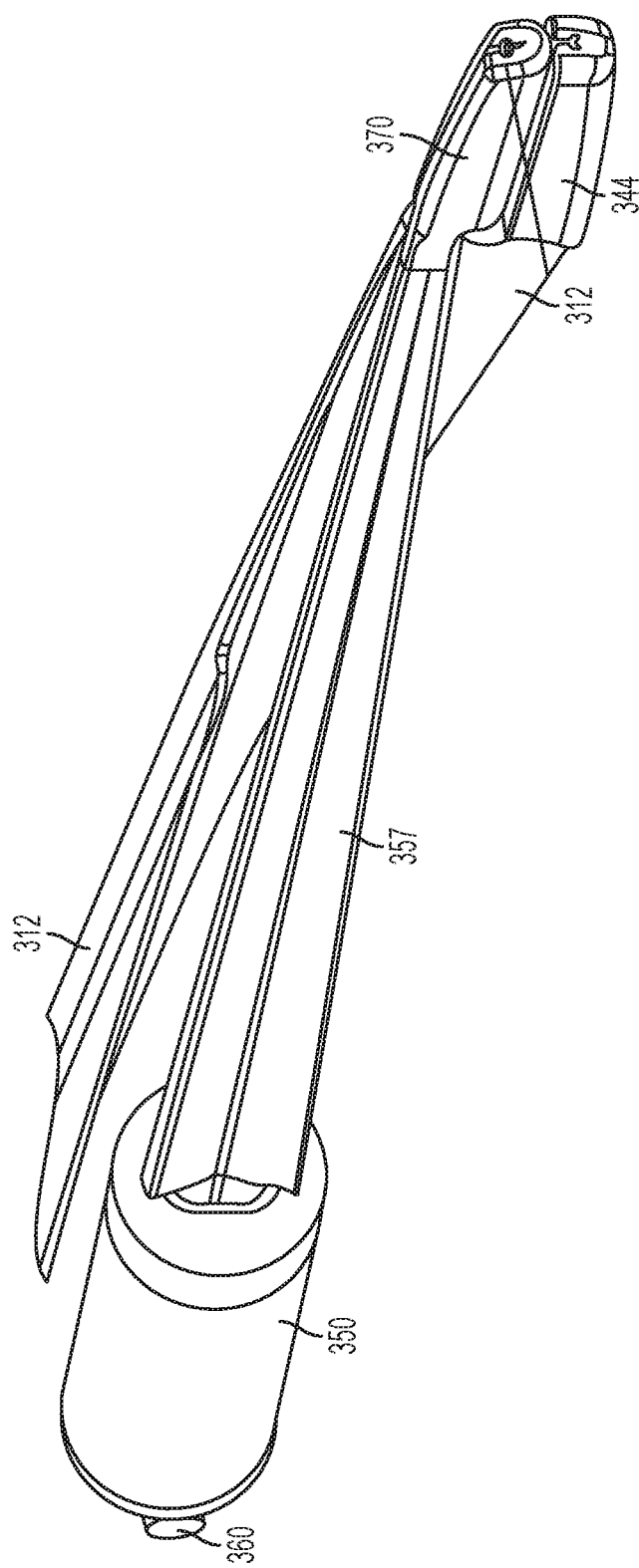
FIG. 52 is a perspective view schematic diagram of the ultrasonic surgical instrument as shown in FIG. 51.

Referring again to FIGS. 49 and 50, the ultrasonic surgical blade 370 comprises a body portion 372, a bent portion 376, and a folded portion 378. A gap 377 is located between the body portion 372 and the folded portion 378. In some examples, the gap 377 may contain an isolation spacer or other filler material (e.g., an elastomeric material such as silicone rubber) that maintains separation of the body portion 372 and the folded portion 378 and prevents contact during ultrasonic vibratory activation of the ultrasonic surgical blade 370. The ultrasonic surgical blade 370 comprises a tissue-engaging surface 375 which is located on the bent portion 376.

Referring to FIGS. 51, 52, 55, and 56, the ultrasonic surgical instrument 300 comprises an acoustic system 380 comprising the ultrasonic surgical blade 370, an ultrasonic transmission waveguide 357, and a transduction shaft 354. As shown in FIGS. 55 and 56, the acoustic system 380 is formed from a single, contiguous piece of material (e.g., a single piece of sheet metal stock that is cut and formed to produce the ultrasonic surgical blade 370, the ultrasonic transmission waveguide 357, and the transduction shaft 354). Thus, the ultrasonic surgical blade 370, the ultrasonic transmission waveguide 357, and the transduction shaft 354 are integrally formed from the single, contiguous piece of material (e.g., a single piece of sheet metal stock).

Referring to FIGS. 56 and 57A, and as described above, the ultrasonic surgical blade 370 comprises a body portion 372, a bent portion 376, a folded portion 378, a gap 377 located between the body portion 372 and the folded portion 378 (optionally containing an isolation spacer or other filler material that maintains separation of the body portion 372 and the folded portion 378 and prevents contact during ultrasonic vibratory activation of the ultrasonic surgical blade 370), and a tissue-engaging surface 375 located on the bent portion 376. As shown in FIG. 57A, the ultrasonic surgical blade 370 comprises a U-shaped cross-section transverse to a central transducer/waveguide axis 366 (see FIG. 55).

Referring to FIGS. 55, 56, and 57B, the ultrasonic transmission waveguide 357 comprises a top portion 392 and a bottom portion 394. The top portion 392 and the bottom portion 394 are separated by an inward bend 386 and an outward bend 388, which coincide with the central transducer/waveguide axis 366. The inward bend 386 forms an inwardly bent side 382 of the ultrasonic transmission waveguide 357. The outward bend 388 forms an outwardly bent side 384 of the ultrasonic transmission waveguide 357. As shown in FIG. 57B, the ultrasonic transmission waveguide 357 comprises a V-shaped cross-section transverse to the central transducer/waveguide axis 366.

Referring to FIGS. 55 and 56, the transduction shaft 354 is acoustically coupled to the ultrasonic transmission waveguide 357 through a T-shaped region formed where the top portion 392 and the bottom portion 394 begin to transversely extend from the central (longitudinal) transducer/waveguide axis 366 (and also from the inward and outward bends 386 and 388). As show in FIG. 55, the T-shaped transition region is formed by the intersection of the transduction shaft 354 with the top and bottom proximal edges 358 and 359 of the top and bottom portions 392 and 394 of the ultrasonic transmission waveguide 357. The transduction shaft 354 also comprises a proximal bore 362 through the thickness of the transduction shaft 354.

Referring again to FIGS. 43-46, the transduction shaft 354 and the ultrasonic transmission waveguide 357 of the acoustic system 380 are located within the transducer/waveguide housing 310, and the ultrasonic surgical blade extends outside the transducer/waveguide housing 310, distally from the pivotable joint 331. Referring again to FIGS. 51 and 52, the transduction shaft 354 of the acoustic system 380 is located through an aperture that extends the length of the ultrasonic transducer 350. The ultrasonic transducer 350 is clamped between the top and bottom proximal edges 358 and 359 of the ultrasonic transmission waveguide 357 and a cam lock 360 extending through the proximal bore 362 in the transduction shaft 354.

Figure 53:
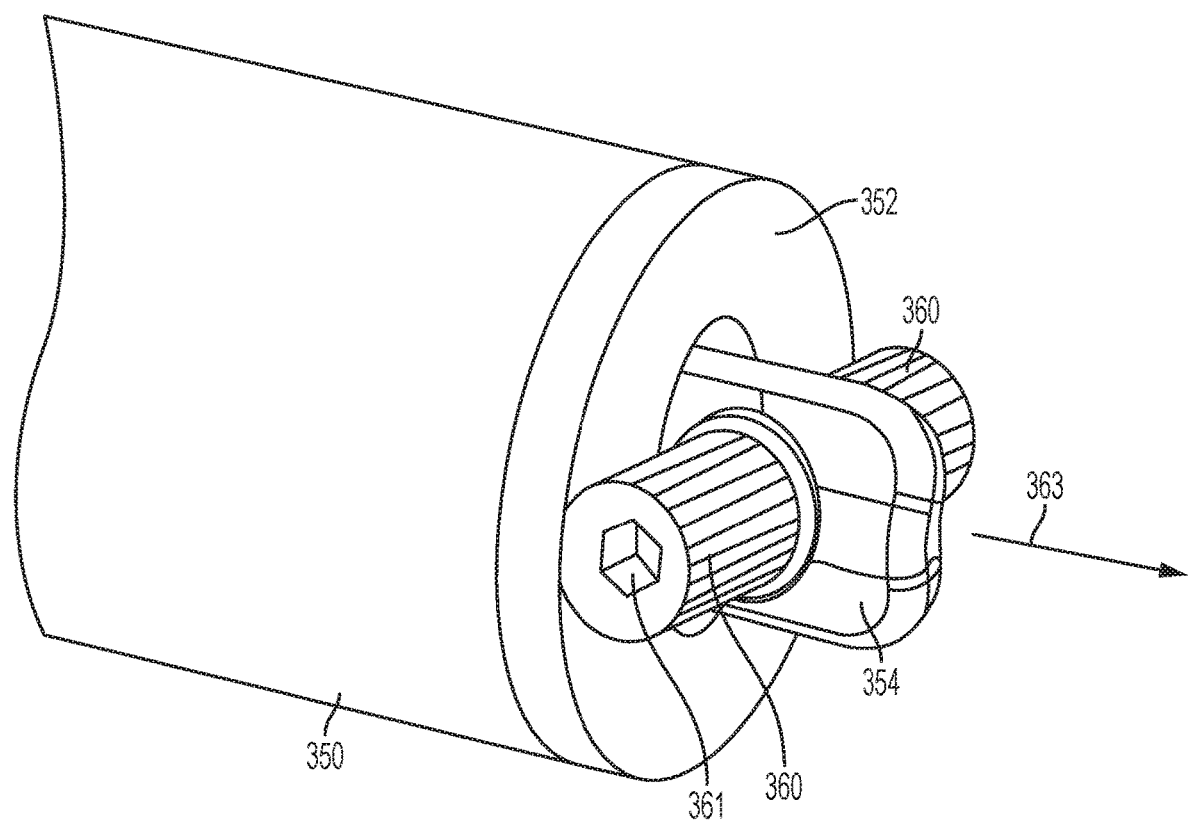
FIG. 53 is a rear perspective view schematic diagram showing a cam lock assembly for acoustically coupling an ultrasonic transmission waveguide to the ultrasonic transducer.
Figure 54:
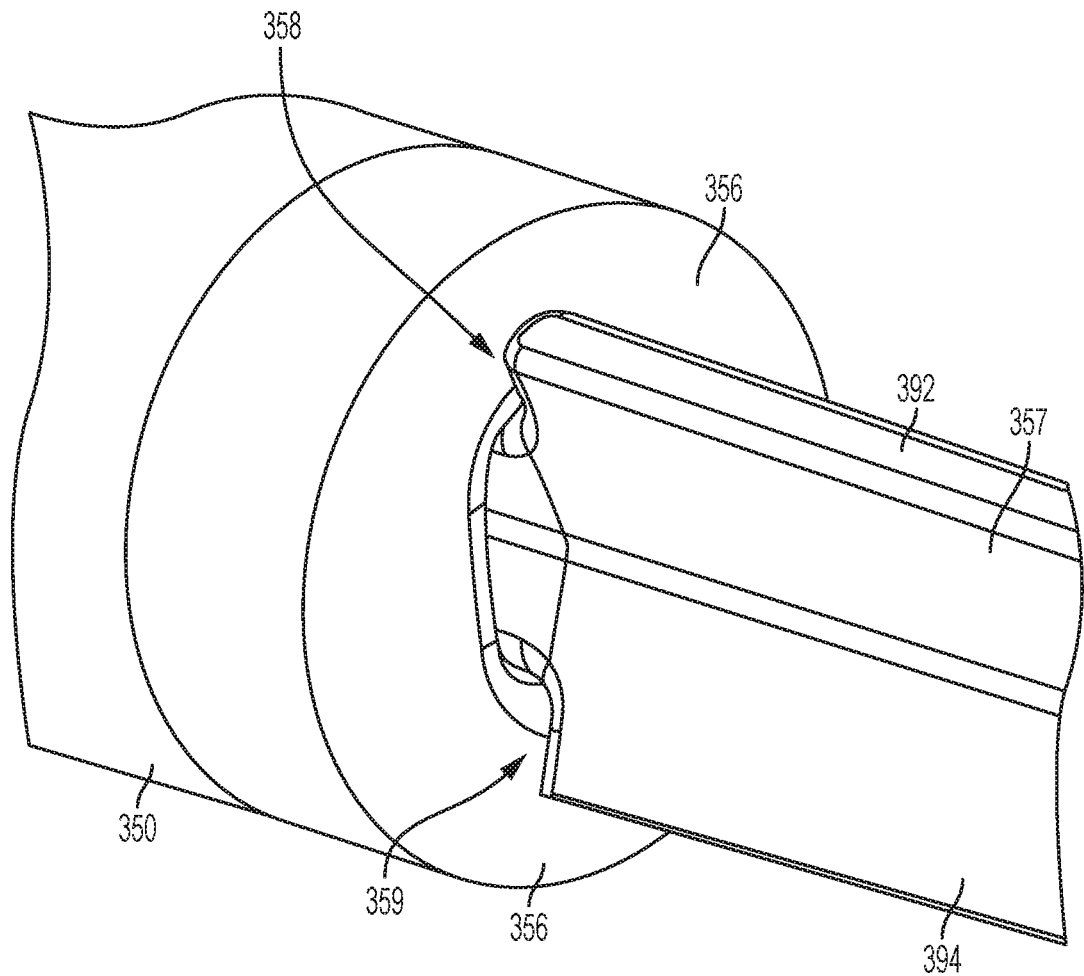
FIG. 54 is a front perspective view schematic diagram showing an ultrasonic transmission waveguide acoustically coupled to the ultrasonic transducer.

Referring to FIGS. 53 and 54, the top and bottom proximal edges 358 and 359 of the ultrasonic transmission waveguide 357 engage the distal end surface 356 of the ultrasonic transducer 350. The cam lock 360 engages the proximal end surface 352 of the ultrasonic transducer 350. The rotation of the cam lock 360 (for example, using a hex wrench in the hex-shaped blind bore 361) forces the transduction shaft 354 proximally, as indicated by arrow 363, which tensions the transduction shaft 354 and secures the top and bottom proximal edges 358 and 359 of the ultrasonic transmission waveguide 357 against the distal end surface 356 of the ultrasonic transducer 350, thereby acoustically coupling the ultrasonic transmission waveguide 357 to the ultrasonic transducer 350.

As shown in FIGS. 55 and 56, the width of the ultrasonic transmission waveguide 357 perpendicular to the central transducer/waveguide axis 366 decreases from a maximum at the top and bottom proximal edges 358 and 359 to a minimum at the distal transition region with the ultrasonic surgical blade 370. The ultrasonic transmission waveguide 357 thus has a tapered width that decreases from a maximum at the acoustic coupling with the ultrasonic transducer 350 to a minimum at the transition to the ultrasonic surgical blade 370 (see FIGS. 51 and 52). This longitudinal taper allows the ultrasonic transmission waveguide 357 to also function as an acoustic horn that focuses and amplifies the ultrasonic vibrations produced by the ultrasonic transducer 350 to the ultrasonic surgical blade 370. Referring to FIG. 55, the tissue-engaging surface 375 of the ultrasonic surgical blade 370 is transversely off-set from the central transducer/waveguide axis 366 by a linear distance Δ.

In various examples, a foot pedal or other switching device (not shown) operably connected to the generator 316 may be employed to control the application of electrical power from the generator 316 to the ultrasonic transducer 350. When power is applied to the ultrasonic transducer 350 by operation of a foot pedal or other switch arrangement, the acoustic system 380 may, for example, cause the ultrasonic surgical blade 370 to vibrate longitudinally along the central waveguide/shaft axis 366 (see FIGS. 55 and 56) at approximately 55.5 kHz, and the amount of longitudinal movement will vary proportionately with the amount of driving power (electrical current) applied, which may be adjustably selected by a surgeon or other operator of the ultrasonic surgical instrument 300.

The ultrasonic transducer 350 transmits ultrasonic vibrations to the acoustically coupled ultrasonic transmission waveguide 357 through the T-shaped region where the top and bottom proximal edges 358 and 359 of the top and bottom portions 392 and 394 of the ultrasonic transmission waveguide 357 are secured against the distal end surface 356 of the ultrasonic transducer 350. The ultrasonic vibrations are then transmitted and focused through the ultrasonic transmission waveguide 357 to the ultrasonic surgical blade 370. A surgeon or other operator can pivot the ultrasonic surgical blade 370 and the clamp arm 344 toward and away from each other by pivoting the transducer/waveguide housing 310 and the clamp actuation member 312 toward and away from each other using the finger grip rings 326 and 329.

The instruments, devices, assemblies, and systems described in this specification can be configured for disposal after a single use, or they can be configured for reuse one or more times. In either case, however, the instruments, devices, assemblies, and systems can be reconditioned for reuse after at least one use. Reconditioning can include any combination of the steps of disassembly of the instruments, devices, assemblies, and systems, followed by cleaning or replacement of particular pieces, and subsequent reassembly. For example, an instrument or device can be disassembled, and any number of the particular pieces or parts of the device can be selectively replaced or removed in any combination. Upon cleaning and/or replacement of particular parts, the instrument or device can be reassembled for subsequent use either at a reconditioning facility, or by a surgical team immediately prior to a surgical procedure. Those skilled in the art will appreciate that reconditioning of an instrument or device can utilize a variety of techniques for disassembly, cleaning/replacement, and reassembly. Use of such techniques, and the resulting reconditioned device, are all within the scope of the invention(s) described in this specification.

By way of example only, the instruments described in this specification may be processed before use in a surgical procedure. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill or otherwise inactivate bacteria, viruses, or other microorganisms or pathogenic material on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide treatment, plasma peroxide treatment, or steam treatment.

The ultrasonic surgical instruments described in this specification may be used for performing laparoscopic and minimally invasive surgical procedures. However, the reader will appreciate that the instruments can be used in numerous surgical procedures and applications including, for example, in connection with open or otherwise invasive surgical procedures. The reader will further appreciate that the instruments may be inserted into a patient's body in any way, such as through a natural orifice (e.g., ear, nose, mouth, or rectum), through an incision or puncture hole formed in tissue, and the like. The end-effector portions of the instruments can be inserted directly into a patient's body or can be inserted through an access device (e.g., a trocar) that has a working channel through which the end-effector and an elongated shaft of a surgical instrument can be advanced. Additionally, it is understood that the ultrasonic surgical instruments described in this specification may be implemented in medical surgical procedures on humans or in veterinary surgical procedures on animals.

Aspects of the Invention

Aspects of the invention include, but are not limited to, the following numbered clauses.

1. An ultrasonic surgical instrument comprising: an ultrasonic transducer having a central transducer axis; an acoustic horn acoustically coupled to the ultrasonic transducer; an ultrasonic transmission waveguide acoustically coupled to the acoustic horn, the ultrasonic transmission waveguide comprising a curved portion and a linear portion and; an ultrasonic surgical blade acoustically coupled to the ultrasonic transmission waveguide; wherein the linear portion of the ultrasonic transmission waveguide and the ultrasonic surgical blade are angularly off-set from the central transducer axis.

2. The ultrasonic surgical instrument of clause 1, wherein the linear portion of the ultrasonic transmission waveguide has a central waveguide axis, and wherein the central waveguide axis and the central transducer axis intersect and form an off-set angle ranging from 120-degrees to 150-degrees.

3. The ultrasonic surgical instrument of clause 1, further comprising: a handle assembly comprising a handle body and a clamp actuation member pivotably coupled to the handle body; a shaft assembly connected to the handle assembly; and an end-effector connected to the shaft assembly, the end-effector comprising the ultrasonic surgical blade and a clamp arm pivotably coupled to the shaft assembly, wherein: the ultrasonic transducer, the acoustic horn, and the curved portion of the ultrasonic transmission waveguide are located within the handle body; and the linear portion of the ultrasonic transmission waveguide is located within the shaft assembly.

4. The ultrasonic surgical instrument of clause 3, wherein the shaft assembly comprises a reciprocating upper shaft member and a lower shaft member integrally formed with the handle body, and wherein the linear portion of the ultrasonic transmission waveguide is located between the reciprocating upper shaft member and the lower shaft member.

5. The ultrasonic surgical instrument of clause 4, wherein: the clamp actuation member is pivotably coupled to the handle body and pivotably coupled to the reciprocating upper shaft member; the reciprocating upper shaft member is pivotably coupled to the clamp arm; and the clamp arm is pivotably coupled to the lower shaft member.

6. The ultrasonic surgical instrument of clause 5, wherein: pivotal motion of the clamp actuation member toward the handle body causes distal translational motion of the reciprocating upper shaft member, and the distal translational motion of the reciprocating upper shaft member causes pivotal motion of the clamp arm toward the ultrasonic surgical blade, thereby closing the end-effector; and pivotal motion of the clamp actuation member away from the handle body causes proximal translational motion of the reciprocating upper shaft member, and the proximal translational motion of the reciprocating upper shaft member causes pivotal motion of the clamp arm away from the ultrasonic surgical blade, thereby opening the end-effector.

7. The ultrasonic surgical instrument of any one of clauses 1-6, further comprising a compound curvature component acoustically coupling the ultrasonic surgical blade to the linear portion of the ultrasonic transmission waveguide, wherein the linear portion of the ultrasonic transmission waveguide has a central waveguide axis, and wherein the compound curvature region transversely off-sets the ultrasonic surgical blade from the central waveguide axis.

8. The ultrasonic surgical instrument of clause 7, wherein the ultrasonic surgical blade comprises a tissue-engaging surface that is parallel to the central waveguide axis, and wherein the tissue-engaging surface is transversely off-set past an outer surface of a shaft assembly containing the linear portion of the ultrasonic transmission waveguide.

9. An ultrasonic surgical instrument comprising: an ultrasonic transducer; an acoustic horn acoustically coupled to the ultrasonic transducer; an ultrasonic transmission waveguide acoustically coupled to the acoustic horn, the ultrasonic transmission waveguide having a central waveguide axis; and an ultrasonic surgical blade acoustically coupled to the ultrasonic transmission waveguide through a compound curvature component; wherein the compound curvature component transversely off-sets the ultrasonic surgical blade from the central waveguide axis.

10. The ultrasonic surgical instrument of clause 9, further comprising a shaft assembly comprising an outer sheath around at least a portion of the ultrasonic transmission waveguide, wherein the ultrasonic surgical blade is transversely off-set past an outer surface of the outer sheath.

11. The ultrasonic surgical instrument of clause 10, wherein the outer sheath comprises a closed and/or sealed slot extending longitudinally along at least a portion of the outer sheath length.

12. The ultrasonic surgical instrument of clause 11, wherein the closed and/or sealed slot comprises a sealing member positioned in the slot.

13. The ultrasonic surgical instrument of clause 11, wherein the closed and/or sealed slot comprises a shrunk tube positioned around the outer sheath circumference.

14. The ultrasonic surgical instrument of clause 11, wherein the closed and/or sealed slot comprises a bonded seam.

15. The ultrasonic surgical instrument of any one of clauses 9-14, wherein the ultrasonic transducer has a central transducer axis, the ultrasonic transmission waveguide comprises a curved portion and a linear portion, and the linear portion of the ultrasonic transmission waveguide and the ultrasonic surgical blade are angularly off-set from the central transducer axis.

16. The ultrasonic surgical instrument of clause 15, wherein the linear portion of the ultrasonic transmission waveguide defines the central waveguide axis, and wherein the central waveguide axis and the central transducer axis intersect and form an off-set angle ranging from 120-degrees to 150-degrees.

17. An ultrasonic surgical instrument comprising: an ultrasonic transducer; an ultrasonic transmission waveguide acoustically coupled to the ultrasonic transducer; and an ultrasonic surgical blade integrally formed with the ultrasonic transmission waveguide, wherein the ultrasonic transmission waveguide has a tapered width that decreases from a maximum at the acoustic coupling with the ultrasonic transducer to a minimum at a transition to the ultrasonic surgical blade.

18. The ultrasonic surgical instrument of clause 17, further comprising: a housing containing the ultrasonic transducer and the ultrasonic transmission waveguide; a clamp actuation member pivotably connected to the housing through a pivotable joint; and a clamp arm integrally formed with the clamp actuation member; wherein the housing and the clamp actuation member extend proximally from the pivotable joint; and wherein the clamp arm and the ultrasonic surgical blade extend distally from the pivotable joint.

19. The ultrasonic surgical instrument of clause 17 or clause 18, wherein the ultrasonic surgical blade comprises: a body portion acoustically coupled to the ultrasonic transmission waveguide; a bent portion forming a tissue-engaging surface; and a folded portion forming a gap between the body portion and the folded portion.

20. The ultrasonic surgical instrument of any one of clauses 17-19, wherein the ultrasonic transmission waveguide has a V-shaped cross-section.

21. The ultrasonic surgical instrument of any one of clauses 17-20, further comprising a transduction shaft integrally formed with the ultrasonic transmission waveguide, wherein the transduction shaft is located through an aperture extending through the length of the ultrasonic transducer, and wherein the ultrasonic transducer is clamped between proximal edges of the ultrasonic transmission waveguide and a cam lock extending through a proximal bore in the transduction shaft.

Various features and characteristics of the invention(s) are described in this specification and illustrated in the drawings to provide an understanding of the structure, function, operation, and/or manufacture of the disclosed instruments, devices, assemblies, systems, and methods. It is understood that the various features and characteristics of the inventions (s) described in this specification and illustrated in the drawings can be combined in any suitable manner, regardless of whether such features and characteristics are expressly described or illustrated in combination in this specification. The Inventors and the Applicant expressly intend such combinations of features and characteristics to be included within the scope of the invention(s) described in this specification. As such, the claims can be amended to recite, in any combination, any features and characteristics expressly or inherently described in, or otherwise expressly or inherently supported by, this specification, including features and characteristics illustrated in the drawings. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements (e.g., 35 U.S.C. § 112(a) and Article 123(2) EPC).

The invention(s) described in this specification can comprise, consist of, or consist essentially of the various features and characteristics described in this specification. The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. Thus, an instrument, device, assembly, system, or method, and the like, that "comprises," "has," "includes," or "contains" one or more features and/or characteristics possesses those one or more features and/or characteristics, but is not limited to possessing only those one or more features and/or characteristics. Likewise, an element of an instrument, device, assembly, system, or method, and the like, that "comprises," "has," "includes," or "contains" one or more features and/or characteristics possesses those one or more features and/or characteristics, but is not limited to possessing only those one or more features and/or characteristics, and may possess additional features and/or characteristics.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described processes, compositions, and products. Further, the use of a singular noun includes the plural, and the use of a plural noun includes the singular, unless the context of the usage requires otherwise.

Any patent, publication, or other document identified in this specification is incorporated by reference into this specification in its entirety unless otherwise indicated, but only to the extent that the incorporated material does not conflict with existing descriptions, definitions, statements, illustrations, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference. The amendment of this specification to add such incorporated subject matter will comply with written description, sufficiency of description, and added matter requirements (e.g., 35 U.S.C. § 112(a) and Article 123(2) EPC).

What is claimed is:

1. An ultrasonic surgical instrument comprising:
a handle assembly comprising a handle body and a clamp actuation member pivotably coupled to the handle body;
a shaft assembly connected to the handle assembly;
an ultrasonic transducer having a central transducer axis;
an acoustic horn acoustically coupled to the ultrasonic transducer;
an ultrasonic transmission waveguide acoustically coupled to the acoustic horn, the ultrasonic transmission waveguide having a central waveguide axis and comprising a compound curvature component, the compound curvature component comprising a proximal curved portion, a linear portion, and a distal curved portion, the linear portion positioned in between the proximal curved portion and the distal curved portion;
an ultrasonic surgical blade acoustically coupled to the distal curved portion of the ultrasonic transmission waveguide and having a central blade axis that is parallel to the central waveguide axis; and
an end-effector connected to the shaft assembly, the end-effector comprising the ultrasonic surgical blade and a clamp arm pivotably coupled to the shaft assembly, wherein the ultrasonic transducer and the acoustic horn are located within the handle body.

2. The ultrasonic surgical instrument of claim 1, wherein the central waveguide axis and the central transducer axis intersect and form an off-set angle ranging from 120-degrees to 150-degrees.

3. The ultrasonic surgical instrument of claim 1, wherein the shaft assembly comprises a reciprocating upper shaft member and a lower shaft member integrally formed with the handle body, and wherein the linear portion of the ultrasonic transmission waveguide is located between the reciprocating upper shaft member and the lower shaft member.

4. The ultrasonic surgical instrument of claim 3, wherein:
the clamp actuation member is pivotably coupled to the handle body and pivotably coupled to the reciprocating upper shaft member;
the reciprocating upper shaft member is pivotably coupled to the clamp arm; and
the clamp arm is pivotably coupled to the lower shaft member.

5. The ultrasonic surgical instrument of claim 4, wherein:
pivotal motion of the clamp actuation member toward the handle body causes distal translational motion of the reciprocating upper shaft member, and the distal translational motion of the reciprocating upper shaft member causes pivotal motion of the clamp arm toward the ultrasonic surgical blade, thereby closing the end-effector; and
pivotal motion of the clamp actuation member away from the handle body causes proximal translational motion of the reciprocating upper shaft member, and the proximal translational motion of the reciprocating upper shaft member causes pivotal motion of the clamp arm away from the ultrasonic surgical blade, thereby opening the end-effector.

6. The ultrasonic surgical instrument of claim 1, wherein the central blade axis is transversely off-set from the central waveguide axis by a linear distance greater than a width of a cross-sectional diameter of a shaft configured to house the ultrasonic transmission waveguide.

7. The ultrasonic surgical instrument of claim 6, wherein the ultrasonic surgical blade comprises a tissue-engaging surface that is parallel to the central waveguide axis, and wherein the tissue-engaging surface is transversely off-set from the central waveguide axis.

8. The ultrasonic surgical instrument of claim 7, wherein the tissue-engaging surface is a first tissue-engaging surface, and the ultrasonic surgical blade further comprises a second tissue-engaging surface positioned opposite of the first tissue-engaging surface and still parallel to the central waveguide axis, facing outwardly away from the central waveguide axis.

9. The ultrasonic surgical instrument of claim 1, wherein the shaft assembly houses the acoustic horn and the ultrasonic transmission waveguide up to a position of the proximal curved portion, wherein the ultrasonic surgical blade is transversely offset by the compound curvature component such that the central blade axis falls outside of the shaft assembly.

10. An ultrasonic surgical instrument comprising:
a handle assembly comprising a handle body and a clamp actuation member pivotably coupled to the handle body;
a shaft assembly connected to the handle assembly;
an ultrasonic transducer;
an acoustic horn acoustically coupled to the ultrasonic transducer;
an ultrasonic transmission waveguide acoustically coupled to the acoustic horn, the ultrasonic transmission waveguide having a central waveguide axis;
a compound curvature component comprising a proximal curved portion, a linear portion, and a distal curved portion, the linear portion positioned in between the proximal curved portion and the distal curved portion, the compound curvature component coupled to the ultrasonic transmission waveguide by the proximal curved portion,
an ultrasonic surgical blade acoustically coupled to the distal curved portion of the component curvature component and having a central blade axis; and
an end-effector connected to the shaft assembly, the end-effector comprising the ultrasonic surgical blade and a clamp arm pivotably coupled to the shaft assembly,
wherein the ultrasonic transducer and the acoustic horn are located within the handle body; and
wherein the compound curvature component transversely off-sets the ultrasonic surgical blade from the central waveguide axis, such that the central blade axis is parallel to the central waveguide axis.

11. The ultrasonic surgical instrument of claim 10, wherein the shaft assembly comprises an outer sheath around at least a portion of the ultrasonic transmission waveguide, wherein the ultrasonic surgical blade is transversely off-set from an outer sheath axis defined by an outer surface of the outer sheath.

12. The ultrasonic surgical instrument of claim 11, wherein the outer sheath comprises a closed and/or sealed slot extending longitudinally along at least a portion of the outer sheath length.

13. The ultrasonic surgical instrument of claim 12, wherein the closed and/or sealed slot comprises a sealing member positioned in the closed and/or sealed slot.

14. The ultrasonic surgical instrument of claim 12, wherein the closed and/or sealed slot comprises a shrunk tube positioned around the outer sheath circumference.

15. The ultrasonic surgical instrument of claim 12, wherein the closed and/or sealed slot comprises a bonded seam.

16. The ultrasonic surgical instrument of claim 10, wherein the central blade axis is transversely off-set from the central waveguide axis by a linear distance greater than a width of a cross-sectional diameter of a shaft configured to house the ultrasonic transmission waveguide.

17. The ultrasonic surgical instrument of claim 16, wherein the ultrasonic surgical blade comprises a tissue-engaging surface that is parallel to the central waveguide axis, and wherein the tissue-engaging surface is transversely off-set from the central waveguide axis.

18. The ultrasonic surgical instrument of claim 17, wherein the tissue-engaging surface is a first tissue-engaging surface, and the ultrasonic surgical blade further comprises a second tissue-engaging surface positioned opposite of the first tissue-engaging surface and still parallel to the central waveguide axis, facing outwardly away from the central waveguide axis.

19. The ultrasonic surgical instrument of claim 10, wherein the shaft assembly houses the acoustic horn and the ultrasonic transmission waveguide, wherein the ultrasonic surgical blade is transversely offset by the compound curvature component such that the central blade axis falls outside of the shaft assembly.

* * * * *